United States Patent [19]

Duggan et al.

[11] Patent Number: 5,281,585
[45] Date of Patent: Jan. 25, 1994

[54] FIBRINOGEN RECEPTOR ANTAGONISTS FOR INHIBITING AGGREGATION OF BLOOD PLATELETS

[75] Inventors: Mark E. Duggan, Schwenksville; Melissa S. Egbertson, Ambler; Nathan Ihle, Perkasie; George D. Hartman, Lansdale; Laura M. Turchi, Broomall; William F. Hoffman, Lansdale, all of Pa.

[73] Assignee: Merck & Co., Inc., Rahway, N.J.

[21] Appl. No.: 972,668

[22] Filed: Nov. 6, 1992

Related U.S. Application Data

[63] Continuation-in-part of Ser. No. 871,262, Apr. 23, 1992, abandoned, which is a continuation-in-part of Ser. No. 720,357, Jun. 25, 1991, abandoned, which is a continuation-in-part of Ser. No. 696,893, May 7, 1991, abandoned.

[51] Int. Cl.$^5$ .................. A61K 31/16; A61K 31/445; A61K 31/395; C07D 417/06; C07D 401/06
[52] U.S. Cl. .................. 514/79; 514/80; 514/86; 514/89; 514/90; 514/91; 514/92; 514/211; 514/212; 514/218; 514/222.2; 514/222.5; 514/252; 514/255; 514/256; 514/299; 514/316; 514/318; 514/326; 514/331; 540/460; 540/463; 540/492; 540/524; 544/3; 544/7; 544/316; 544/360; 546/22; 546/125; 546/183; 546/187; 546/188; 546/193; 546/201; 546/207; 546/208; 546/210; 546/212; 546/233; 546/300
[58] Field of Search ............... 546/188, 22, 125, 183, 546/187, 193, 201, 208, 210, 300, 212, 233, 207; 544/3, 316, 360, 7; 540/524, 460, 463, 492; 514/79–80, 86, 89–92, 211–212, 218, 222.2, 222.5, 252, 255–256, 299, 316, 318, 326, 331

[56] References Cited

U.S. PATENT DOCUMENTS

| | | | |
|---|---|---|---|
| 4,064,255 | 12/1977 | Champseix et al. | 424/267 |
| 4,122,255 | 10/1992 | Krapcho | 542/421 |
| 4,243,807 | 1/1981 | Friebe et al. | 546/232 |
| 4,622,331 | 11/1986 | Jozic | 514/331 |
| 5,030,654 | 7/1991 | Barnish | 514/510 |
| 5,064,814 | 11/1991 | Klein et al. | 514/18 |

FOREIGN PATENT DOCUMENTS

| | | |
|---|---|---|
| 352249 | 1/1990 | European Pat. Off. |
| 372486 | 6/1990 | European Pat. Off. |
| 381033 | 8/1990 | European Pat. Off. |
| 384362 | 8/1990 | European Pat. Off. |
| 405537 | 1/1991 | European Pat. Off. |
| 0478328A1 | 4/1992 | European Pat. Off. |
| 0478362A2 | 4/1992 | European Pat. Off. |

Primary Examiner—Marianne M. Cintins
Assistant Examiner—Michael B. Hydorn
Attorney, Agent, or Firm—Paul D. Matukaitis; Melvin Winokur; Richard S. Parr

[57] ABSTRACT

Fibrinogen receptor antagonists of the formula:

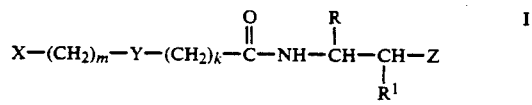

such as

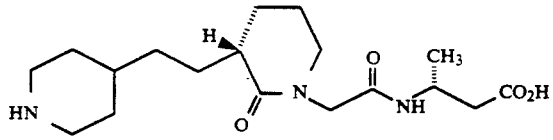

are disclosed for use in inhibiting the binding of fibrinogen to blood platelets and for inhibiting the aggregation of blood platelets.

18 Claims, No Drawings

FIBRINOGEN RECEPTOR ANTAGONISTS FOR INHIBITING AGGREGATION OF BLOOD PLATELETS

CROSS-REFERENCES

This application is a continuation-in-part of U.S. Ser. No. 871,262, filed Apr. 23, 1992, now abandoned; which is a continuation-in-part U.S. Ser. No. 720,357, filed Jun. 25, 1991, now abandoned; which is a continuation-in-part of U.S. Ser. No. 696,893, filed May 7, 1991, now abandoned.

FIELD OF THE INVENTION

This invention relates to the discovery of fibrinogen receptor antagonists of Formula I for use in inhibiting the binding of fibrinogen to blood platelets and inhibiting the aggregation of blood platelets when administered to mammals, preferably humans.

BACKGROUND OF THE INVENTION

The interaction of platelets with the coagulation and fibrinolytic systems in the maintenance of hemostasis may become pathogenic, requiring prevention and treatment. The fibrinogen receptor antagonists of Formula I are useful in treating various diseases related to platelet aggregation and fibrin formation.

An interest in platelet inhibitors has reemerged as a result of a better understanding of the role of platelets and thrombosis in the pathogenesis of vascular disease, including unstable angina, acute myocardial infarction and stroke.

Platelets are cell-like anucleated fragments, found in the blood of all mammals, which participate in blood coagulation. Fibrinogen is a glycoprotein present as a normal component of blood plasma. Fibrinogen participates in platelet aggregation and fibrin formation in the blood clotting mechanism. Platelets are deposited at sites of vascular injury where multiple physiological agonists act to initiate platelet aggregation culminating in the formation of a platelet plug to minimize blood loss. If the platelet plug occurs in the lumen of a blood vessel, normal blood flow is impaired.

Platelet membrane receptors are essential in the process of platelet adhesion and aggregation. Interaction of fibrinogen with a receptor on the platelet membrane complex IIb/IIIa is known to be essential for normal platelet function.

Zimmerman et al., U.S. Pat. No. 4,683,291, describes peptides having utility in the study of fibrinogen-platelet, platelet-platelet, and cell-cell interactions. The peptides are described as having utility where it is desirable to retard or prevent formation of a thrombus or clot in the blood.

Pierschbacher et al., U.S. Pat. No. 4,589,881, describes the sequence of an 11.5 kDal polypeptide fragment of fibronectin which embodies the cell-attachment-promoting activity of fibronectin.

Ruoslahti et al., U.S. Pat. No. 4,614,517, describes tetrapeptides which alter cell-attachment activity of cells to various substrates. FIG. 1 lists the polypeptides that were synthesized by Ruoslahti et al. in "determining the smallest peptide exhibiting cell attachment activity." Ruoslahti et al., U.S. Pat. No. 4,578,079, describes similar tetrapeptides.

Pierschbacher et al., Proc. Natl. Acad. Sci. USA, Vol. 81, pp.5985–5988, October, 1984, describe variants of the cell recognition site of fibronectin that retain attachment-promoting activity. Pierschbacher et. al. further assayed the cell attachment-promoting activities of a number of structures closely resembling the Arg-Gly-Asp-Ser peptide, and found "that the arginine, glycine, and aspartate residues cannot be replaced even with closely related amino acids, but that several amino acids can replace serine without loss of activity."

Ruoslahti et al., Science, Vol. 238, pp. 491–497, Oct. 23, 1987, discuss cell adhesion proteins. They specifically state that "elucidation of the amino acid sequence of the cell-attachment domain in fibronectin and its duplication with synthetic peptides establish the sequence Arg-Gly-Asp (RGD) as the essential structure recognized by cells in fibronectin."

Cheresh, Proc. Natl. Acad. Sci. USA, Vol. 84, pp. 6471–6475, September 1987, describes the Arg-Gly-Asp-directed adhesion receptor involved in attachment to fibrinogen and the von Willebrand Factor.

Adams et al., U.S. Pat. No. 4,857,508, describes tetrapeptides which inhibit platelet aggregation and the formation of a thrombus.

It is, therefore, an object of the present invention to provide fibrinogen receptor antagonists for use in inhibiting the binding of fibrinogen to blood platelets and inhibiting the aggregation of blood platelets. Another aspect of the present invention is to provide novel fibrinogen receptor antagonist compounds. Other objects of the present invention are to provide methods of inhibiting the binding of fibrinogen to blood platelets and inhibiting the aggregation of blood platelets, through the administration of novel fibrinogen receptor antagonist compounds. The above and other objects are accomplished by the present invention in the manner described below.

SUMMARY OF THE INVENTION

The present invention provides fibrinogen receptor antagonist compounds of the formula:

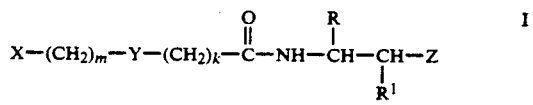

for use in inhibiting the binding of fibrinogen to blood platelets and for inhibiting the aggregation of blood platelets. The above-mentioned compounds can be used in a method of acting upon a fibrinogen receptor which comprises administering a therapeutically effective but non-toxic amount of such compound to a mammal, preferably a human. A pharmaceutical composition comprising a pharmaceutically acceptable carrier and, dispersed therein, an effective but non-toxic amount of such compound is another feature of this invention.

DETAILED DESCRIPTION OF THE INVENTION

Fibrinogen receptor antagonist compounds of Formula I are useful in a method of inhibiting the binding of fibrinogen to blood platelets and for inhibiting the aggregation of blood platelets. Fibrinogen receptor antagonists of this invention are illustrated by compounds having the formula:

Preferred compounds of the present invention have the following formula:

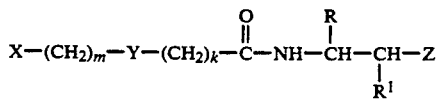

wherein:
X is

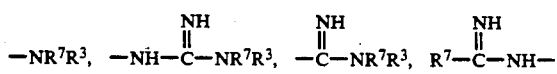

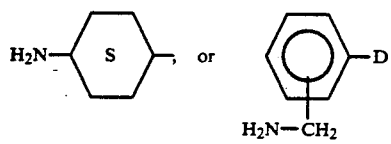

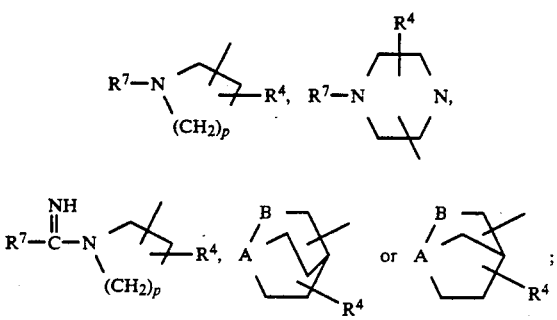

where A=N and B=—CH₂—, or $$A = -CH-$$

and B=NR⁷;
Y is

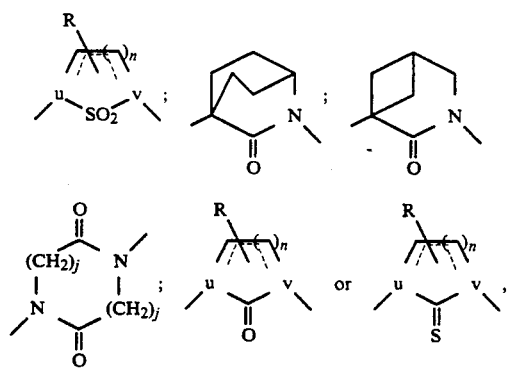

wherein n=0-5 and J=0-3;
Z is —CO₂R²;

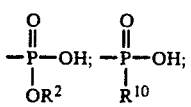

where R¹⁰ is $C_{1-8}$ alkyl, aryl, aryl $C_{1-8}$ alkyl;

u is —CH—, —C—, or —N—;
v is —CH—, —C—, or —N—;
R and R¹ are independently
  hydrogen,
  aryl, wherein aryl is defined as a mono- or polycyclic aromatic system comprised of 5 or 6 membered rings containing 0, 1, 2, 3, or 4 heteroatoms selected from nitrogen, oxygen and sulfur; and phenylene, either unsubstituted or substituted, with one or more groups selected from hydroxyl, fluoro, chloro, bromo, iodo, cyano, trifluoromethyl, $C_{1-3}$ alkoxy, $C_{1-5}$ alkylcarbonyloxy, $C_{1-5}$ alkoxycarbonyl, $C_{1-5}$ alkyl, amino$C_{1-5}$ alkyl, hydroxycarbonyl$C_{1-5}$ alkoxy; alkyl, or hydroxycarbonyl$C_{1-5}$ alkoxy,
  $C_{0-6}$alkyl, either unsubstituted or substituted, with one or more groups selected from fluoro, chloro, bromo, iodo, hydroxyl, $C_{1-5}$alkylcarbonyl($C_{0-8}$alkyl)amino, aryl$C_{1-5}$alkyl carbonyl($C_{0-8}$alkyl)amino, aryloxy, $C_{1-10}$alkoxy, $C_{1-5}$alkoxycarbonyl, $C_{0-5}$alkylaminocarbonyl, $C_{1-5}$ alkylcarbonyloxy, $C_{3-8}$cycloalkyl, aryl, oxo, amino, $C_{1-6}$alkyl, $C_{1-3}$alkylamino, amino$C_{1-3}$alkyl,aryl$C_{0-5}$alkylaminocarbonyl, phenyl$C_{1-3}$ alkylamino, aminocarbonyl$C_{0-4}$alkyl, $C_{1-8}$alkylsulfonyl ($C_{0-8}$alkyl)amino, aryl$C_{0-10}$alkylsulfonyl($C_{0-8}$alkyl)-alkylsulfonyl, $C_{0-8}$alkylsulfonyl, hydroxycarbonyl$C_{0-5}$alkyl, $C_{1-8}$alkyloxycarbonyl($C_{0-8}$alkyl)amino, aryl$C_{0-10}$alkyloxycarbonyl($C_{0-8}$alkyl)amino, $C_{0-8}$ alkylaminocarbonyl($C_{0-8}$ alkyl)amino, aryl$C_{0-8}$alkylaminocarbonyl($C_{0-8}$alkyl)amino, $C_{0-8}$alkylaminocarbonyloxy, aryl$C_{0-10}$alkylaminocarbonyloxy, $C_{0-8}$alkylaminosulfonyl($C_{0-8}$ alkyl)amino, aryl$C_{0-8}$alkylaminosulfonyl($C_{0-8}$alkyl) amino, $C_{0-8}$alkylaminosulfonyl, or ryl$C_{0-8}$alkylaminosulfonyl; provided that the carbon atom to which R or R¹ is attached bear only one heteroatoms;
R² is hydrogen, $C_{1-12}$alkyl, unsubstituted or substituted, with one or more $C_{1-6}$alkyl groups,

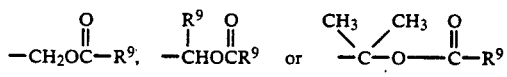

where $R^9=C_{1-6}$alkyl, branched or unbranched, or phenyl, and wherein R⁹, when appearing more than once, can be same or different;
R⁷, R³ and R⁴ are independently
  hydrogen,
  $C_{1-12}$ alkyl, unsubstituted or substituted, with one or more $C_{1-6}$ alkyl groups,
  aryl$C_{0-4}$alkyl, or
  cyano provided that when R⁷ and R³ are independently cyano, X is

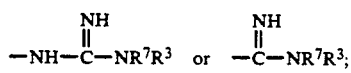

k is 1-4;
m is 1-4;
p is 1-6;
q is 0-2;
or the pharmaceutically acceptable salts thereof, or optical isomers thereof.

More preferred compounds of the present invention have the following formula:

$$X-(CH_2)_m-Y-(CH_2)_k-\overset{O}{\overset{\|}{C}}-NH-\overset{R}{\underset{R^1}{\overset{|}{C}H}}-CH-CO_2R^2$$

wherein:
X is $-NR^7R^3$, $-NH-\overset{NH}{\overset{\|}{C}}-NR^7R^3$, $-\overset{NH}{\overset{\|}{C}}-NR^7R^3$, $R^7-\overset{NH}{\overset{\|}{C}}-NH-$

[structures with $H_2N-$ cyclohexyl-S and phenyl-D with $H_2N-CH_2$]

where D = $-\overset{O}{\overset{\|}{C}}-$, $-S(O)_q-$, or $-O-$;

[structures with $R^7-N$, $(CH_2)_p$, $R^4$]

[bicyclic structures with A, B, $R^4$]

where A=N and B=—CH$_2$—, or

A = —CH—
          | and B=NR$^7$;

Y is

[ring structures with SO$_2$, bicyclic amides with N, O and N, S]

wherein n=0-5
Z is —CO$_2$R$^2$;

$-\overset{O}{\overset{\|}{P}}-OH$;  $-\overset{O}{\overset{\|}{P}}-OH$;
$\underset{OR^2}{|}$     $\underset{R^{10}}{|}$ where R$^{10}$ is C$_{1-8}$ alkyl, aryl, aryl C$_{1-8}$ alkyl;
u is —CH—, —C—, or —N—;

v is —CH—, —C—, or —N—;
R and R$^1$ are independently
  hydrogen,
  aryl, wherein aryl is defined as a mono- or polycyclic aromatic system comprised of 5 or 6 membered rings containing 0, 1, 2, 3, or 4 heteroatoms selected from nitrogen, oxygen and sulfur; and phenylene, either unsubstituted or substituted, with one or more groups selected from hydroxyl, fluoro, chloro, bromo, iodo, cyano, trifluoromethyl, C$_{1-3}$ alkoxy, C$_{1-5}$ alkylcarbonyloxy, C$_{1-5}$ alkoxycarbonyl, C$_{1-5}$ alkyl, aminoC$_{1-5}$ alkyl, hydroxycarbonylC$_{0-5}$ alkyl, or hydroxycarbonylC$_{1-5}$ alkoxy,
  C$_{0-6}$alkyl, either unsubstituted or substituted, with one or more groups selected from fluoro, chloro, bromo, iodo, hydroxyl, C$_{1-5}$alkylcarbonyl(C$_{0-8}$alkyl)amino, arylC$_{1-5}$alkyl carbonyl(C$_{0-8}$alkyl)amino, aryloxy, C$_{1-10}$alkoxy, C$_{1-5}$alkoxycarbonyl, C$_{0-5}$alkylaminocarbonyl, C$_{1-5}$ alkylcarbonyloxy, C$_{3-8}$cycloalkyl, aryl, oxo, amino, C$_{1-6}$alkyl, C$_{1-3}$alkylamino, aminoC$_{1-3}$alkyl, arylC$_{0-5}$alkylaminocarbonyl, phenylC$_{1-3}$ alkylamino, aminocarbonylC$_{0-4}$alkyl, C$_{1-8}$alkylsulfonyl (C$_{0-8}$alkyl)amino, arylC$_{0-10}$alkylsulfonyl(C$_{0-8}$alkyl)-alkylsulfonyl, C$_{0-8}$alkylsulfonyl, hydroxycarbonylC$_{0-5}$alkyl, C$_{1-8}$alkyloxycarbonyl(C$_{0-8}$alkyl)amino, arylC$_{1-10}$alkyloxycarbonyl(C$_{0-8}$alkyl)amino, C$_{0-8}$ alkylaminocarbonyl(C$_{0-8}$ alkyl)amino, arylC$_{0-8}$alkylaminocarbonyl(C$_{0-8}$alkyl)amino, C$_{0-8}$alkylaminocarbonyloxy, arylC$_{0-10}$alkylaminocarbonyloxy, C$_{0-8}$alkylaminosulfonyl(C$_{0-8}$ alkyl)amino, arylC$_{0-8}$alkylaminosulfonyl(C$_{0-8}$alkyl) amino, C$_{0-8}$alkylaminosulfonyl, or arylC$_{0-8}$alkylaminosulfonyl; provided that the carbon atom to which R or R$^1$ is attached bear only one heteroatoms;
R$^2$ is hydrogen, C$_{1-12}$alkyl, unsubstituted or substituted, with one or more C$_{1-6}$alkyl groups, $-CH_2O\overset{O}{\overset{\|}{C}}-R^9$,  $-\overset{R^9}{\underset{|}{C}H}O\overset{O}{\overset{\|}{C}}R^9$  or  $-\overset{CH_3}{\underset{}{C}}\overset{CH_3}{\underset{}{}} -O-\overset{O}{\overset{\|}{C}}-R^9$ where R$^9$=C$_{1-6}$alkyl, branched or unbranched, or phenyl, and wherein R$^9$, when appearing more than once, can be same or different;
R$^7$, R$^3$ and R$^4$ are independently
  hydrogen,
  C$_{1-12}$ alkyl, unsubstituted or substituted, with one or more C$_{1-6}$ alkyl groups,
  arylC$_{0-4}$alkyl, or
  cyano provided that when R$^7$ and R$^3$ are independently cyano, X is $-NH-\overset{NH}{\overset{\|}{C}}-NR^7R^3$  or  $-\overset{NH}{\overset{\|}{C}}-NR^7R^3$;

k is 1-4;
m is 1-4;
p is 1-6;
q is 0-2;
or the pharmaceutically acceptable salts thereof, or optical isomers thereof.

More preferred compounds of the present invention have the following formula:

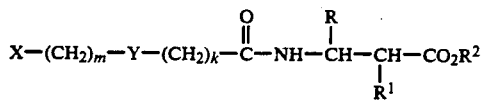

wherein:
X is —NR⁷R³,

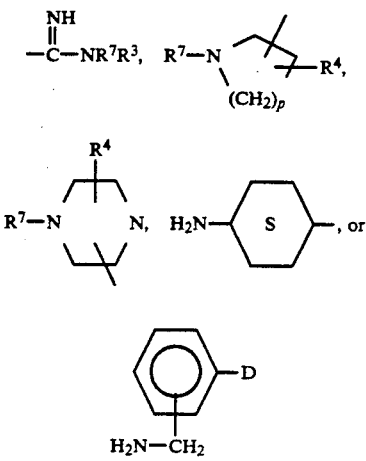

Z is $CO_2R^2$
Y is

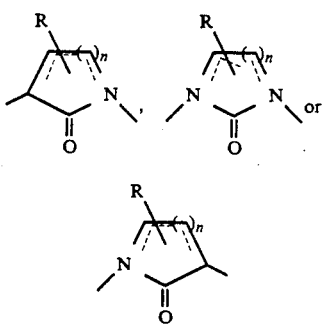

wherein
n is 1, 2 or 3;
R and R¹ are independently chosen from phenyl, thiophene, imidazole, naphthyl, indole, indazole, thionaphthene, either unsubstituted or substituted, with hydroxy, halogen, hydroxycarbonyl $C_{0-5}$ alkyl, $C_{1-3}$alkyl, either unsubstituted or substituted, with one or more groups selected form aryl, aryloxy, $C_{1-10}$ alkoxy, $C_{0-5}$ alkylaminocarbonyl, aryl$C_{0-5}$ alkylaminocarbonyl, hydrogen,
$C_{0-6}$alkyl either unsubstituted or substituted, with one or more groups selected from halogen, hydroxyl, $C_{1-6}$alkylsulfonylamino, aryl $C_{0-6}$alkylsulfonylamino, $C_{1-6}$alkylsulfonyl, aryl$C_{0-6}$alkylsulfonyl, $C_{1-5}$alkylcarbonylamino, aryl$C_{1-5}$alkylcarbonylamino, aryloxy, $C_{1-10}$ alkoxy, $C_{1-5}$alkoxycarbonyl, $C_{0-5}$alkylaminocarbonyl, $C_{1-5}$alkylcarbonyloxy, $C_{3-8}$cycloalkyl, aryl, oxo, amino, alkyl, $C_{1-6}$alkyl, $C_{1-3}$alkylamino, amino$C_{1-3}$ alkyl, aryl$C_{0-5}$ alkylaminocarbonyl, phenyl$C_{1-3}$ alkylamino, aminocarbonyl$C_{0-4}$ alkyl, or hydroxycarbonyl$C_{0-5}$ alkyl, provided that the carbon atom to which R or R¹ is attached bear only one heteroatom, R² is hydrogen, $C_{1-12}$ alkyl, unsubstituted or substituted, with one or more $C_{1-6}$alkyl groups,

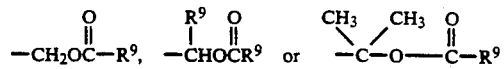

where $R^9 = C_{1-6}$alkyl, branched or unbranched, or phenyl, and wherein $R^9$, when appearing more than once, can be the same or different;
R⁷, R³ and R⁴ are independently hydrogen, or $C_{1-3}$alkyl, unsubstituted or substituted, with one or more $C_{1-6}$alkyl groups;
k is 1–4;
m is 1–4;
q is 0 or 2;
p is 1–3;
or the pharmaceutically acceptable salts thereof, or optical isomers thereof.

Most preferred compounds of the present invention have the following formula:

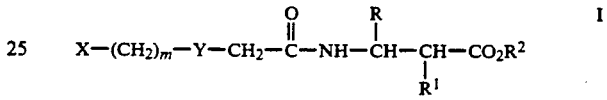

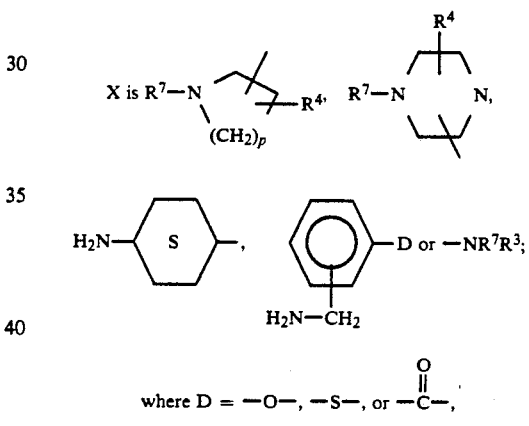

where $D = -O-, -S-,$ or $-\overset{O}{\underset{\|}{C}}-$,

Z is $CO_2R^2$
Y is

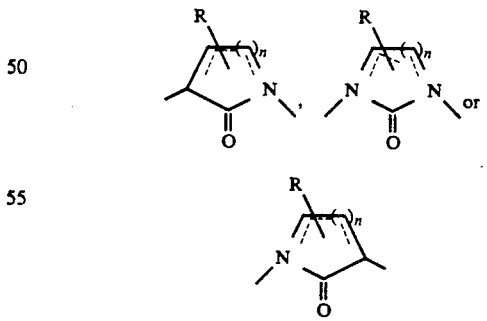

wherein n is 1, 2 or 3;
R and R¹ are independently chosen from phenyl, thiophene, imidazole, naphthyl, indole, indazole, thionaphthene, either unsubstituted or substituted, with hydroxy, halogen, hydroxycarbonyl $C_{0-5}$ alkyl, alkyl, either unsubstituted or substituted, with one or more groups selected form aryl, aryloxy, $C_{1-10}$ alkoxy, $C_{0-5}$ alkylaminocarbonyl, aryl$C_{0-5}$ alkylaminocarbonyl, hydrogen, $C_{0-6}$alkyl, either unsubstituted or substituted, with one or more groups selected from halogen, hydroxyl, $C_{1-5}$alkylcarbonylamino, aryl$C_{1-5}$ alkylcarbonylamino, aryloxy, $C_{1-10}$ alkoxy, $C_{1-5}$alkoxycarbonyl, $C_{0-5}$alkylaminocarbonyl, $C_{1-5}$alkylcarbonyloxy, $C_{3-8}$cycloalkyl, aryl, oxo, amino, $C_{1-6}$alkyl, $C_{1-3}$alkylamino, amino$C_{1-3}$ alkyl, aryl$C_{0-5}$ alkylaminocarbonyl, phenyl$C_{1-3}$ alkylamino, aminocarbonyl$C_{0-4}$ alkyl, or hydroxycarbonyl$C_{0-5}$ alkyl, provided that the carbon atom to which R or $R^1$ is attached bear only one heteroatoms;

$R^2$ is hydrogen;

$R^7$, $R^3$ and $R^4$ are hydrogen;

m is 1–4;

p is 2–4;

or the pharmaceutically acceptable salts thereof, or optical isomers thereof.

This invention includes the following abbreviation designations; Bn, benzyl; NMM, N-methylmorpholine; HOBt, 1-hydroxybenzotriazole; EDC, 1-(3-dimethylaminopropyl)-3-ethylcarbodiimidehydrochloride; DMF, dimethylformamide; BOC, tert-butyloxycarbonyl; pTSA, para-toluenesulfonic acid; DMS, dimethylsulfide; TFA, trifluoroacetic acid; THF, tetrahydrofuran; TBDMS, tert-butyldimethylsilyl.

The pharmaceutically acceptable salts of the compounds of Formula I include the conventional non-toxic salts or the quarternary ammonium salts of the compounds of Formula I formed, e.g., from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the compounds of Formula I which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

The pharmaceutically acceptable salts of the acids of Formula I are also readily prepared by conventional procedures such as treating an acid of Formula I with an appropriate amount of a base, such as an alkali or alkaline earth metal hydroxide e.g. sodium, potassium, lithium, calcium, or malgnesium, or an organic base such as an amine, e.g., dibenzylethylenediamine, trimethylamine, piperidine, pyrrolidine, benzylamine and the like, or a quaternary ammonium hydroxide such as tetramethylammonium hydroxide and the like.

The compounds of Formula I are useful in inhibiting the binding of fibrinogen to blood platelets, inhibiting aggregation of blood platelets, treatment of thrombus formation or embolus formation, in the prevention of thrombus formation or embolus formation, and in the mediation of cell-cell fusion events, such as sperm-egg fusion, resulting in mammalian fertilization inhibition. These compounds are useful as pharmaceutical agents for mammals, especially for humans. The compounds of this invention may be administered to patients where prevention of thrombosis by inhibiting binding of fibrinogen to the platelet membrane glycoprotein complex IIb/IIIa receptor is desired. Compounds of this invention may also be used to prevent or modulate the progress of myocardial infarction, unstable angina and thrombotic stroke, in either acute or chronic settings. In addition, they may be useful in surgery on peripheral arteries (arterial grafts, carotid endarterectomy) and in cardiovascular surgery where manipulation of arteries and organs, and/or the interaction of platelets with artificial surfaces, leads to platelet aggregation and consumption. The aggregated platelets may form thrombi and thromboemboli. Compounds of this invention may be administered to surgical patients to prevent the formation of thrombi and thromboemboli.

Extracorporeal circulation is routinely used for cardiovascular surgery in order to oxygenate blood. Platelets adhere to surfaces of the extracorporeal circuit. Adhesion is dependent on the interaction between GPIIb/IIIa on the platelet membranes and fibrinogen adsorbed to the surface of the circuit. (Gluszko et al., Amer. J. Physiol., 1987, 252:H, pp 615–621). Platelets released from artificial surfaces show impaired hemostatic function. Compounds of this invention may be administered to prevent adhesion.

Other applications of these compounds include prevention of platelet thrombosis, thromboembolism, reocclusion, and restenosis during and after thrombolytic therapy and prevention of platelet thrombosis, thromboembolism, reocclusion and restenosis after angioplasty of coronary and other arteries and after coronary artery bypass procedures.

The compounds of Formula I may be administered to mammals, preferably in combination with pharmaceutically-acceptable carriers or diluents, optionally with known adjuvants such as alum, in a pharmaceutical composition which is non-toxic and in a therapeutically effective amount, according to standard pharmaceutical practice. The compounds can be administered orally or parenterally, including intravenous, intramuscular, intraperitoneal, trans-dermal, subcutaneous and topical administration.

For oral use of a fibrinogen receptor antagonist according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added.

For intramuscular, intrapertioneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The present invention also encompasses a pharmaceutical composition useful in the treatment and prevention of diseases related to platelet aggregation, fibrin formation, and thrombus and embolus formation, comprising the administration of a therapeutically effective but non-toxic amount of the compounds of Formula I, with or without pharmaceutically acceptable carriers or diluents.

Compositions of this invention include fibrinogen receptor antagonist compounds of this invention in combination with pharmacologically acceptable carriers, e.g. saline, at a pH level e.g. 7.4, suitable for achieving inhibition of platelet aggregation. The compositions may also be combined with anticoagulants such as heparin or warfarin. The compositions may also be combined with thrombolytic agents such as plasminogen activators or streptokinase in order to inhibit platelet aggregation in more acute settings. The composition may further be combined with antiplatelet agents such as aspirin. The compositions are soluble in an aqueous medium, and may therefore be effectively administered in solution.

When a compound according to Formula I is used as a fibrinogen receptor antagonist in a human subject, the daily dosage will normally be determined by the prescribing physician with the dosage generally varying according to the age, weight, and response of the individual patient, as well as the severity of the patients symptoms.

In one exemplary application, a suitable amount of compound is administered orally to a heart attack victim before or subsequent to angioplasty. Administration occurs before or subsequent to angioplasty, and is in an amount sufficient to inhibit platelet aggregation, e.g. an amount which achieves a steady state plasma concentration of between about 0.01–100 $\mu$M preferably between about 0.01–10 $\mu$M.

The present invention also includes a pharmaceutical composition comprising compounds of the present invention in combination with tissue type plasminogen activator or streptokinase. The invention also includes a method for promoting thrombolysis and preventing reocclusion in a patient which comprises administering to the patient an effective amount of compositions of the invention.

The present invention provides a method of inhibiting the binding of fibrinogen to blood platelets, inhibiting aggregation of blood platelets, treating thrombus formation or embolus formation, and in preventing thrombus formation or embolus formation in a mammal, comprising the administration of a therapeutically effective but non-toxic amount of the compounds of this invention, with or without pharmaceutically acceptable carriers or diluents.

The present invention still further provides a method of inhibiting the binding of fibrinogen to blood platelets, inhibiting aggregation of blood platelets, treating thrombus formation or embolus formation, and in preventing thrombus formation or embolus formation in a mammal, comprising the administration of a therapeutically effective but non-toxic amounts of the compounds of this invention in combination with thrombolytic agents, such as tissue plasminogen activators or streptokinase, anticoagulants such as heparin or warfarin, or antiplatelet agents such as aspirin, with or without pharmaceutically acceptable carriers or diluents.

The following compounds and associated $IC_{50}$ values (concentrations which inhibit aggregation by 50% relative to a control lacking the compound) are exemplary of the invention.

| Compound | $IC_{50}$ |
|---|---|
| [structure] | 0.097 $\mu$M |
| [structure] | 0.031 $\mu$M |
| [structure] | 100 $\mu$M |
| [structure] | 0.016 $\mu$M |

-continued

| Compound | IC$_{50}$ |
|---|---|
| (structure: piperidine-ethyl-piperidinone-CH$_2$C(O)NH-CH(CH$_3$)-CH$_2$-COOH) | 1.4 μM |
| (structure: piperidine-ethyl-piperidinone-CH$_2$C(O)NH-C(CF$_3$)-CH$_2$-COOH) | 0.2 μM |
| (structure: piperidine-ethyl-pyrrolidinone-CH$_2$C(O)NH-CH(CH$_3$)-CH$_2$-COOH) | 0.037 μM |
| (structure: piperidine-ethyl-piperidinone-CH$_2$C(O)NH-CH(CH$_3$)-CH$_2$-CO$_2$H) | 7.8 μM |
| (structure: piperidine-ethyl-piperidinone-CH$_2$C(O)NH-CH(CH$_3$)-CH$_2$-COOH) | 0.011 μM |
| (structure: piperidine-ethyl-piperidinone-CH$_2$C(O)NH-CH(CH$_2$CH$_3$)-CH$_2$-COOH) | 0.03 μM |
| (structure: piperidine-ethyl-piperidinone-CH$_2$C(O)NH-CH$_2$-CH$_2$-COOH) | 0.18 μM |
| (structure: piperidine-ethyl-pyrrolidinone-CH$_2$C(O)NH-CH(CH$_2$CH$_2$Ph)-CH$_2$-COOH) | 0.056 μM |

-continued

| Compound | IC$_{50}$ |
|---|---|
| [structure] | 17 μM |
| [structure] | 0.55 μM |
| [structure] | 0.096 μM |
| [structure] | 0.14 μM |
| [structure] | 8.1 μM |
| [structure] | 0.84 μM |
| [structure] | 0.27 μM |
| [structure] | 0.028 μM |
| [structure] | 3.7 μM |

| Compound | IC$_{50}$ |
|---|---|
| 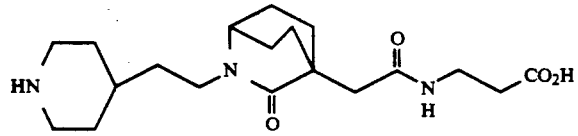 | 0.83 μM |
| 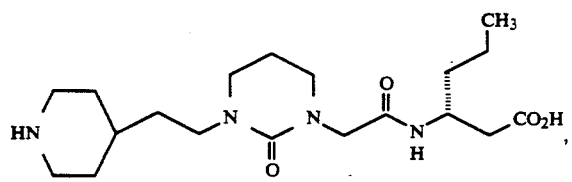 | 0.58 μM |
| 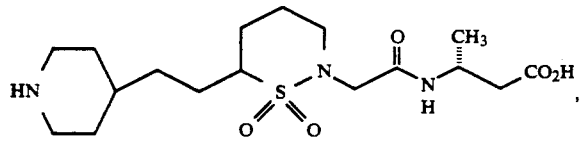 | 0.2 μM |
| 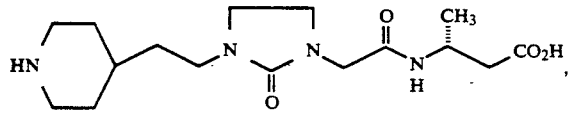 | 0.39 μM |
| 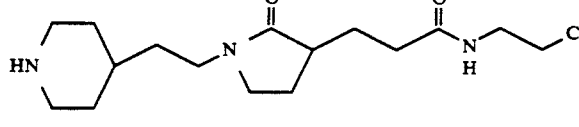 | 0.42 μM |
| 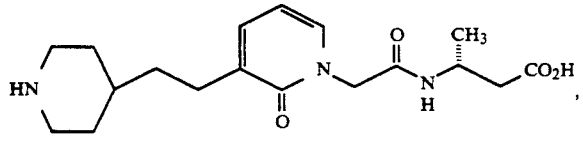 | 3.1 μM |
| 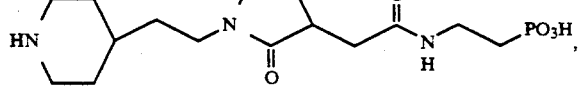 | 0.55 μM |

Compounds of the invention can be prepared according to one of the following general procedures:

SCHEME I

An aryl or alkyl alcohol is protected if needed and is oxidized to the corresponding aldehyde via oxalyl chloride/DMSO, pyridinium chlorochromate or similar reagent. Typically, these oxidations are carried out in halocarbon solvents such as CH$_2$Cl$_2$ at −78° to room temperature for 0.5–6 hrs. Olefination of the resulting aldehyde with a carboalkoxymethylene phosphorane proceeds to give the desired unsaturated ester. Typically, this reaction is run in halocarbon solvents such as CH$_2$Cl$_2$ at 0°–60° for 1–18 hours. Treatment of this ester with a chiral amine such as R-(+)-α-methylbenzylamine provides a diastereomeric mixture of amines that can be separated typically by column chromatography.

SCHEME 2

An aminoalkanol is protected on N with a BOC, or similarly suitable group such as CBZ, FMOC, etc., and converted to the alkyl halide, typically the iodide. Ph$_3$P and iodine are typically used for this purpose and the reaction is run in aromatic solvents such as benzene or toluene in halocarbons such as CH$_2$Cl$_2$ at 0°–50° for 5 minutes to 10 hrs. Formation of an alkyl azide is effected by treatment with NaN$_3$ or similar azide transfer agent, and this azide is catalytically reduced to the corresponding amine in alcohol solvents (EtOH, CH$_3$OH) at room temperature over the course of 0.5–10 hrs.

SCHEME 3

Alkylation of cyclic amide or urea intermediates occurs in the presence of a suitable base, such as LiN(TMS)$_2$ or simple amines such as EtN(i-Pr)$_2$ and an appropriate alkylating agent such as an alkyl in alkyl iodide or a bromide such as ethyl bromoacetate. Disubstitution in the intermediate is effected by repetition of the deprotonation/alkylation sequence. When an allyl reagent is used to alkylate, subsequent oxidation with RuCl$_3$/NaIO$_4$ or KMnO$_4$ or other suitable reagent provides the terminal carboxylic acid. This acid may then be coupled via an amide bond with C-terminal chiral or achiral amines to provide further intermediates. Typically, coupling reactions are carried out in DMF or halocarbon solvents such as $CH_2Cl_2$ utilizing standard reagents such as DCC, EDC, i-butyl chloroformate and the like. Final de-protection of intermediates typically involves base catalyzed hydrolysis of esters and acid catalyzed N-deprotection.

The compounds of Formula I are prepared according to the reaction schemes set forth below. Compound 1, 3-indolepropanol, is commercially available from Aldrich Chemical.

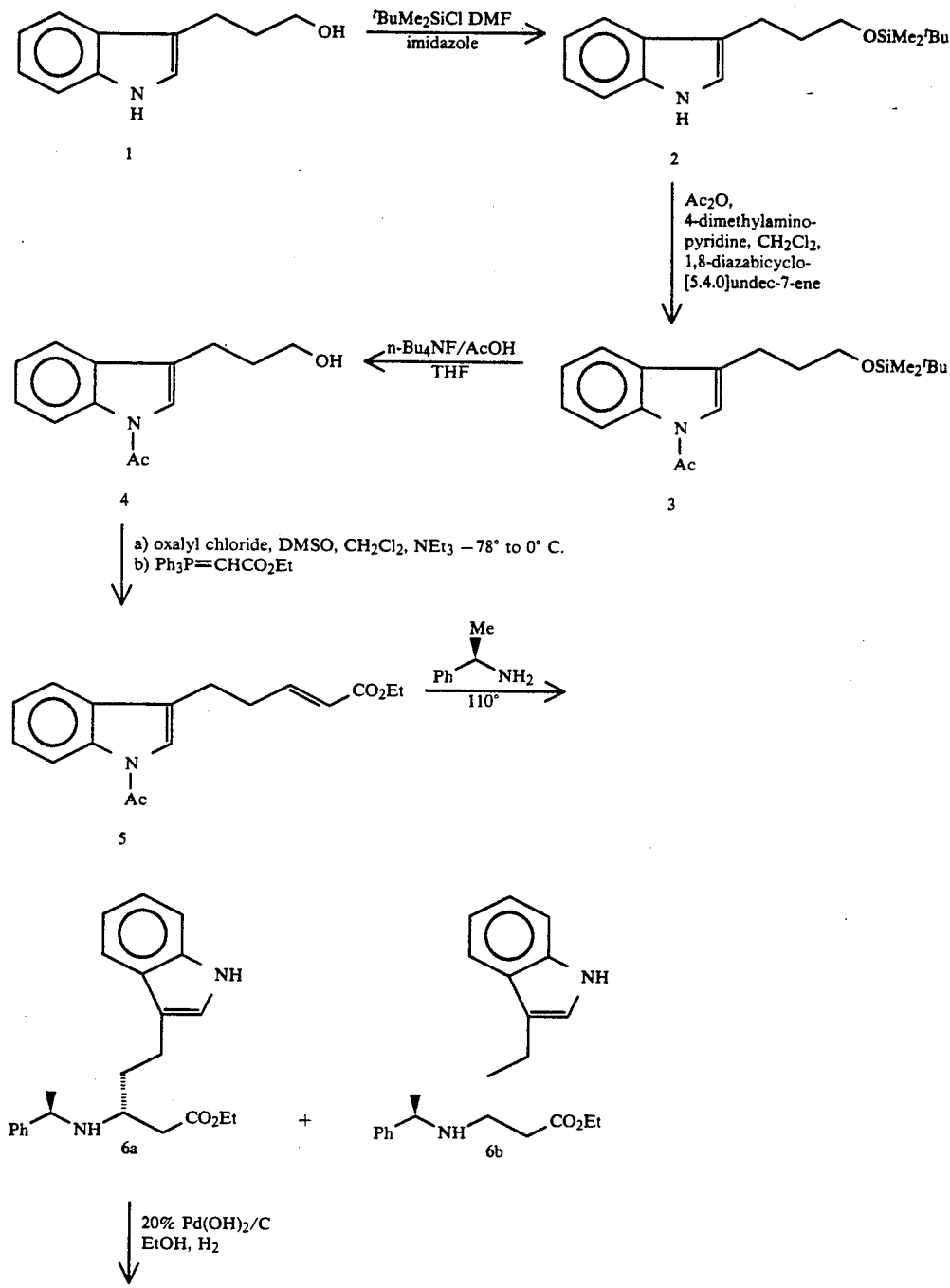

-continued
SCHEME 1
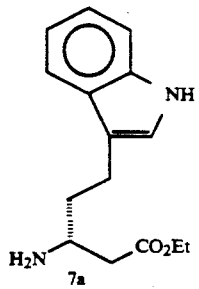
Compound 8 is commercially available from American Tokyo Kansei, Inc.
SCHEME 2
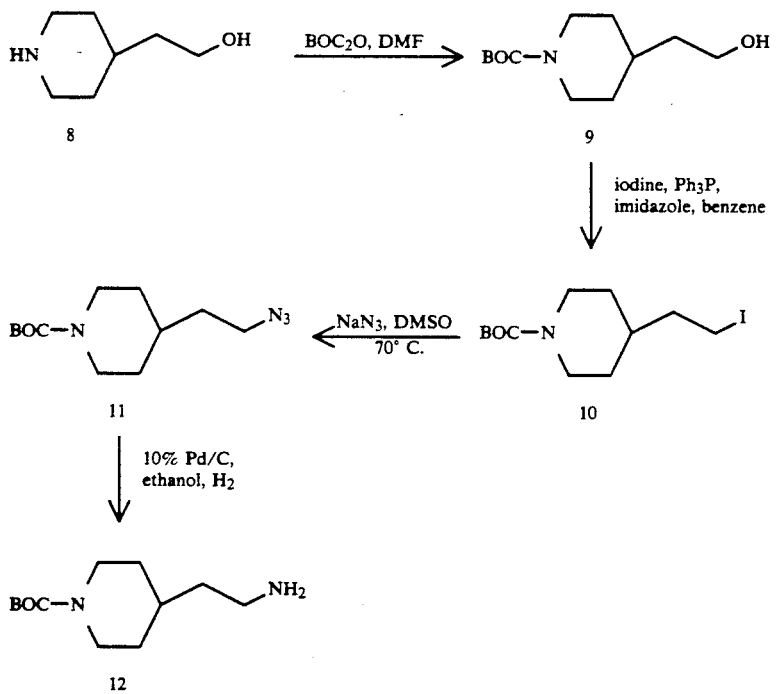
SCHEME 3
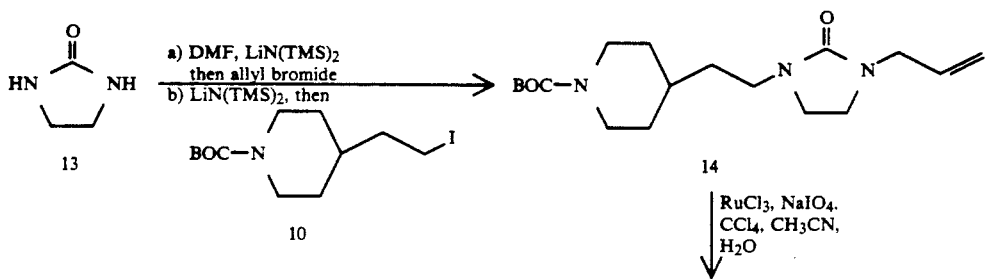

-continued
SCHEME 3
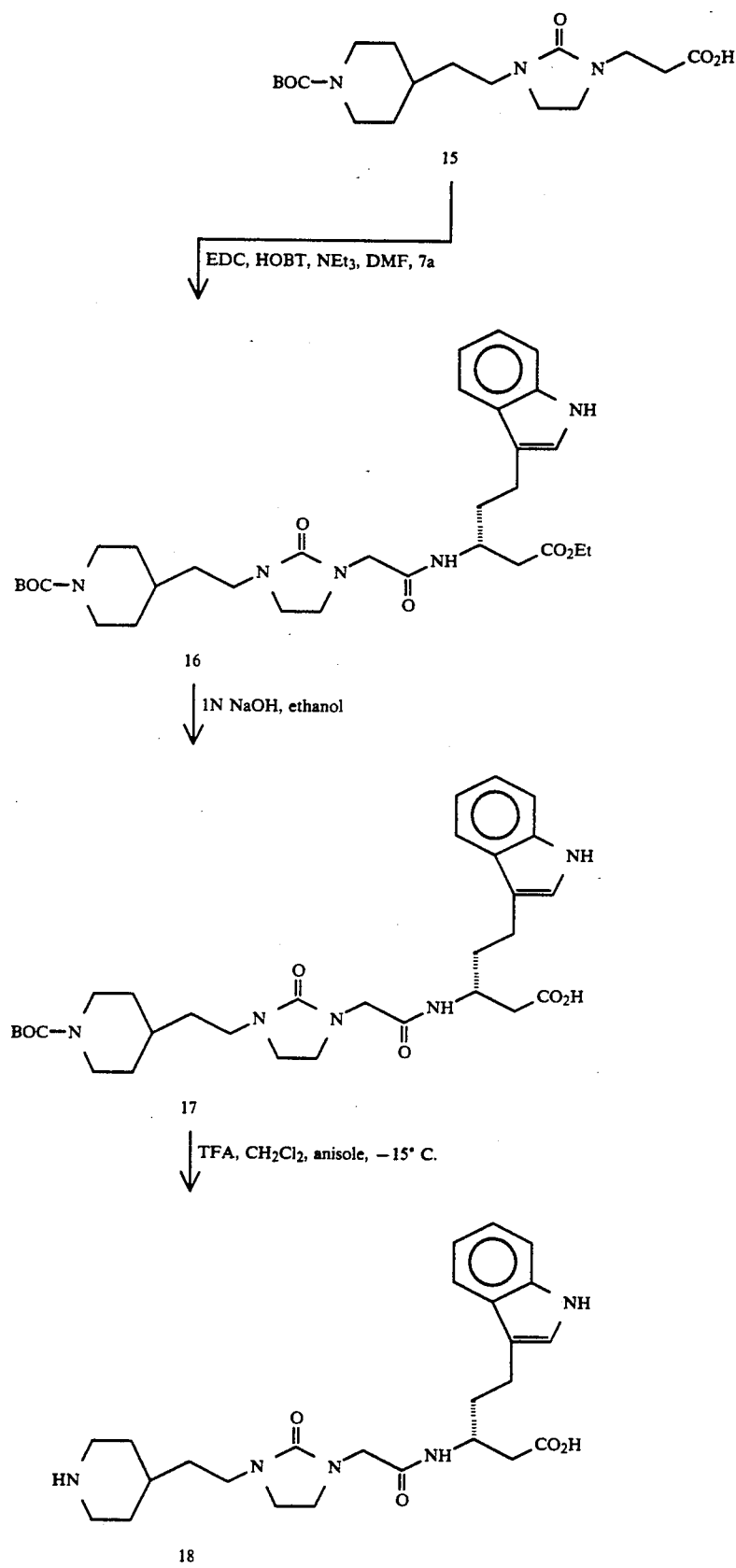

SCHEME 4
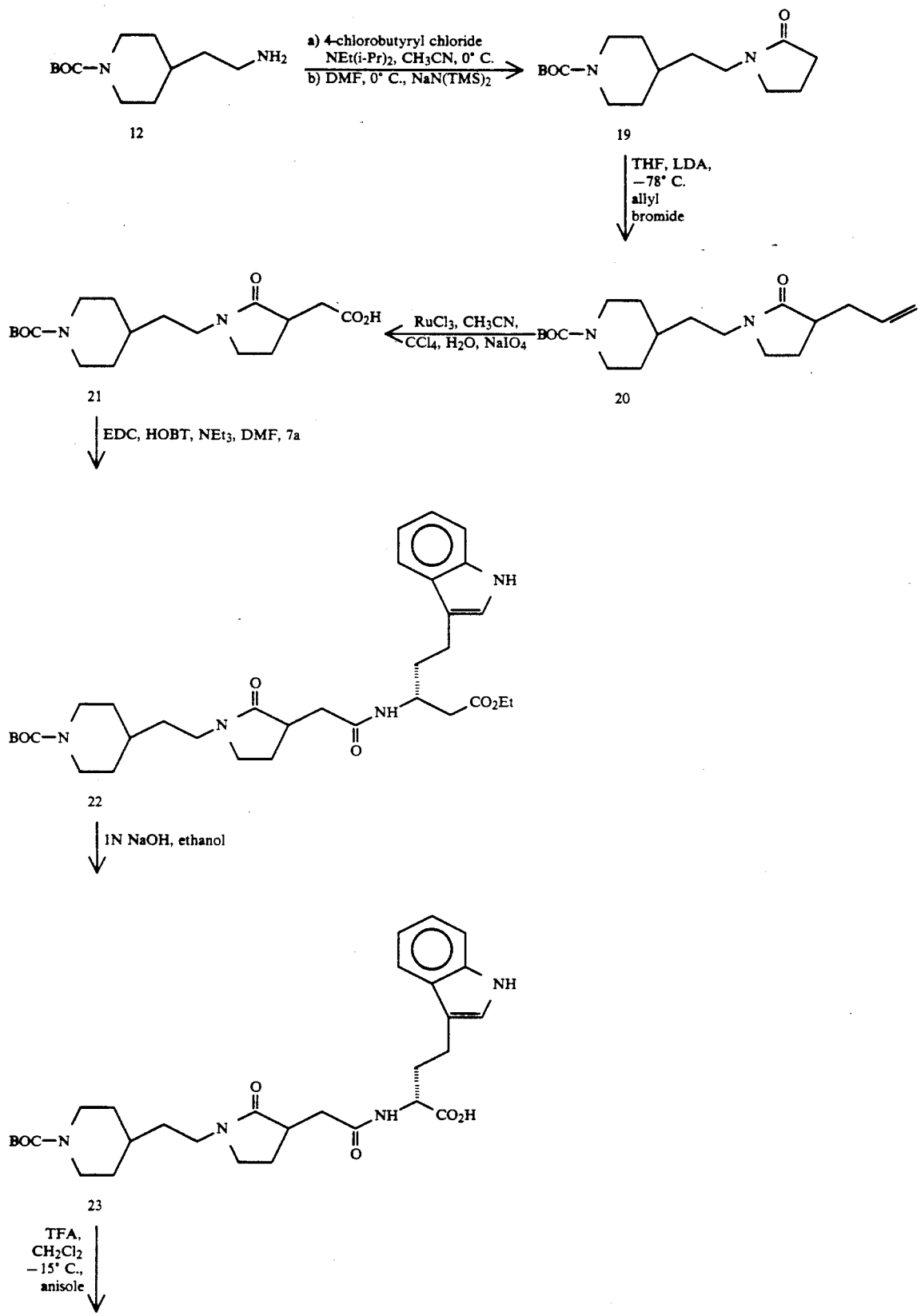

-continued
SCHEME 4
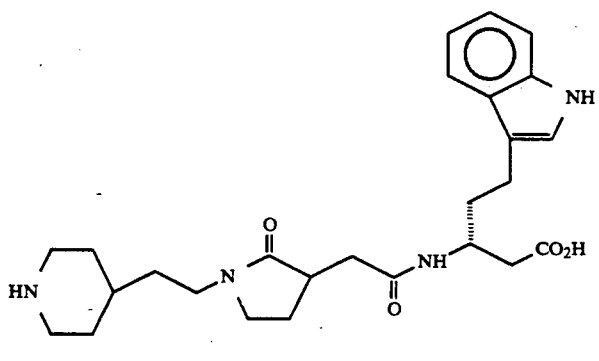
SCHEME 5
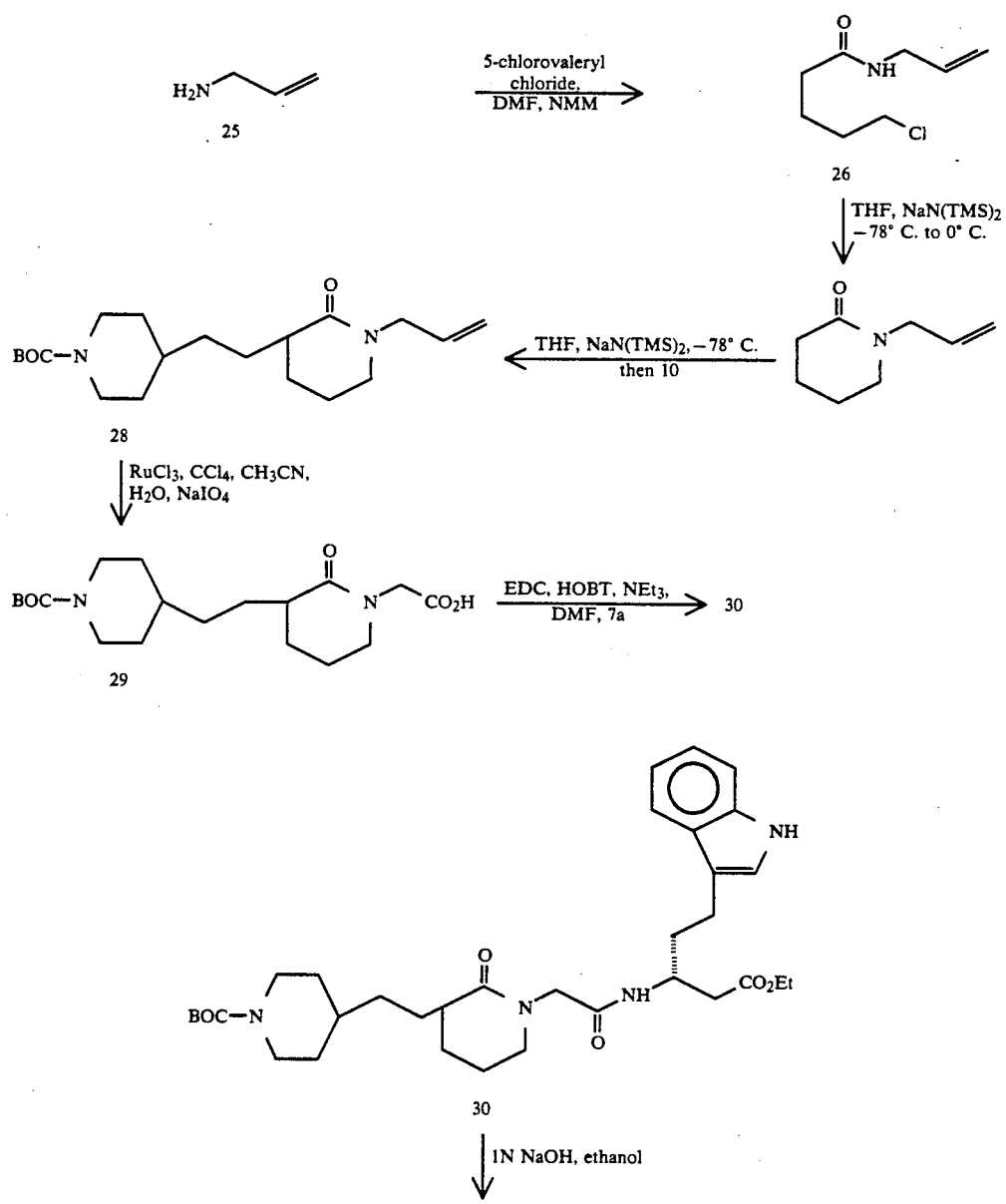

-continued
SCHEME 5
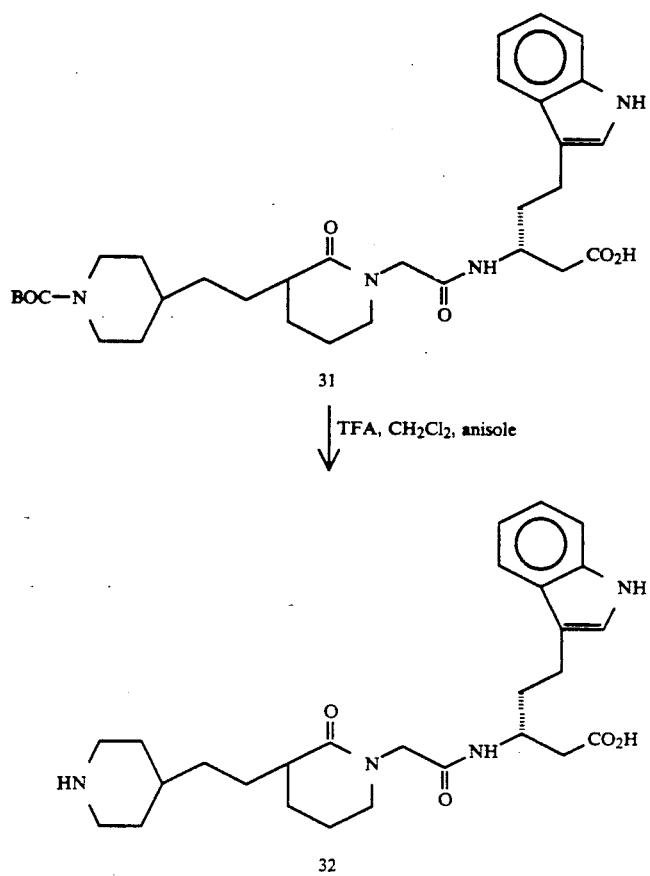
SCHEME 6
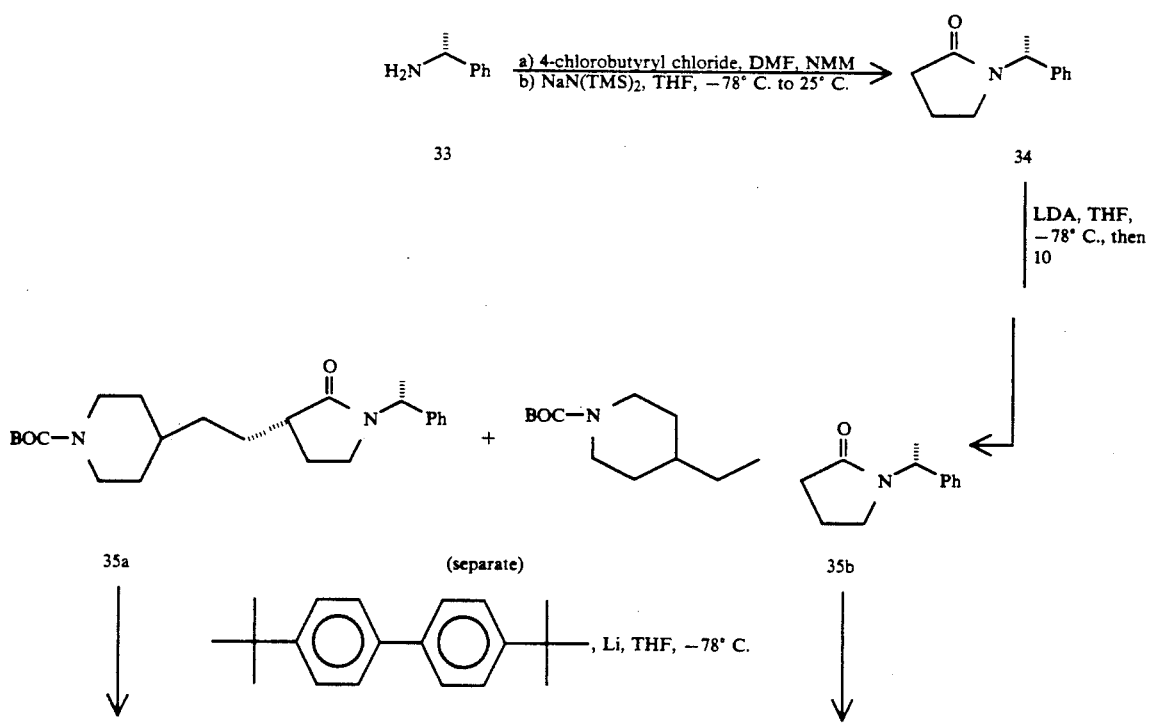

-continued
SCHEME 6
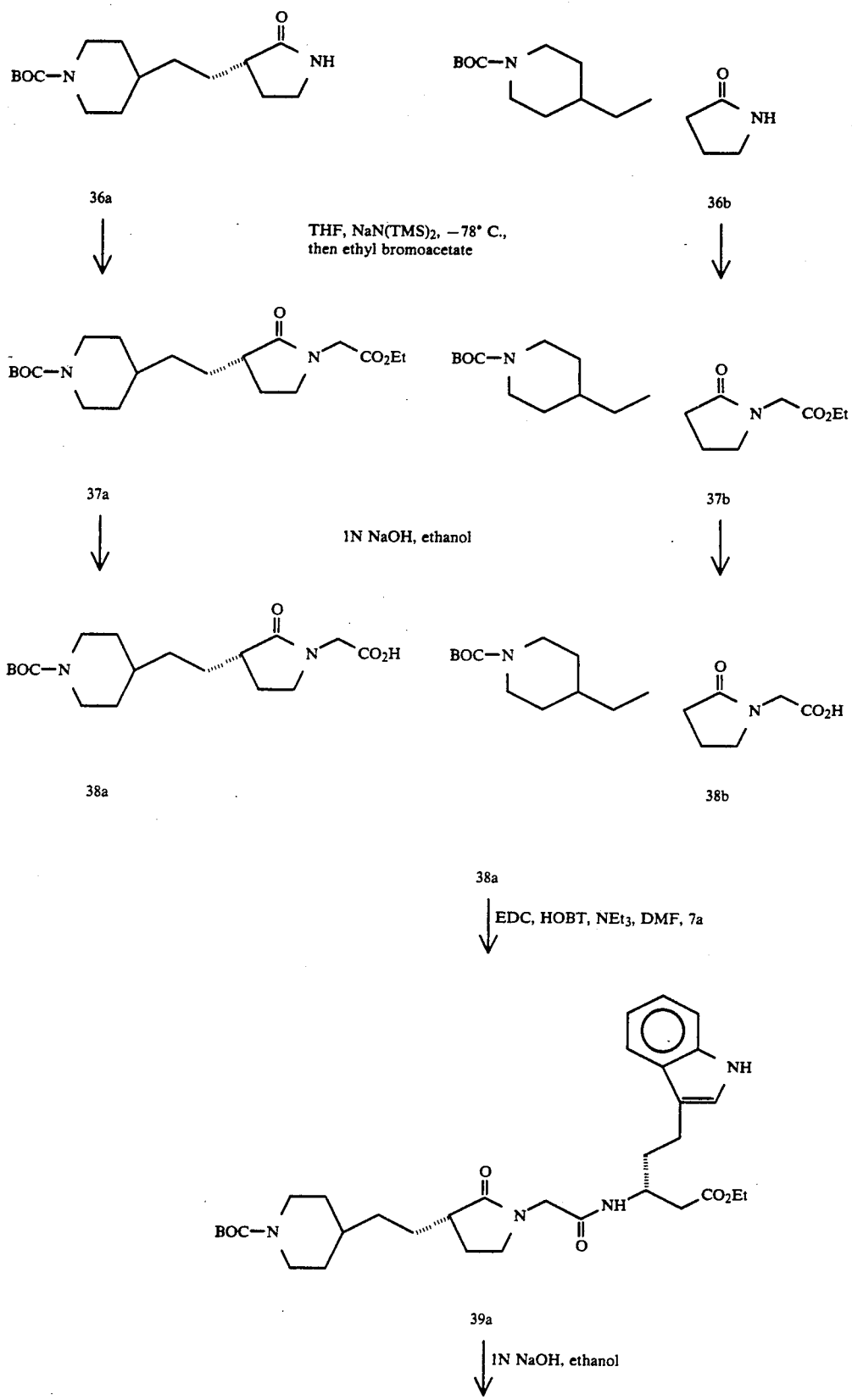

-continued
SCHEME 6
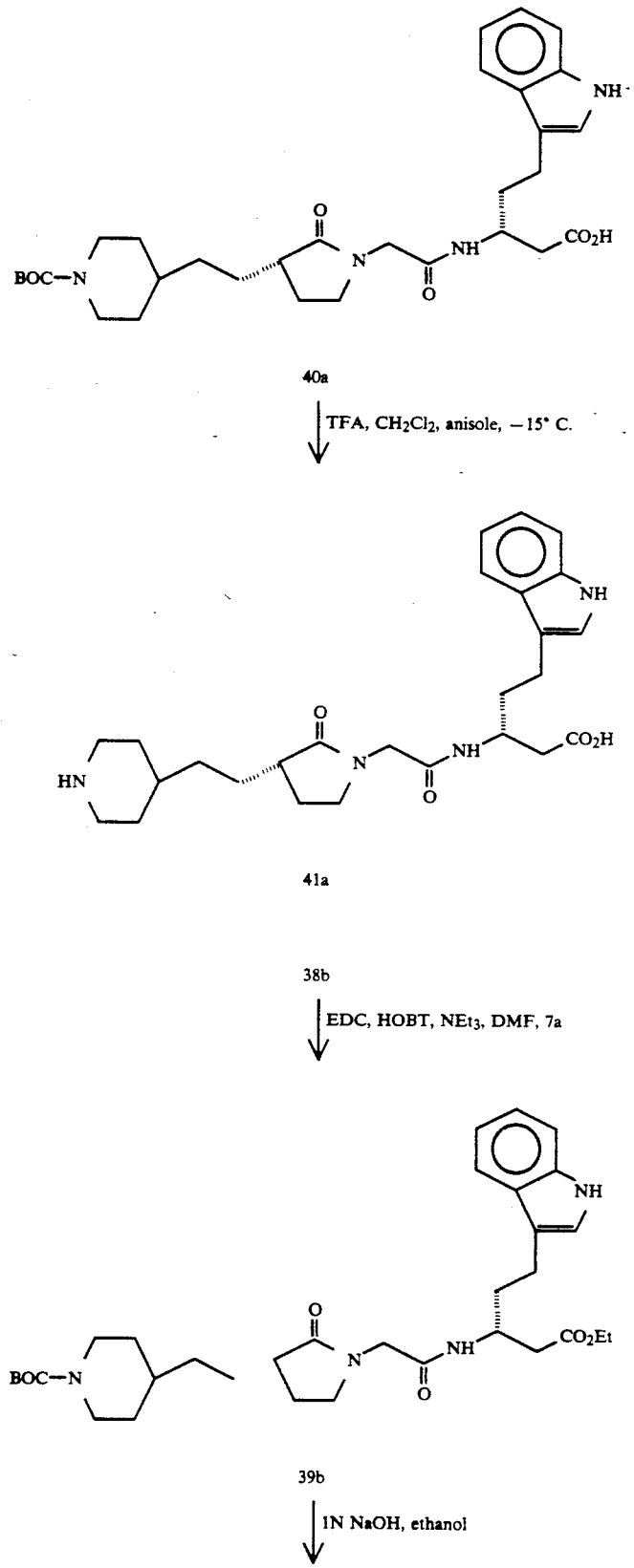
40a
↓ TFA, CH₂Cl₂, anisole, −15° C.
41a
38b
↓ EDC, HOBT, NEt₃, DMF, 7a
39b
↓ 1N NaOH, ethanol -continued
SCHEME 6
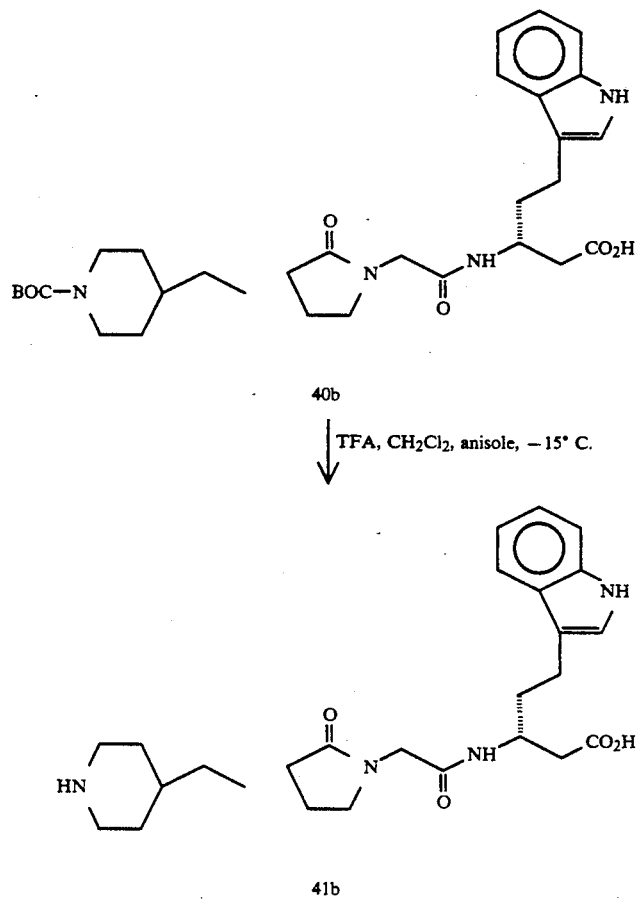
SCHEME 7
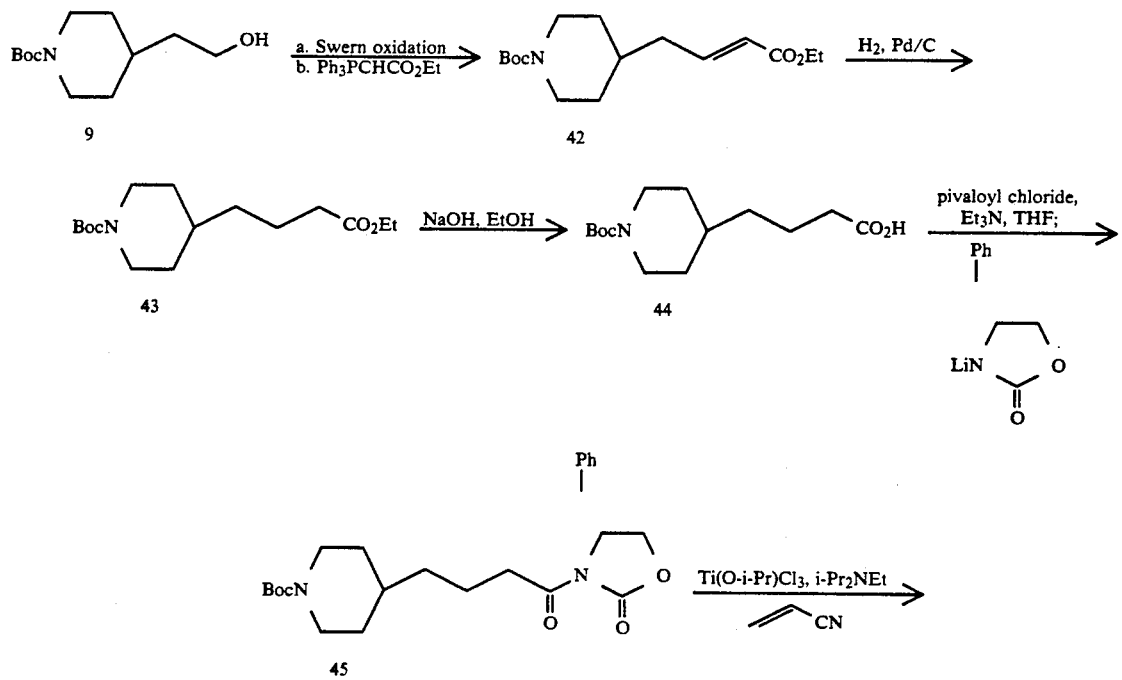

-continued
SCHEME 7
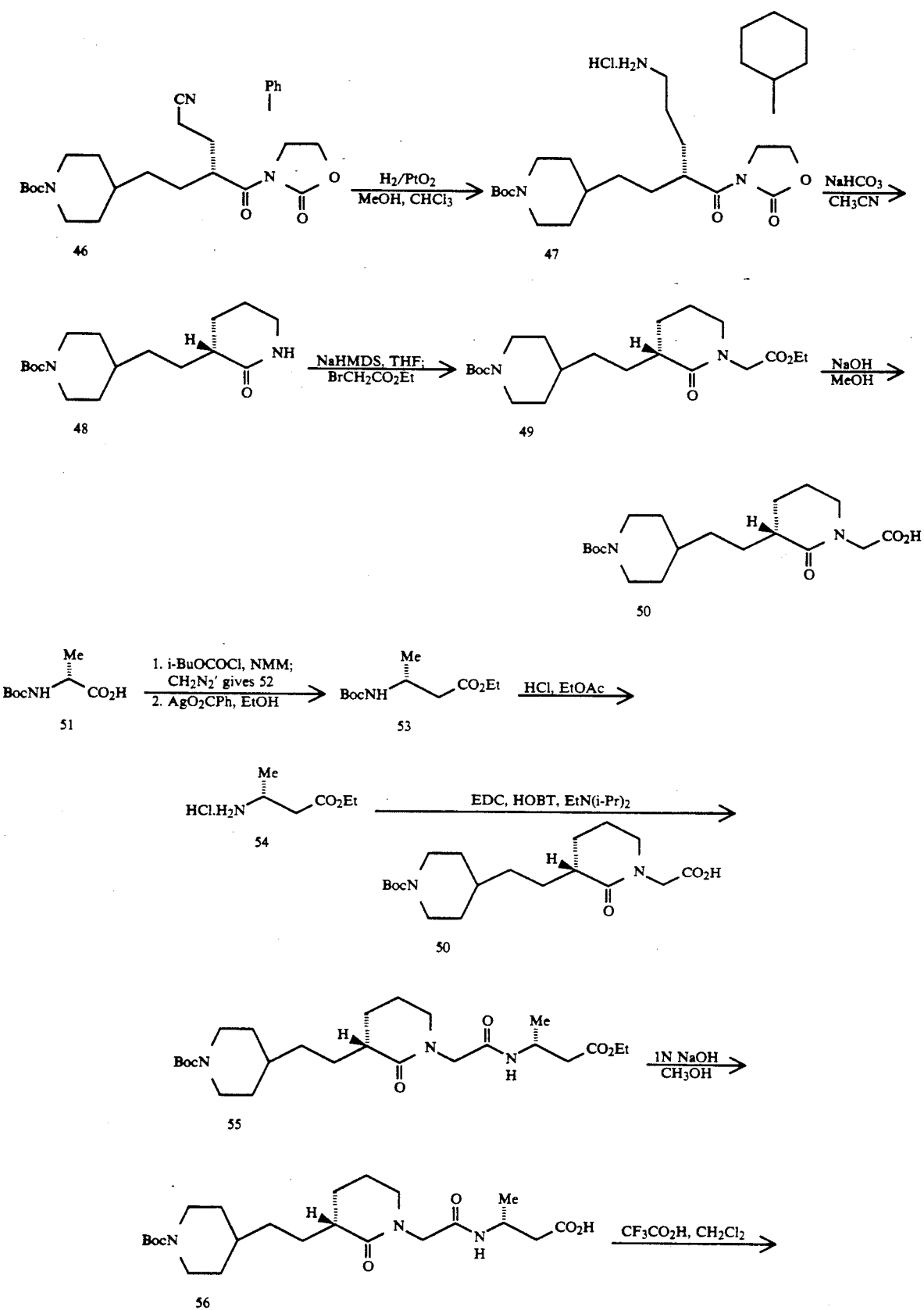

5,281,585
-continued
SCHEME 7
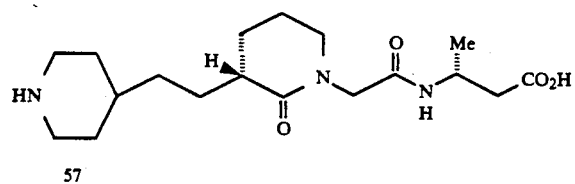
57
SCHEME 8
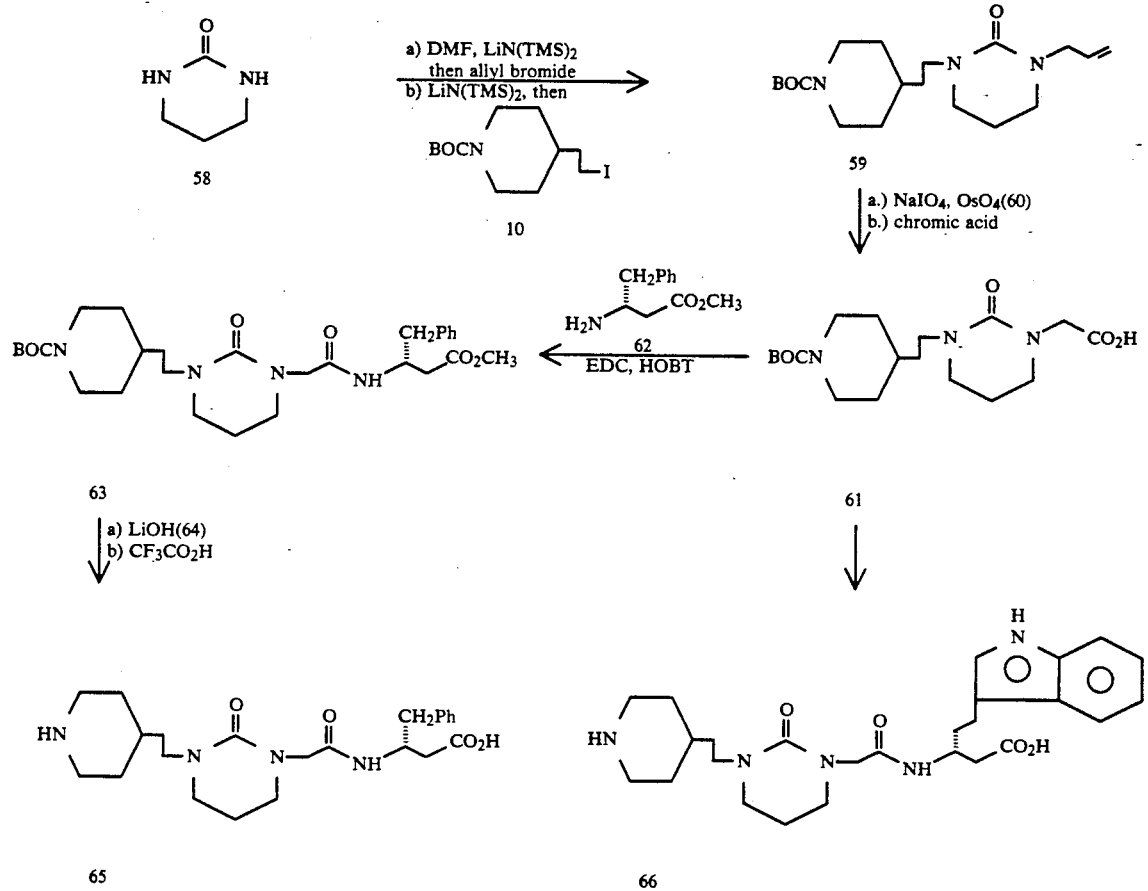
SCHEME 9
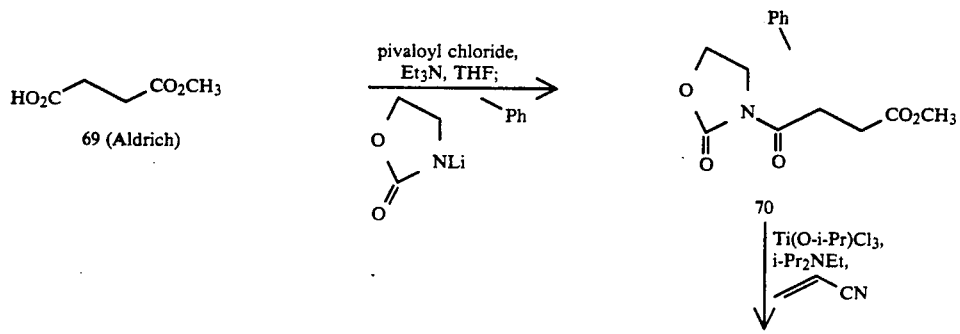

5,281,585
-continued
SCHEME 9
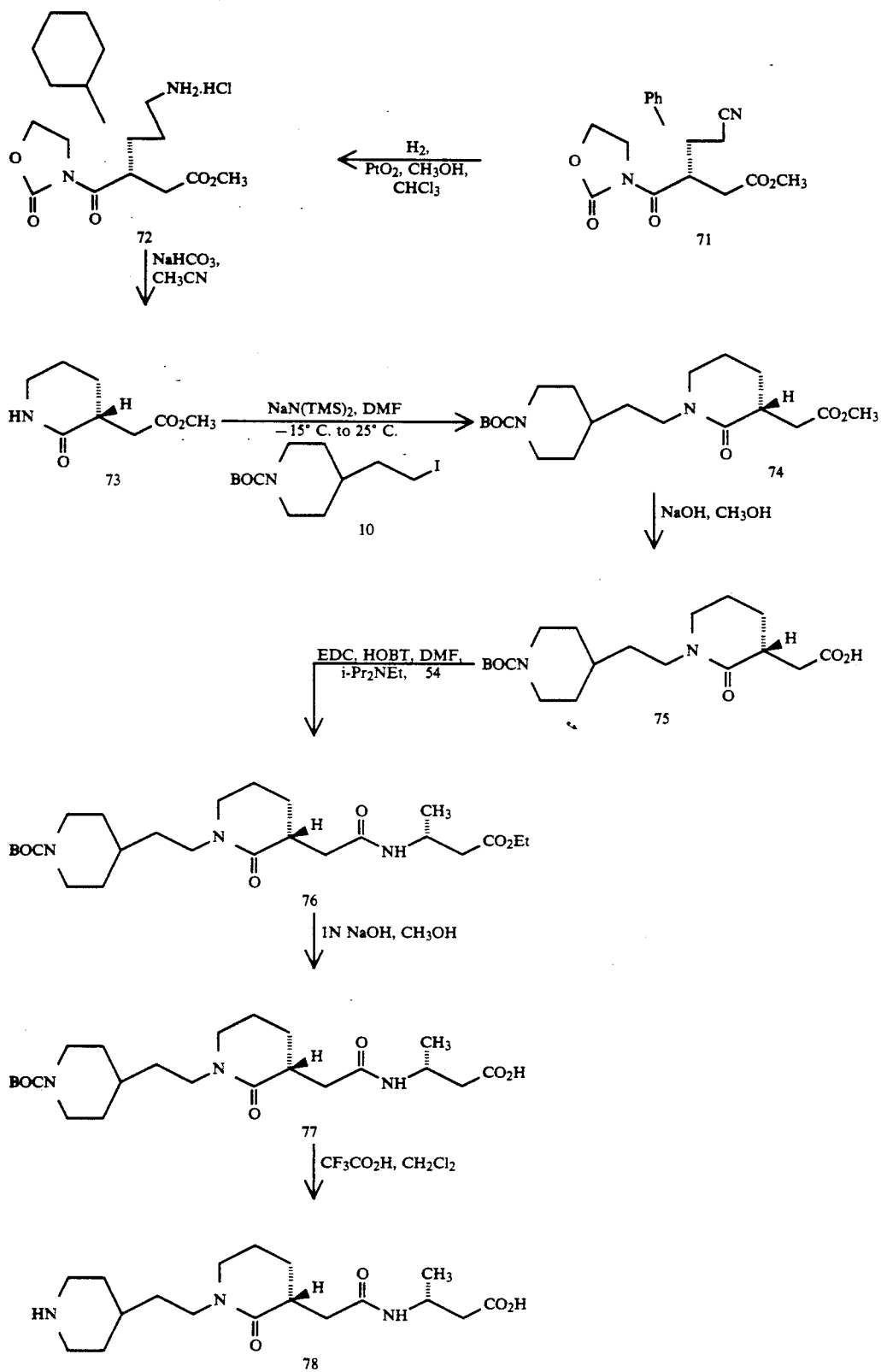

SCHEME 10
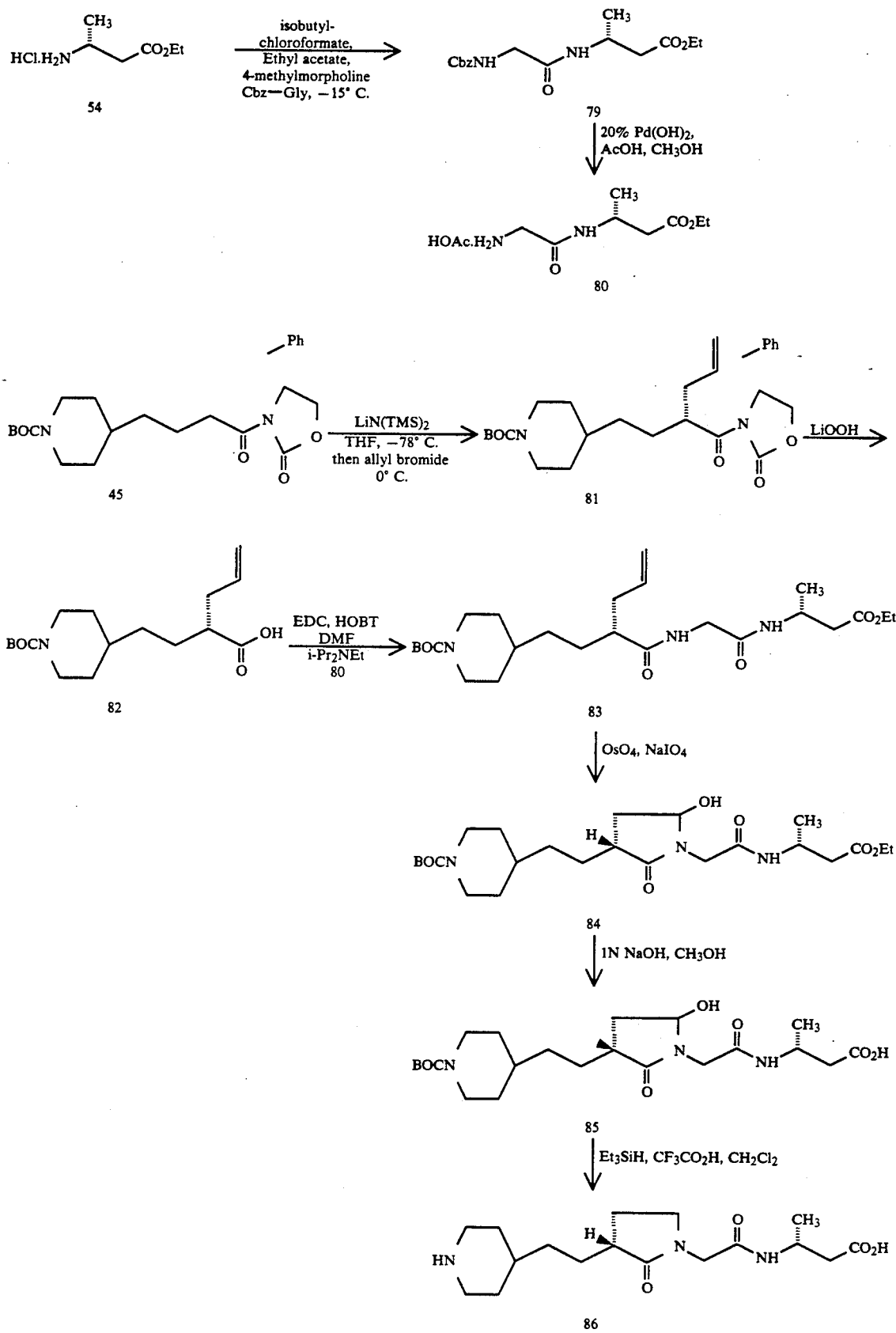

SCHEME 11
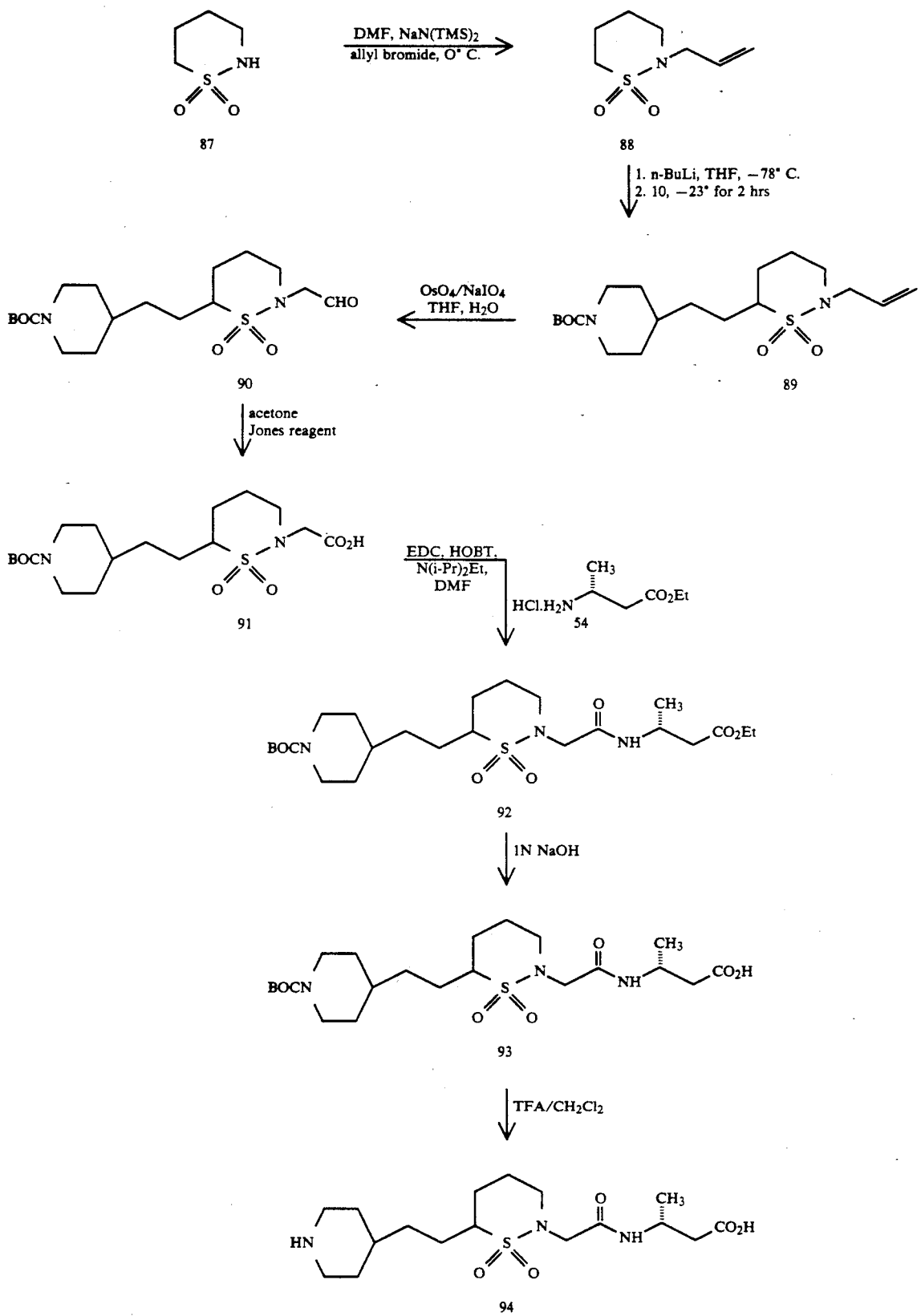

SCHEME 12
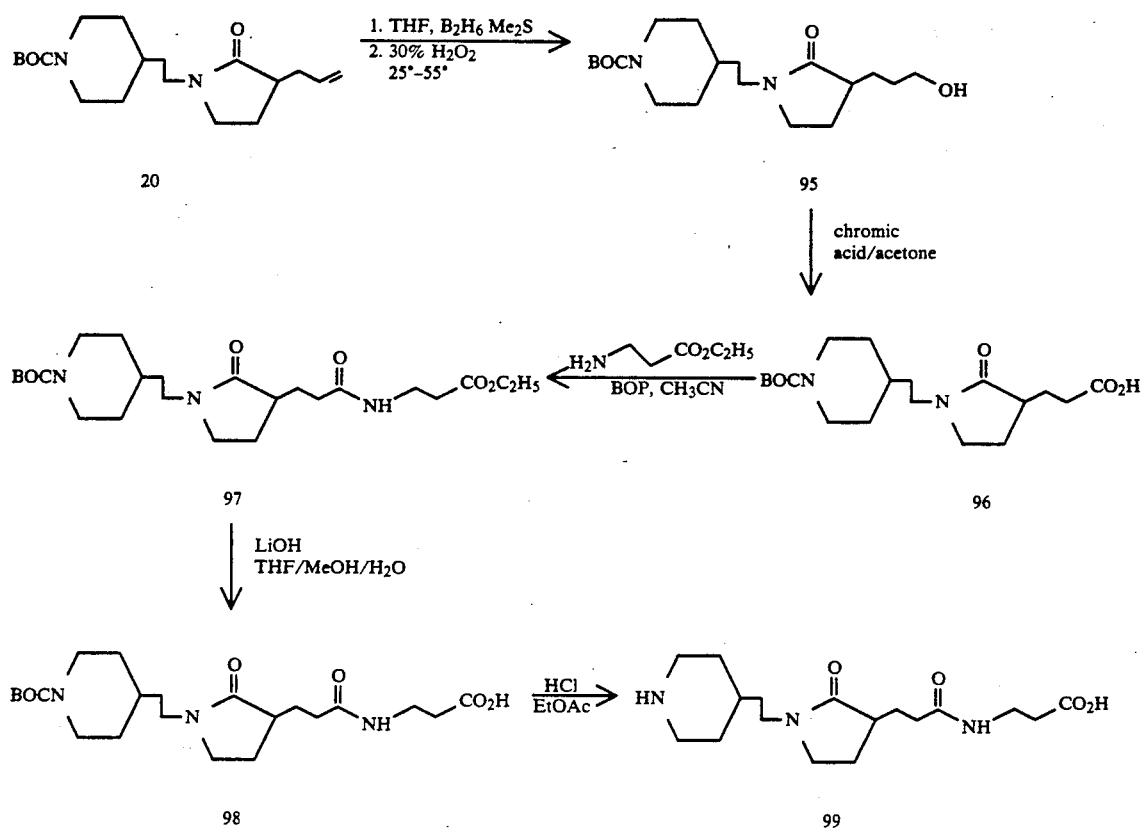
SCHEME 13
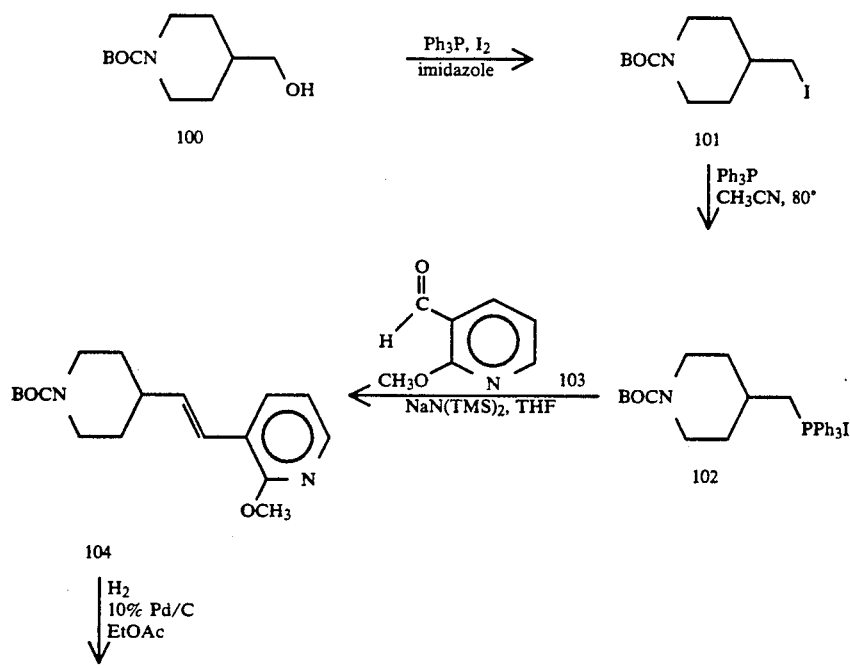

-continued
SCHEME 13
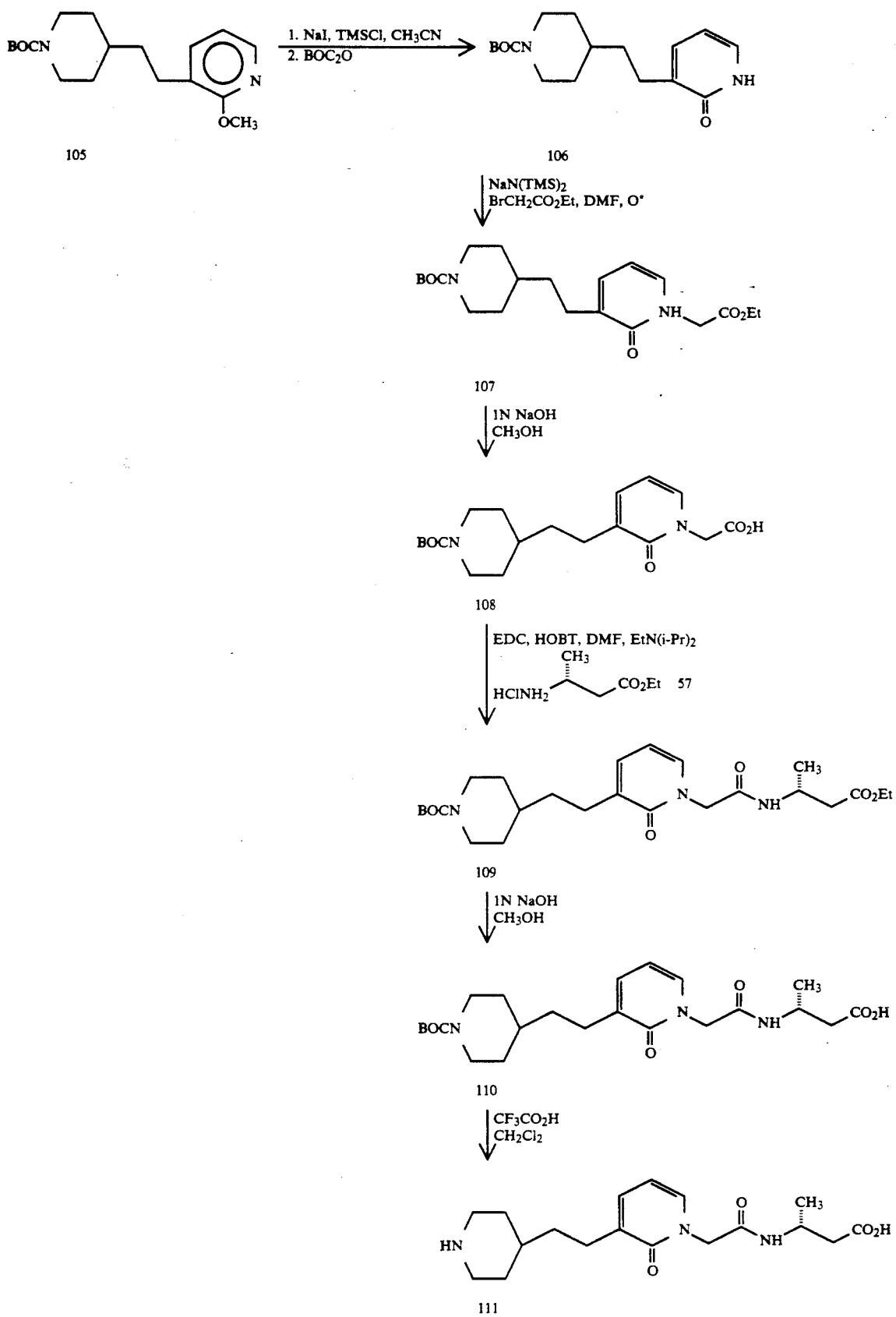

SCHEME 14
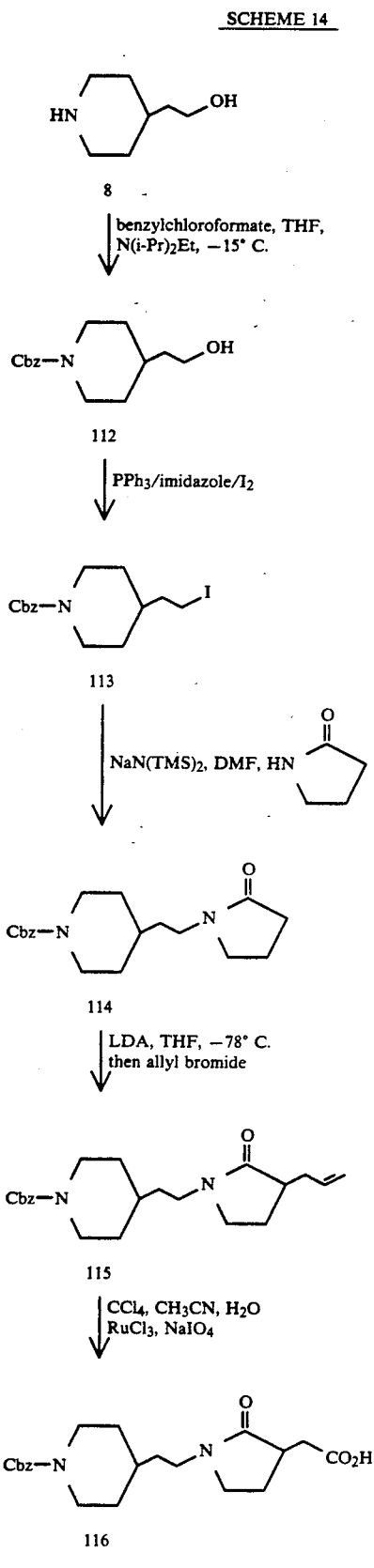
SCHEME 14
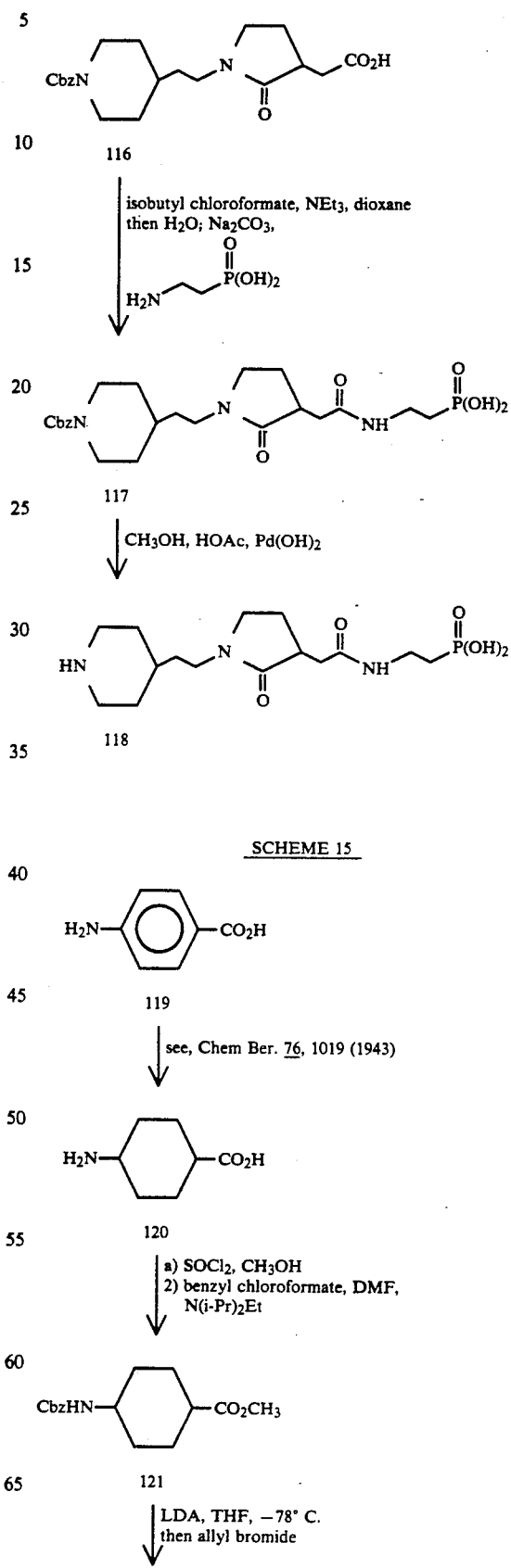

SCHEME 15 -continued

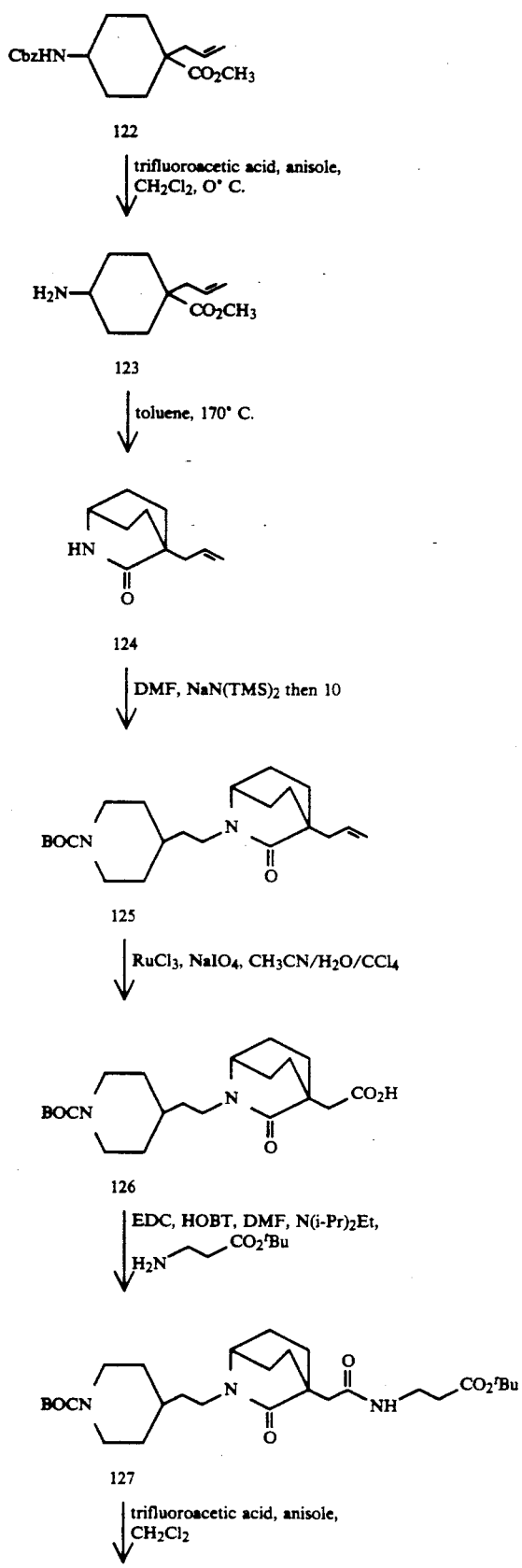

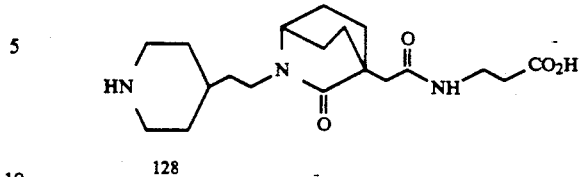

Preparation of 3-(Indol-3-yl)propanol-tert-butyldimethylsilyl ether (2)

To a stirring solution of 3-indolepropanol 1 (15 g, 86 mmol), DMF (200 mL), and imidazole (12.8 g, 0.19 mol) at 0° C. was added tert-butyldimethylsilyl chloride (14.2 g, 95 mmol) followed by removal of the cooling bath. After 20 hours the reaction mixture was diluted with ether and then washed with $H_2O$ (2 times) and brine, dried ($MgSO_4$), and concentrated to yield the silyl ether 2 (29 g) as an amber oil. TLC Rf=0.54 (20% ethyl acetate/hexanes); $^1H$ NMR ($CDCl_3$) δ 8.07 (bs, 1H), 7.77 (d, J=7 Hz, 1H), 7.49 (d, J=7 Hz, 1H), 7.33 (t, J=7 Hz, 1H), 7.26 (t, J=7 Hz, 1H), 7.12 (s, 1H), 3.84 (t, J=6 Hz, 2H), 2.95 (t, J=7 Hz, 2H), 2.08 (m, 2H), 1.08 (s, 9H), 0.25 (s, 3H), 0.22 (s, 3H).

Preparation of N-Acetyl-3-(indol-3-yl)propanol-tertbutyldimethylsilyl ether (3)

A solution of the indole 2 (29 g, 86 mmol), $CH_2Cl_2$ (450 mL), 1,8-diazobicyclo[5.4.0]undec-7-ene (38 mL, 0.26 mol), 4-dimethylaminopyridine (1.0 g, 8.5 mmol), and acetic anhydride (32 mL, 0.34 mol) was stirred for 1 week at ambient temperature. The reaction mixture was concentrated and then diluted with ether. The ether was then washed with $H_2O$, 5% $KHSO_4$ and brine, dried ($MgSO_4$), and concentrated. Flash chromatography (silica, 5% ethyl acetate/hexanes) gave the acylated product 3 (27 g) as a yellow oil. TLC Rf=0.56 (20% ethyl acetate/hexanes).

Preparation of N-Acetyl-3-(indol-3-yl)propanol (4)

To a stirred solution of the silyl ether 3 (27 g, 81 mmol) in THF (270 ml) at ambient temperature was added a premixed solution of n-$Bu_4NF$ (1M in THF: 244 mL, 0.24 mol) and AcOH (14 mL, 0.24 mmol) (1:1). After 20 hours the reaction mixture was diluted with ether and then washed with $H_2O$ (2 times) and brine, dried ($MgSO_4$), and concentrated to give the alcohol 4 (19 g) as a yellow crystalline solid. TLC Rf=0.35 (60% ethyl acetate/hexanes); $^1H$ NMR ($CDCl_3$) δ 8.42 (m, 1H), 7.55 (d, J=7 Hz, 1H), 7.36 (t, J=7 Hz, 1H), 7.29 (t, J=7 Hz, 1H), 7.27 (7d, J=7 Hz, 1H), 7.22 (s, 1H), 3.76 (t, J=7 Hz, 2H), 2.82 (t, J=7 Hz, 2H) 2.61 (s, 3H), 2.00 (m, 2H).

Preparation of 5-(N-Acetyl-indol-3-yl)pent-2-enoic acid ethyl ester (5)

To a stirring solution of oxalyl chloride (11.4 mL, 0.13 mol) in $CH_2Cl_2$ (440 mL) at −78° C. was added dry DMSO (12.4 mL, 0.17 mol) dropwise. After 5 minutes, gas evolution ceased and the alcohol 4 (19 g, 87 mmol) in $CH_2Cl_2$ (40 mL) was added. After 30 minutes, $NEt_3$ (73 mL, 0.52 mol) was added to effect a thick slurry. The cooling bath was removed and the reaction stirred for an additional 15 minutes before adding (carbethoxymethylene)triphenyl phosphorane (33.5 g, 96 mmol). After 2.0 hours, the reaction mixture was diluted with ether and then washed with H₂O (2 times), 5% KHSO₄ and brine, dried (MgSO₄), and concentrated. Flash chromatography (20% ethyl acetate/hexanes) gave the olefin 5 (14 g) as a white solid. TLC Rf=0.54 (60% ethyl acetate/hexanes); ¹H NMR (CDCl₃) 8.42 (bd, 1H), 7.50 (d, J=7 Hz, 1H), 7.34 (t, J=7 Hz, 1H), 7.28 (t, J=7 Hz, 1H), 7.19 (bs, 1H), 7.03 (dt, J=18 and 7 Hz, 1H), 5.88 (d, J=18 Hz, 1H), 4.19 (q, J=7 Hz, 2H), 2.87 (t, J=7 HZ, 2H), 2.63 (m, 2H), 2.61 (s, 3H), 1.28 (t, J=7 Hz, 3H).

Preparation of
N-(R)-α-Methylbenzyl-3(R)-[2-(indol-3-yl)ethyl]β-alanine ethyl ester (6a) and
N-(R)-α-Methylbenzyl-3(S)-[2-(indol-3-yl)ethyl]β-alanine ethyl ester (6b)

A mixture of olefin 5 (2.77 g, 9.7 mmol) and R-(+)-α-methylbenzylamine (5.03 mL, 39 mmol) was heated under a cold finger at 110° C. for 40 hours. The cooled reaction mixture was applied directly to a flash chromatography column (silica, 40:2:1, hexanes:ethyl acetate: 2-propanol). The (R,R) isomer 6a eluted first (1.19 g) as a viscous yellow oil which solidified on standing. Recrystallization from hexanes/ethyl acetate provided crystalline material. The (R,S) isomer 6b eluted next (1.55 g) as a viscous yellow oil containing ca 10% of the (R,R) isomer. 6a: Rf=0.52 (60% EtOAc/hexanes); ¹H NMR (400 MHz, CDCl₃) δ 7.84 (br s, 1H), 7.52 (dd, J=7.9, 0.7 Hz, 1H), 7.20-7.35 (m, 6H), 7.16 (tm, J=7.1, 1.3 Hz, 1H), 7.08 (tm, J=7.3, 1.1 Hz, 1H), 6.70 (br d, J=2.4 Hz, 1H), 4.10 (q, J=7.1 Hz, 2H), 3.90 (q, J=6.6 Hz, 1H), 2.80-2.90 (m, 2H), 2.68 (ABX dt, J=16, 7.9 Hz, 1H), 2.53 (ABX dd, J=14.5, 5.9 Hz, 1H), 2.42 (ABX dd, J=14.6, 5.3 Hz, 1H), 1.79 (q, J=7.5 Hz, 2H), 1.33 (d, J=6.4 Hz, 3H), 1.22 (t, J=7.1 Hz, 3H). 6b: Rf=0.42 (60% EtOAc/hexanes); ¹H NMR (400 MHz, CDCl₃) δ 7.95 (br s, 1H), 7.57 (dd, J=7.5, 0.7 Hz, 1H), 7.34 (dm, J=8.1, 0.7 Hz, 1H), 7.17-7.30 (m), 7.11 (tm, J=7.9, 0.9 Hz, 1H), 6.89 (br d, J=2.2 Hz, 1H), 4.02-4.15 (ABX m, 2H), 3.89 (q, J=6.6 Hz, 1H), 2.95 (m, 1H), 2.82 (ABX ddd, J=15, 9.7, 5.9 Hz, 1H), 2.69 (ABX ddd, J=15, 9.7, 6.0 Hz, 1H), 2.47 (ABX dd, J=15.0, 5.1 Hz, 1H), 2.40 (ABX dd, J=15.0, 7.7 Hz, 1H), 1.96 (m, 1H), 1.83 (m, 1H), 1.30 (d, J=6.6 Hz, 3H), 1.21 (td, J=7.1, 0.7 Hz, 3H).

Preparation of 3(R)-[2-(indol-3-yl)ethyl]β-alanine ethyl ester (7a)

Amine 6a (996 mg, 2.74 mmol) was dissolved in 10 mL ETOH. After addition of Pearlman's catalyst (20% Pd(OH)₂/C, 128 mg) the flask was charged with hydrogen and maintained at balloon pressure. After 16 hours an additional portion of catalyst was added (122 mg) along with fresh H₂. Four hours later the sample was filtered through celite and concentrated to provide amine 7a (707 mg, 99%, ca 95% pure).: Rf=0.22 (10:1, NH₃ said. CHCl₃:EtOAc); ¹H NMR (400 MHz, CDCl₃) δ 8.01 (br s, 1H), 7.60 (dt, J=8.9, 0.4 Hz, 1H), 7.35 (dt, J=8.1, 0.9 Hz, 1H), 7.19 (td, J=7.1, 1.3 Hz, 1H), 7.11 (td, J=7.1, 1.2 Hz, 1H), 6.99 (br d, J=2.2 Hz, 1H), 4.15 (q, J=7.1 Hz, 2H), 3.72 (q, J=7.0 Hz, 1H), 3.29 (m, 1H), 2.92-2.78 (m, 2H), 2.53 (ABX dd, J=15.6, 4.0 Hz, 1H), 2.33 (ABX dd, J=15.6, 8.8 Hz, 1H), 1.92-1.73 (m, 2H), 1.25 (q, J=7.1 Hz, 3H).

Preparation of N-BOC-4-piperidineethanol (9)

To a stirred solution of 4-piperidineethanol 8 (18.7 g, 0.14 mol) and DMF (200 mL) at 0° C. was added N-tert-butoxycarbonyl anhydride (31 g, 0.14 mol). After 1 hr the cooling bath was removed and the reaction mixture stirred for 20 hr. The reaction mixture was diluted with ether and then washed with water (2×) and brine, dried (MgSO₄), and concentrated to furnish 9 (26 g, 62%) as a colorless oil. TLC Rf=0.25 (40% ethyl acetate/hexanes); ¹H NMR (300 MHz, CDCl₃) δ 4.09 (bs, 2H), 3.72 (t, J=7 Hz, 2H), 2.70 (m, 2H), 1.75-1.10 (m, 7H), 1.46 (s, 9H).

Preparation of N-BOC-4-piperidine ethyl iodide (10)

To a stirring solution of 9 (18.0 g 77 mmol), triphenylphosphine (22.2 g, 85 mmol), imidazole (7.9 g, 115 mmol), and benzene (800 mL) at ambient temperature was added iodine (22.0 g, 85 mmol). After 5 min the heterogeneous reaction mixture was filtered and the filtrate concentrated. Flash chromatography (silica gel, 10% ethyl acetate/hexanes) gave 10 (20 g, 59%) as an oil. TLC Rf=0.95 (50% ethyl acetate/hexanes); ¹H NMR (300 MHz, CDCl₃) δ 4.11 (m, 2H), 3.24 (t, J=6 Hz, 2H), 2.72 (m, 2H), 1.82 (dt, J=7, 7 Hz, 2H), 1.75, −1.55 (m, 5H), 1.48 (s, 9H), 1.12 (m, 2H).

Preparation of N-BOC-4-piperidine ethyl azide (11)

A solution of 10 (5.0 g, 14.7 mmol), DMSO (75 mi), and NaN₃ (1.9, 29.4 mmol) was heated at 70° C. for 2 hr. The cooled reaction mixture was diluted with ethyl acetate and then washed with water (2×) and brine, dried (MgSO₄), and concentrated to afford 11 (3.6 g, 96%) as a colorless oil. TLC Rf=0.75 (30% ethyl acetate/hexanes); ¹H NMR (300 MHz, CDCl₃) δ 4.11 (m, 2H), 3.36 (t, J=7 Hz, 2H), 2.73 (m, 2H), 1.70 (m, 3H), 1.49 (s, 9H), 1.15 (m, 2H).

Preparation of N-BOC-4 piperidine ethyl amine (12)

A mixture of 11 (1.1 g, 4.3 mmol), 10% Pd/C (0.16 g), and ethanol was stirred under a hydrogen atmosphere (1 atm) for 1.5 hr. The reaction mixture was then filtered through a celite pad and the filtrate concentrated to give crude 12 (1.0 g) as an oil. TLC Rf=0.18 (9:1:1 CH₂CH₂/CH₃OH/HOAc); ¹H NMR (300 MHz, CDCl₃) δ 4.10 (m, 2H), 2.78 (t, J=7 Hz, 2H), 2.70 (m, 2H), 1.80 (m, 2H), 1.67 (m, 2H), 1.52 (m, 1H), 1.47 (s,9H), 1.17 (m, 2H).

Preparation of
1-[2-(N-Boc-piperidin-4-yi)ethyl]-3-propen-2-yl-(2-imidazolidinone) (14)

To a stirred solution of 13 (1.5 g, 17 mmol) in DMF (75 mL) at ambient temperature was added LiN(TMS)₂ (1M in hexanes, 17 mL) to effect a precipitate. Allyl bromide (1.6 mL, 19 mmol) was then added to the reaction mixture. After 15 min the homogeneous mixture was treated again with LiN(TMS)₂ (14 mL) followed by the iodide 10 (5.9 g, 17 mmol) after 5 min. The reaction was stirred for 20 hr then diluted with ether. The ether portion was washed with water (2×), 5% KHSO₄ and brine, dried (Mg SO₄), and concentrated. Flash chromatography (40% ethyl acetate/hexanes) gave 14 (0.8 g, 15%) as a colorless oil. TLC Rf=0.46 (70% ethyl acetate/hexanes); ¹H NMR (300 MHz, CDCl₃) δ 5.80 (m, 1H), 5.23 (m, 2H), 4.10 (m, 2H), 3.82 (m, 2H), 3.30 (m, 6H), 2.72 (m, 2H), 1.70 (m, 3H), 1.50 (m, 2H), 1.46 (s, 9H), 1.15 (m, 2H).

Preparation of 1-[2-(N-Boc-piperidine-4-yl)ethyl]3-acetic acid-(2-imidazolidinone) (15)

To a vigorously stirred solution of 14 (450 mg, 1.4 mmol), CCl$_4$, acetonitrile, and water at ambient temperature was added RuCl$_3$ (12 mg, 4.4 mol%) and excess NaIO$_4$. After 60 hr the reaction was filtered through a celite pad washing with ethyl acetate. The filtrate was extracted with sat NaHCO$_3$ followed by acidifying the aqueous phase to pH 3 with 5% KHSO$_4$. The acidic aqueous phase was then extracted with ethyl acetate (2×) and the organic portion was dried (Mg SO$_4$) and concentrated. Flash chromatography (silica gel, 9:0.2:0.2 CH$_2$Cl$_2$/CH$_3$OH/HOAc gave 15 (60 mg, 12%) as a colorless oil. TLC Rf=0.29 (9.5:0.5:0.5 CH$_2$Cl$_2$/CH$_3$OH/HOAc); $^1$H NMR (300 MHz, CDCl$_3$) δ 4.05 (m, 2H), 3.90 (m, 2H), 3.45 (m, 2H), 3.40 (m, 2H), 3.24 (m,2H), 2.69 (m, 2H), 1.72 (m, 2H), 1.46 (m, 3H), 1.46 (s,9H), 1.15 (m, 2H).

Preparation of [1-[2-(N-Boc-piperidin-4-yl)ethyl1-(2-imidazolidinone)-3]-acetyl-3(R)-[2-( indol-3-yl)-ethyl]δ-alanine ethyl ester (16)

A stirred mixture of 15 (60 mg, 0.17 mmol), 7a (66 mg, 0.25 mmol), HOBT (30 mg, 0.22 mmol), triethylamine (31 uL, 0.22 mmol), and DMF (1.1 mL) at 0° C. was treated with EDC (42 mg, 0.22 mmol) followed by removal of the cooling bath. After 20 hr the reaction was diluted with ethyl acetate and then washed with water, 5% KHSO$_4$, and brine, dried (MgSO$_4$), and concentrated. Flash chromatography (silica gel, ethyl acetate) gave 16 (35 mg, 35%) as a colorless oil. TLC Rf=0.20 (ethyl acetate); $^1$H NMR (300 MHz, CDCl$_3$) δ 8.07 (bs, 1H), 7.57 (d, J=8 Hz, 1H), 7.37 (d, J=8 Hz, 1H), 7.18 (t, J=8 Hz, 1H), 7.11 (t, J=8 Hz, 1H), 7.05 (bs, 1H), 6.89 (d, J=9 Hz, 1H), 4.37 (m, 1H), 4.13 (q, J=7 Hz, 2H), 4.07 (m, 2H), 3.83 (dd, J=18 Hz, 2H), 3.43-3.20 (m, 6H), 2.80 (m, 2H), 2.56 (d, J=5 Hz, 2H), 2.00-1.05 (m, 9H), 1.47 (s, 9H), 1.25 (t,J=7 Hz, 3H).

Preparation of [1-[2-(N-Boc-piperidin-4-yl)ethyl]-(2-imidazolidinone)-31-acetyl-3(R)-[2-( indol-3-yl)ethyl]-β-alanine (17)

A mixture of 16 (30 mg, 50 umol), 1N, NaOH (0.2 mL) and ethanol was stirred at ambient temperature for 1 hr. The reaction mixture was then diluted with ethyl acetate and 5% KHSO$_4$ and the organic portion washed with water and brine followed by drying (MgSO$_4$) and concentration to furnish 17 (30 mg, 100%) as a colorless oil. TLC Rf=0.74 (9:1:1 CH$_2$Cl$_2$/CH$_3$OH/HOAc).

Preparation of [1-[2-piperidin-4-yl)ethyl]-(2-imidazolidinone)-31-acetyl-3(R)-[2-( indol-3-yl)ethyl]δ-alanine (18)

To a stirring solution of 17 (30 mg, 50 umol), dichloromethane (300 uL), and anisole (15 uL, 100 umol) at −15° C. was added TFA (0.3 mL). After 20 min the reaction mixture was concentrated and the residual TFA removed azeotropically with toluene. Flash chromatography (silica gel, 10:0.8:0.8 methanol/NH$_4$)/water) gave 18 (15 mg, 66%) as a white solid. TLC Rf=0.16 (10:1:1 methanol/NH4OH/water); $^1$NMR (300 MHz, CD$_3$OD) δ 7.44 (d, J=Hz, 1H), 7.20 (d, J=8 Hz, 1H), 6.95 (t, =J=8 Hz, 1H), 6.94 (s, 1H), 6.88 (t, J=8 Hz, 1H), 4.17 (m, 1H), 3.71 (s, 2H), 3.40)3.10 (m, 8H), 2.86 (m, 2H), 2.70 (t, J=6 Hz, 2H), 2.32 (m, 2H), 1.90 (m, 4H), 1.55 (m, 1H), 1.43 (m, 2H), 1.28 (m, 2H).

Preparation of 1-[2-(N-Boc-piperidin-4-yl)ethyl]-(2-pyrrolidinone) (19)

To a stirred solution of 12 (2.7 g, 11.8 mmol) acetonitrile (60 mL), and diisopropyl ethylamine (4.1 mL 23.6 mmol) at 0° C. was added 4-chlorobutyryl chloride (2.6 mL, 23.6 mmol) followed by removal of the cooling bath. After 5 hr the reaction mixture was diluted with ethyl acetate and then washed with water (2×) and brine, dried (MgSO$_4$), and concentrated. The crude amide was dissolved in DMF (60 mL) cooled to 0° C. then treated with NaN(TMS)$_2$ (1M in THF, 11.8 mL). After 5 min the reaction mixture was diluted with ethyl acetate and then washed with water and brine, dried (MgSO$_4$), and concentrated. Flash chromatography (silica gel, 70% ethyl acetate/hexanes); gave 19 (0.4 g, 12%) as a colorless oil. TLC Rf=0.27 (70% ethyl acetate/hexanes); $^1$H NMR (300 MHz, CDCl$_3$) δ 4.10 (m, 2H), 3.39 (t, J=7 Hz, 2H), 3.34 (t, J=7 Hz, 2H), 2.70 (m, 2H), 2.40 (m, 2H), 2.05 (m, 2H), 1.72 (m, 2H), 1.46 (m, 3H), 1.45 (s, 9H), 1.13 (m, 2H).

Preparation of 1-[2-(N-Boc-piperidin-4-yl)ethyl]-3-propen-2yl-(2-pyrrolidinone) (20)

To a stirred solution of 19(325 mg, 1.1 mmol) in THF ( 5 mL) at −78° C. was added LDA (0.5M in THF 2.4 mL) dropwise. After 15 min allyl bromide (0.16 mL, 2.2 mmol) was added and the reaction stirred at −78° C. for 1 hr followed by quenching with HOAc (0.1 mL). The reaction mixture was then diluted with ethyl acetate and then washed with water and brine, dried (MgSO$_4$), and concentrated. Flash chromatography (silica gel, 50% ethyl acetate/hexanes) gave 20 (160 mg, 45%) as an oil. TLC Rf-0.23 (50% ethyl acetate/hexanes); $^1$H NMR (300 MHz, CDCl$_3$) δ 5.80 (m, 1H), 5.10 (m, 2H), 4.10 (m, 2H), 3.32 (m, 4H), 2.70 (m, 2H), 2.56 (m, 2H), 2.20 (m, 2H), 1.73 (m, 3H), 1.48 (s, 9H), 1.13 (m, 2H) .

Preparation of 1-[2-(N-Boc-piperidin-4-yl)ethyl]-3-acetic acid-2-pyrrolidinone (21)

Utilizing the procedure for converting 14 to 15, 20 (130 mg, 0.4 mmol) gave 21 (80 mg, 48%) as an oil after flash chromatography (silica gel, 9:0.2:0.2 CH$_2$Cl$_2$/CH$_3$OH/HOAc). TLC Rf=0.25 (9:0.2:0.2 CH$_2$Cl$_2$/CH$_3$OH/HOAc); $^1$H NMR (300 MHz, CDCl$_3$) δ 4.05 (m, 2H), 3.40 (m, 4H), 2.96 (m, 1H), 2.83 (m, 1H), 2.70 (m, 2H), 2.55 (m, 1H), 2.40 (m, 1H), 1.90-1.10 (m, 7H), 1.48 (s, 9H).

Preparation of [1-[2-(N-Boc-piperidin-4-yl)ethyl1-2-pyrrolidinone-3]acetyl-[2-(indol-3-yl )-ethyl]β-alanine ethyl ester (22)

Utilizing the procedure for converting 15 to 16, 21 (120 mg, 0.35 mmol) gave 22 (90 mg, 48%) after flash chromatography (silica gel, ethyl acetate). TLC Rf=0.40 (ethyl acetate); $^1$H NMR (400 MHz, CDCl$_3$) δ 8.09 (bd, 1H), 7.58 (d, J=8 Hz, 1H), 7.36 (d, J=8 Hz, 1H), 7.17 (t, j=8 Hz, 1H), 7.10 (t, J=8 Hz, 1H), 7.07 (bs, 1H), 4.39 (m, 1H), 4.12 (q, J=7 Hz, 2H), 4.05 (m, 2H), 3.30 (m, 4H), 2.90-2.25 (m, 8H), 2.00-1.00 (m, 8H), 1.48 (s, 9H), 1.23 (t, J=7 Hz, 3H).

Preparation of [1-[2-(N-Boc-piperidin-4-yl)ethyl]-2-pyrrolidinone-3]acetyl-[2-(indol-3-yl)-ethyl]β-alanine (23)

Utilizing the procedure for converting 16 to 17, 22 (80 mg, 0.14 mmol) gave 23 (80 mg) after work-up, which was used directly for the next reaction. TLC Rf=0.50 (9:1:1 CH$_2$Cl$_2$/CH$_3$OH/HOAc).

Preparation of [1-[2-(piperidin-4-yl)ethyl]-2-pyrrolidinone-31acetyl-r2-(indol-3-yl)-ethyl ]β-alanine-(24)

Utilizing the procedure for converting 17 to 18, 23 (80 mg, 0.14 mmol) gave 24 (15 mg, 23%) after flash chromatography (silica gel, 10:0.65:0.65 methanol/NH$_4$OH/water). TLC Rf=0.53 (10:1:1 methanol/NH$_4$OH/water); $^1$H NMR (300 MHz, CD$_3$OD) δ 7.47 (t, J=7 Hz, 1H), 7.25 (d, J=7 Hz, 1H), 6.99 (m, 2H), 6.88 (t, J=7 Hz, 1H), 4.19 (m, 1H), 3.49 (m, 0.5 H), 3.40 (m, 0.5H), 3.34–2.95 (m, 6H), 2.90–2.60 (m, 4H), 2.48 (m, 1H), 2.40–2.20 (m, 4H), 2.13 (m, 1H), 2.00–1.05 (m, 11H).

Preparation of 5-chloro-valeroyl-amino-2-propene (26)

To a stirred mixture of allyl amine 25 (2.0 g, 27 mmol), NMM (8.9 mL, 81 mmol), and acetonitrile (140 mL), at ambient temperature was added 4-chlorobutyryl chloride (3.4 mL, 27 mmol). After 20 hours the reaction mixture was concentrated. The residue was dissolved in ethyl acetate and then washed with water, 5% KHSO$_4$ and brine, dried (MgSO$_4$), and concentrated to give 26 (4.1 g, 87%) as a yellow oil. TLC Rf=0.17 (40% ethyl acetate/hexanes).

Preparation of 1-(propen-2-yl)-2-)piperidone (27)

To a stirred solution of 26 (2.0 g, 11 mmol) in THF (110 mL) at −78° C. was added NaN(TMS)$_2$ (1.0M in THF, 11 mL) in a stream followed by removal of the cooling bath. After 1.5 hours the reaction mixture was diluted with ethyl acetate and then washed with water, 5% KHSO$_4$ and brine, dried (MgSO$_4$), and concentrated. Flash chromatography (silica gel, 60% ethyl acetate/hexanes) gave 27 (1.1 g, 72%) as an oil. TLC Rf=0.15 (60% ethyl acetate/hexanes); $^1$H NMR (300 MHz, CDCl$_3$) 6 5.78 (m, 1H), 5.15, 4.00 (d, J=7 Hz, 2H), 3.24 (m, 2H), 2.41 (m, 2H), 2.07 (m, 2H), 1.80 (m, 4H).

Preparation of 3-[2-(N-Boc-piperidin-4-yl)ethyl]-1-acetic acid-2-piperidone (28)

To a stirred solution of 27 (1.0 g, 7.2 mmol) and THF (70 mL) at −78° C. was added LDA (0.5M in THF, 15.8 mL) dropwise. After 15 minutes iodide 10 (2.7 g, 7.9 mmol) in THF (5 mL) was added followed by slow warming to −30° C. over a 1 hour period. The reaction was quenched with acetic acid (0.2 mL) then concentrated. Flash chromatography (silica gel, 40% ethyl acetate/hexanes) gave 28 (1.5 g, 59%) as an oil. TLC Rf=0.58 (ethyl acetate); $^1$H NMR (300 MHz, CDCl$_3$) δ 5.77 (m, 1H), 5.15 (m, 1H), 4.06 (m, 2H), 4.00 (m, 2H), 3.23 (m, 2H), 2.59 (m, 2H), 2.19 (m, 1H), 2.05–1.25 (m, 11H), 1.48 (s, 9H), 1.10 (m, 2H).

Preparation of 3-[2-(N-Boc-piperidin-4-yl)ethyl]-3-acetic acid-2-piperidone (29)

A vigorously stirred mixture of 28 (0.84 g, 2.4 mmol), CCl$_4$ (5 mL), acetonitrile (5 mL), NaIO$_4$ (2.1 g, 9.8 mmol), and water (7.5 mL) at ambient temperature was treated with RuCl$_3$ (50 mg, 0.24 mmol). After 20 hours additional RuCl$_3$ ((50 mg) was added. After 4 hours the reaction mixture was diluted with ethyl acetate and half sat NaHCO$_3$. After shaking and separation the aqueous portion was acidified with 5% KHSO$_4$, and extracted with ethyl acetate. The organic extracts were washed with brine, dried (MgSO$_4$), and concentrated. Flash chromatography (silica gel, 9:0.2:0.2 CH$_2$Cl$_2$/methanol/HOAc) gave 29 (280 mg, 30%) as an oil. TLC Rf=0.36 (9:0.5:0.5 CH$_2$Cl$_2$/methanol/HOAc).

Preparation of [3-[2-(N-Boc-piperidin-4-yl)ethyl]-2-imidazolidinone-l)acetyl-[3(R)-[2-(indol-3-yl)ethyl]-β-alanine ethyl ester (30)

Utilizing the procedure for converting 15 to 16, 29 (280 mg, 0.76 mmol) gave 30 (300 mg, 64%) as an oil after flash chromatography (silica gel, 85% ethyl acetate/hexanes). TLC Rf=0.18 (85% ethyl acetate/hexanes); $^1$H NMR (300 MHz, CDCl$_3$) δ 8.14 (m, 1H), 7.60 (d, J=8 Hz, 1H), 7.39 (d, J=8 Hz, 1H), 7.20 (t, J=8 Hz, 1H), 7.13 (t, J=8 Hz, 1H), 7.05 (bs, 1H), 6.90 (d, J=9 Hz, 1H), 4.35 (m, 1H), 4.11 (q, J=7 Hz, 2H), 4.05 (m, 2H), 3.98 (s, 2H), 3.40 (m, 2H), 2.90–2.50 (m, 6H), 2.33 (m, 1H), 2.00–1.00 (m, 15H), 1.48 (s, 9H), 1.27 9t, J=7 Hz, 3H).

Preparation of [3-[2-(N-Boc-piperidin-4-yl)ethyl-2-piperidone-1]acetyl-[3(R)-[2-indol-3 -yl)ethyl]β-alanine (31)

Utilizing the procedure for converting 16 to 17, 30 (160 mg, 0.26 mmol) gave 31 (140 mg, 92%) as a white solid after work-up. TLC Rf=0.59 (9:1:1 CH$_2$Cl$_2$/methanol/HOAc).

Preparation of [3-[2-(piperidin-4-yl)ethyl-2-piperidone-1]acetyl-[3(R)-[2-indol-3 -yl)ethyl]β-alanine (32)

Utilizing the procedure for converting 17 to 18, 31 (140 mg, 0.24 mmol) gave 32 (55 mg, 47%) as a white solid after flash chromatography (silica gel, 10:0.4:0.4 methanol/NH$_4$OH/water). TLC Rf=0.46 (10:1:1 methanol/NH$_4$OH/water); $^1$H NMR (300 MHz, CD$_3$OD) δ 7.54 (d, J=8 Hz, 1H), 7.30 (d, J=8 Hz, 1H), 7.03 (t, J=8 Hz, 1H), 7.02 (bs, 1H), 6.97 (m, 1H), 4.28 (m, 1H), 4.20 (d, J=16 Hz, 0.5H), 4.12 (d, J=16 Hz, 0.5H), 3.80 (d, J=16 Hz, 0.5H), 3.75 (d, J=16 Hz, 0.5H), 3.50–3.15 (m, 4H), 2.80 (m, 4h), 2.50–2.30 (m, 3H), 2.00–1.20 (m, 15H).

Preparation of 3-[2-(N-Boc-piperidin-4-yl)ethyl]-2-pyrrolidinone (36a)

To the benzyl amide 35a (0.8 g, 2.2 mmol) in THF (20 mL) at −78° C. was added freshly prepared lithium di-tert-butylbiphenyl (0.5M in THF, 10.8 mL) in 2 portions. After 1 hour the reaction mixture was quenched with HOAc (0.1 mL) followed by concentration. Flash chromatography (5% methanol/ethyl acetate) gave 36a (470 mg, 72%) as a white solid. TLC Rf=0.27 (10% methanol/ethyl acetate); $^1$H NMR (300 MHz, CDCl$_3$) δ 6.03 (m, 1H), 4.10 (m, 2H), 3.35 (m, 2H), 2.70 (m, 2H), 2.33 (m, 2H), 1.92 (m, 1H), 1.80 (m, 1H), 1.70 (m, 2H), 1.50–1.30 (m, 4H), 1.48 (s, 9H), 1.12 (m, 2H).

Preparation of Methyl 1-acetate-3-[2-(N-Boc-piperidin-4-yl)ethyl]-2-pyrrolidinone (37a)

To a stirred solution of 36a (340 mg, 1.1 mmol) in THF (10 mL) at −78° C. was added NaN(TMS)$_2$ (1.0M in THF, 1.1 mL). After 15 minutes ethyl bromoacetate (250 uL, 2.2 mmol) was added and the reaction mixture to warm to −20° C. After 2 hours the reaction was quenched with HOAc (0.1 mL) and then concentrated. Flash chromatography (silica gel, 50% ethyl acetate/hexanes) gave 37a (380 mg, 90%) as an oil. TLC Rf=0.66 (10% methanol/ethyl acetate); $^1$H NMR (300 MHz, CDCl$_3$) δ 4.22 (q, J=7 Hz, 2H), 4.10 (m, 2H), 4.08 (s, 2H), 3.24 (m, 2H), 2.70 (m, 2H), 2.44 (m, 1H), 2.26 (m, 1H), 2.00–1.65 (m, 4H), 1.48 (s, 9H), 1.50–1.30 (m, 4H), 1.31 (t, J=7 Hz, 3H), 1.12 (m, 2H).

Preparation of 3-[2-(N-Boc-piperidin-4-yl)ethyl]-2-pyrrolidinone-1-acetic acid (38a)

Utilizing the procedure for converting 16 to 17, 37a (390 mg, 1.1. mmol) gave 38a (340 mg, 91%) as a white foam after work-up. TLC Rf=0.39 (9:0.5:0.5 CH$_2$Cl$_2$/methanol/HOAc).

Preparation of [3-[2-(N-Boc-piperidin-4-yl)ethyl]-2-pyrrolidinone-1]acetyl-[3(R)-(indol-3-yl) -ethyl]β-alanine ethyl ester (39a)

Utilizing the procedure for converting 15 to 16, 38a (310 mg, 0.92 mmol) gave 39a (460 mg, 86%) as a yellow oil after flash chromatography (silica gel, 85% ethyl acetate/hexanes). TLC Rf=0.16 (85% ethyl acetate/hexanes); $^1$H NMR (300 MHz, CDCl$_3$) δ 8.21 (bs, 1H), 7.58 (d, J=8 Hz, 1H), 7.38 (d, J=8 Hz, 1H), 7.20 (t, J=8 Hz, 1H), 7.13 (t, J=8 Hz, 1H), 7.05 (bs, 1H), 6.72 (d, J-10 Hz, 1H), 4.35 (m, 1H), 4.13 (q, J=7 Hz, 2H), 4.09 (m, 2H), 3.97 (d, J=15 Hz, 1H), 3.86 (d, J=15 Hz, 1H), 3.41 (m, 2H), 2.80 (m, 2H), 2.65 (m, 2H), 2.55 (dd, J=1.5 Hz, 2H), 2.45 (m, 1H), 2.24 (m, 1H), 2.00–1.20 (m, 10 H), 1.48 (s, 9H), 1.26 (t, J=7 Hz, 3H), 1.04 (m, 2H).

Preparation of [3-[2-(N-Boc-piperidin-4-yl)ethyl-1]acetyl-[3(R)-[2-(indol-3-yl) ethyl]β-alanine (40a)

Utilizing the procedure for converting 16 to 17, 39a (460 mg, 0.79 mmol) gave 40a (360 mg, 86%) as a foam after work-up. TLC Rf=0.57 (9:1:1 CH$_2$Cl$_2$/methanol/HOAc).

Preparation of [3-[2-(piperidin-4-yl)ethyl-1]acetyl-[3(R)-[2-indol-3-yl)ethyl ]β-alanine (41a)

Utilizing the procedure for converting 17 to 18, 40a (360 mg, 0.65 mmol) gave 41a (180 mg, 59%) as a white solid after flash chromatography (silica gel, 10:0.4:0.4 methanol/NH$_4$OH/water). TLC Rf=0.21 (10:0.4:0.4 methanol/NH$_4$OH/water); $^1$H NMR (300 MHz, CD$_3$OD) δ 7.36 (d, J=8 Hz, 1H), 7.13 (d, J=8 Hz, 1H), 6.87 (t. J=8 Hz, 1H), 6.86 (s, 1H), 6.78 (t, J=8 Hz, 1H), 4.09 (m, 1H), 3.82 (d, J=16 Hz, 1H), 3.70 (d, J=16 Hz, 1H), 3.33 (m, 2H), 3.07 (m, 2H), 2.63 (m, 4H), 2.30 (m, 1H), 2.25 (m, 2H), 2.05 (m, 1H), 1.90–1.50 (m, 6H), 1.40–1.05 (m, 6H).

Preparation of 3-[2-(N-Boc-piperidin-4-yl)ethyl]-2-pyrrolidinone (36b)

Utilizing the procedure for converting 35a to 36a, 35b (0.7 g, 1.7 mmol) gave 36b (260 mg, 62%) as a white solid after flash chromatography (silica gel, 5% methanol/ethyl acetate). TLC=Rf=0.27 (10% methanol/ethyl acetate).

Preparation of Ethyl 3-[2-N-Boc-piperidin-4-yl)ethyl]-2-pyrrolidinone-1-acetate (37b)

Utilizing the procedure for converting 36a to 37a, 36b (260 mg, 0.88 mmol) gave 37b (300 mg, 89%) as an oil after flash chromatography (silica gel, 50% ethyl acetate/hexanes). TLC Rf=0.66 (10% methanol/ethyl acetate).

Preparation of 3-[2-(N-Boc-piperidin-4-yl)ethyl]-2-pyrrolidinone-1-acetic acid (38b)

Utilizing the procedure for converting 16 to 17, 37b (300 mg, 0.78 mmol) gave 38b (260 mg, 98%) as a crystalline solid. TLC Rf=0.38 (9:0.5:0.5 CH$_2$Cl$_2$/methanol/HOAc).

Preparation of [3-[2-(N-Boc-piperidin-4-yl)ethyl]-2-pyrrolidinone-l]acetyl-[3(R)-[2-( indol-3-yl)-ethyl]β-alanine ethyl ester (39b)

Utilizing the procedure for converting 15 to 16, 38b (260 mg, 0.73 mmol) gave 39b (360 mg, 83%) as an oil after flash chromatography (silica gel, 85% ethyl acetate/hexanes). TLC Rf=0.16 (85% methanol/ethyl acetate); $^1$H NMR (300 MHz, CDCl$_3$) δ 8.29 (bs, 1H), 7.57 (d, J=8 Hz, 1H), 7.38 (d, J=8 Hz, 1H), 7.19 (t, J=8 Hz, 1H), 7.12 (t, J=8 Hz, 1H), 7.04 (d, J=1 Hz, 1H), 6.67 (d, J=10 Hz, 1H), 4.33 (m, 1H), 4.13 (q, J=7 Hz, 2H), 4.07 (m, 2H), 3.99 (d, i=16 Hz, 1H), 3.82 (d, J=16 Hz, 1H), 3.40 (m, 2H), 2.80 (m, 2H), 2.68 (m, 3H), 2.55 (dd, J=5,2 Hz, 2H), 2.43 (m,1H), 2.22 (m, 1H), 2.00–1.00 (m, 11H), 1.47 (s, 9H), 1.28 (t, J=7 Hz, 3H) .

Preparation of [3-[2-(N-Boc-piperidin-4-yl)ethyl]-2-pyrrolidinone-1]-acetyl-[3(R)-[2 -indol-3-yl)-ethyl]β-alanine (40b)

Utilizing the procedure for converting 16 to 17, 39b (280 mg, 0.47 mmol) gave 40b (250 mg, 94%) as a white solid after flash chromatography (silica gel, 9:1:1 CH$_2$Cl$_2$/methanol/HOAc). TLC Rf=0.21 (9:1:1 CH$_2$Cl$_2$/methanol/HOAc).

Preparation of [3-[2-(N-piperidin-4-yl)ethyl)-2-pyrrolidinone-1]acetyl-[3 (R)-[2-( indol-3-yl)-ethyl]β-alanine (41b)

Utilizing the procedure for converting 17 to 18, 40b (250 mg, 0.44 mmol) gave 41b (100 mg, 49%) as a white solid after flash chromatography (silica gel, 10:0.4:0.4 methanol/NH$_4$OH/water). TLC Rf=0.46 (10:0.4:0.4 methanol/NH$_4$OH/water); $^1$H NMR (300 MHz, CD$_3$OD) δ 7.52 (d, J=8 Hz, 1H), 7.29 (d, J=8 Hz, 1H), 7.03 (t, J=8 Hz, 1H), 7.02 (s, 1H), 6.95 (t, J=8 Hz, 1H), 4.27 (m, 1H), 4.05 (d, J=16 Hz, 1H), 3.81 (d, J=16 Hz, 1H), 3.42 (m, 2H), 3.26 (m, 2H), 2.90–2.70 (m, 4H), 2.49 (m, 1H), 2.40 (d, J=6 Hz, 2H), 2.22 (m, 1H), 2.05–1.70 (m, 5H), 1.60–1.25 (m, 5H).

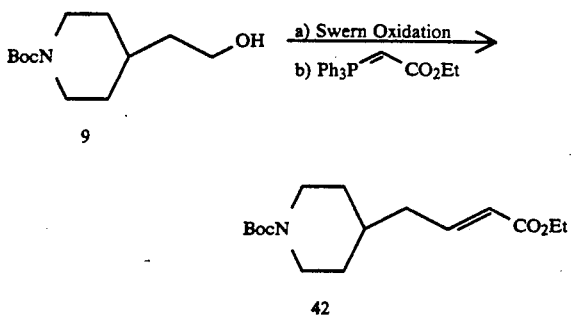

Ethyl 4-(N-BOC-piperidin-4-yl)crotonate(42)

To a stirred solution of oxalyl chloride (0.43 mL, 5.0 mmol) in $CH_2Cl_2$ (20mL) at −78° C. was added DMSO (0.52ml, 7.0 mmol) dropwise. After gas evolution subsided (~5 minutes) the alcohol 9 (0.8 g, 3.5 mmol) in $CH_2Cl_2$ (20 mL) was added in a stream. After 20 minutes triethylamine (1.7 mL, 12 mmol) was added dropwise and then the cooling bath removed. After 20 minutes carbethoxymethylenetriphenylphosphorane (1.4 g, 4.0 mmol) was added in one portion. After 2.0 hours the reaction mixture was diluted with petroleum ether and then washed sequentially with $H_2O$, 5% $KHSO_4$, and brine, dried ($MgSO_4$), and concentrated. Flash chromatography (silica, 15% ethyl acetate/hexanes) gave the ester 42 as a colorless oil.

TLC Rf=0.79 (50% ethyl acetate/hexanes); $^1H$ NMR (300 MHz, $CDCl_3$) δ 6.91 (dt,J=16 and 7 Hz, 1H), 5.81 (bd,J=17 Hz, 1H), 4.18 (q,J=7 Hz, 2H), 4.08 (m,2H), 2.67 (m,2H), 2.14 (t,J=7 Hz,2H), 1.70–1.05 (m,5H), 1.44(s,9H), 1.28(t,J=7H, 3H).

Preparation of Ethyl 4-(N-BOC-piperidin-4-yl)-butyrate (43)

The olefin 42 (26 g, 87 mmol) in ethyl acetate (500 mL) was hydrogenated, at ambient temperature, under a hydrogen atmosphere (1 atm) in the presence of 10% Pd/C (5.0 g) overnight. The reaction mixture was then purged with argon and filtered through a celite pad. Concentration of the filtrate followed by flash chromatography (silica, 10% ethyl acetate/hexanes) gave the ester 43 as a crystalline solid.

TLC Rf=0.42 (20% ethyl acetate/hexanes); $^1H$ NMR (300 MHz, $CDCl_3$) δ 4.16 (q,J=7 Hz,2H), 4.10 (m,2H), 2.69 (m,2H), 2.31 (t,J=7 Hz,2H), 1.68 (m,4H), 1.38 (s,9H), 1.40 (m,1H), 1.11 (m,2H).

Preparation of 4-(N-BOC-Piperin-4-yl)butanoic acid (44)

A solution of ester 43 (19 g, 63 mmol), ethanol (300 mL) and 1N NaOH (100 mL, 100 mmol) was stirred at ambient temperature for 2.5 hours followed by concentration. The residue was diluted with 5% $KHSO_4$ and ethyl acetate and then transferred to a separatory funnel. The phases were shaken then separated and then the organic portion was washed with brine, dried ($MgSO_4$), and concentrated to give the acid 44 as a colorless oil that crystallized upon standing.

mp=80°–81° C.; TLC Rf=0.68 (ethyl acetate); $^1H$ NMR (300 MHz, $CDCl_3$) δ 4.10 (m, 2H), 2.71 (m,2H), 2.38 (t,J=7 Hz, 2H), 1.70 (m, 4H), 1.60–1.30 (m,3H), 1.48 (s,9H), 1.12 (m,2H).

Preparation of 4(S)-Benzyl-2-oxazolidinone-4-(BOC-piperidin-4-yl) butyrate (45)

To a stirred solution of 44 (15.3 g, 56 mmol), $NEt_3$ (9.4 mL, 67 mmol) and dry THF (240 mL) at −78° C. was added trimethylacetyl chloride (7.6 mL, 61 mmol) in a stream. After 10 min. the cooling bath was removed and replaced with an icebath. After 1.0 h the heterogeneous mixture was recooled to −78° C. followed by cannula addition of lithium (S)-(−)-4-benzyl-2-oxazolidinone (62 mmol) in dry THF (150 mL) AT −78° C. with n-BuLi (38.8 mL, 62 mmol, 1.6 M/hexanes). After addition was complete, the reaction mixture was warmed to 0° C. for 1.0 h, and then diluted with ethyl acetate and washed with $H_2O$, sat. $NaHCO_3$, 5% $KHSO_4$ and brine, dried ($MgSO_4$), and concentrated. Flash chromatography (silica, 30% ethyl acetate/hexanes) gave 45 as a colorless oil.

TLC Rf=0.45 (30% ethyl acetate/hexanes); $^1H$ NMR (400 MHz, $CDCl_3$) 7.36–7.20 (m,5H), 4.67 (m,1H), 4.18 (m,2H), 4.08 (m,2H), 3.30 (dd,J=13 and 3 Hz, 1H), 2.93 (m,2H), 2.77(dd,J=13 and 10 Hz,1H), 2.69 (m,2H), 1.70 (m,4H), 1.50–1.30 (m,3H), 1.45 (s,9H), 1.11 (m,2H).

Preparation of 4(S)-Benzyl-2-oxazolidinone-4-(BOC-piperidin-4-yl)-2(R)-(2-cyanoethyl)butyrate (46)

To a stirred solution of $TiCl_4$ (42 mL, 42 mmol, 1M/$CH_2Cl_2$) and $CH_2Cl_2$ (250 mL) at 0° C. was added titanium (IV) isopropoxide (4.2 mL, 14 mmol). After 15 min. diisopropylethylamine (11 mL) in $CH_2Cl_2$ (75 mL) was added followed by continued stirring at 0° C. to the deep red solution. After 10 minutes, 45 (21.8 g, 51 mmol) in $CH_2Cl_2$ (75 mL) was added followed by continued stirring at 0° C. for 1.0 hour. Acrylonitrile (33.4 mL, 0.50 mol) was added at 0° C. to the deep red solution. After 4.0 h the reaction was quenched with sat. $NH_4Cl$ (150 mL) at 0° C., then extracted with $CH_2Cl_2$ (3×250 mL). The combined organic extracts were washed with sat. $NaHCO_3$ and brine, dried ($MgSO_4$) and concentrated. Flash chromatography (silica, 25% ethyl acetate/hexanes) gave crude 46 as a yellow oil. Crude 46 was chromatographed (silica, 2.5% acetone/$CH_2Cl_2$) to yield 46 as an oil which was 97% pure by HPLC in addition to mixed fractions (1.6 g).

TLC Rf=0.35 (2.5% acetone/$CH_2Cl_2$); $^1H$ NMR (400 MHz, $CDCl_3$) δ 7.50–7.30 (m,5H), 4.68 (m,1H), 4.21 (m,2H), 4.07 (m,2H), 3.80 (m,1H), 3.33 (dd,J=13 and 4 Hz, 1H), 2.77 (dd, J=13 and 10 Hz, 1H), 2.65 (m, 2H), 2.38 (m, 2H), 2.13 (m, 1H), 1.89 (m,1H), 1.75 (m, 1H), 1.63 (m,2H), 1.50 (m, 2H), 1.45 (s,9H), 1.35 (m, 1H), 1.25 (m, 2H), 1.08 (m, 2H).

Preparation of 4(S)-Cyclohexylmethyl-2-oxazolidinone-4-(BOC-piperidin-4-yl)-2(R)-(2-aminopropyl) butyrate HCl (47)

A mixture of 46 (19.2 g, 40 mmol), $PtO_2$ (2.0 g), $CH_3OH$ (70 mL) and $CHCl_3$ (7.0 mL) was shaken on the Parr apparatus under a hydrogen atmosphere (60 PSI) at ambient temperature for 3.0 h. The reaction mixture was filtered through a celite pad and then concentrated to furnish the crude amine HCl 47 as a white solid. This material was used directly in the next step.

TLC Rf=0.50 (10:1:1 $CH_2Cl_2$/$CH_3OH$/HOAc); $^1H$ NMR (400 MHz, $CDCl_3$) δ 8.28 (bs, 2H), 4.50 (m,1H), 4.35 (m,1H), 4.14 (m,1H), 4.03 (m,2H), 3.63 (m, 1H), 3.02 (m,2H), 2.63 (m,2H), 2.00–1.00 (m,24H), 1.45 (s,9H).

Preparation of
3-(R)-[N-BOC-2-(piperidin-4-yl)ethyl]-2-piperidone
(48)

The crude amine HCl 47 (16.6 g, 31 mmol), acetonitrile (750 mL), and NaHCO$_3$ (10.0 g) was stirred at ambient temperature for 20 h. The heterogeneous mixture was then treated with di-tert-butyldicarbonate (3.0 g) followed by continued stirring for 1.0 h to reprotect minor amounts of free piperidine that formed in the previous reaction. The NaHCO$_3$ was removed by filtration and the filtrate concentrated. Flash chromatography (silica, 5% CH$_3$OH/ethyl acetate) gave the lactam 48 as a colorless crystalline solid.

mp=110°–111° C.; TLC Rf=0.65 (20% CH$_3$OH/ethyl acetate); $^1$H NMR (400 MHz, CDCl$_3$) δ 6.31 (bs,1H), 4.06 (m,2H), 3.31 (m,2H), 2.67 (m,3H), 2.28 (m,1H), 2.00–1.20 (m,11H), 1.45 (s,9H), 1.10 (m,2H).

Preparation of Ethyl
[3(R)-[N-BOC-2-(Piperidin-4-yl)ethyl]-2-piperidone-1]
acetate (49)

To a stirred solution of 48 (6.7 g, 22 mmol) and dry THF (150 mL) at −78° C. was added NaN(TMS)$_2$ (24.5 mL, 24.5 mmol, 1M/hexanes) dropwise. After 15 min. ethyl bromoacetate (5.2 mL, 45 mmol) was added and then the reaction mixture warmed to 0° C. for 1.0 h. The reaction was quenched with AcOH (1.0 mL) then diluted with ethyl acetate, washed with H$_2$O and brine, dried (MgSO$_4$), and concentrated. Flash chromatography (silica, 40% ethyl acetate/hexanes) gave the ester 49 as a yellow oil.

TLC Rf=0.26 (40% ethyl acetate/hexanes); $^1$H NMR (300 MHz, CDCl$_3$) δ 4.20 (q,J=7 Hz,2H), 4.17 (d,J 18 Hz,1H), 4.08 (m,2H), 3.98 (d,J=18 Hz, 1H), 3.37 (m,2H), 2.68 (m,2H), 2.32 (m,1H), 2.00–1.25 (m,11H), 1.45(s,9H), 1.30 (t,J=7 Hz,3H), 1.11 (m,2H).

Preparation of
3-(R)-[N-BOC-2-(Piperidin-4-yl)ethyl]-2-piperidone-1]
acetic acid (50)

A solution of 49 (6.0 g, 15 mmol), 1N NaOH (50 mL, 50 mmol), and CH$_3$OH (75 mL) was stirred at ambient temperature for 1.0 h. The reaction mixture was then acidified with 5% aqueous KHSO$_4$ and then extracted with ethyl acetate. The organic portion was washed with brine, dried (MgSO$_4$), and concentrated to give the carboxylic acid 50 as a yellow oil. The oil was triturated with hexanes to give a fluffy white solid.

TLC Rf=0.31 (9:0.5:0.5 CH$_2$Cl$_2$/CH$_3$OH/AcOH); $^1$H NMR (400 MHz, CDCl) δ 4.13 (d,J=17 Hz,1H), 4.07 (m,2H), 4.06 (d,J=17 Hz,1H), 3.39 (m,2H), 2.33 (m, 1H), 1.95 (m,3H), 1.81 (m,1H), 1.70–1.25 (m, 7H), 1.45 (s,9H), 1.08 (m, 2H).

Preparation of 3(R)-BOC-Amino-1-azobutan-2-one (52)

To a stirred solution of 51 (3.8 g, 20 mmol), 4-methylmorpholine (2.2 mL, 20 mmol), and ethyl acetate (200 mL) at −15° C. was added isobutyl chloroformate (2.6 mL, 20 mmol). After 1.0 h the reaction mixture was washed with H$_2$O and brine, dried (MgSO$_4$), and filtered into a round bottom flask. After cooling to 0° C. the mixed anhydride was treated portion-wise with an ethereal solution of diazomethane (80 mL, 40 mmol, δ0.5M solution). After 2.0 h the cooling bath was removed and the excess diazomethane removed by purging the solution with argon for 30 min. Concentration gave the crude diazoketone 52 which was used directly for the next step.

TLC Rf=0.37 (30% ethyl acetate/hexanes).

Preparation of Ethyl N-BOC-3(R)-Methyl β-alanine
(53)

The crude diazoketone 52 (4.3 g, ~20.0 mmol) was dissolved in ethanol (250 mL) and treated sequentially with NEt$_3$ (3.4 mL, 24 mmol) and silver benzoate (1.4 g, 6.0 mmol) to effect vigorous gas evolution and afford a black precipitate. After 1.0 h the reaction mixture was concentrated and the residue purified by flash chromatography (silica, 10% ethyl acetate/hexanes) to give the ethyl ester 53 as a colorless oil.

TLC Rf=0.42 (30% ethyl acetate/hexanes); $^1$H NMR (400 MHz, CDCl$_3$) δ 4.96 (m,1H), 4.19 (q,J=7 Hz, 2H), 4.04 (m,1H), 2.52 (dd, J=15 and 6 Hz, 1H), 2.46 (dd, J=15 and 6 Hz, 1H), 1.44 (s,9H), 1.26 (t,J=7 Hz,3H), 1.21 (d,J=7 Hz, 3H).

Preparation of Ethyl 3(R)-Methyl β-alanine HCl (54)

To a mechanically stirred solution of 53 (2.2 g, 9.7 mmol) in ethyl acetate (180 mL) at −15° C. was vigorously bubbled HCl gas for 30 min. The cooling bath (ethanol/ice) was removed and the solution purged with argon for 1.0 h to remove excess HCl. Concentration furnished the amine HCl 54 as a yellow oil.

$^1$H NMR (400 MHz, D$_2$O) δ 4.23 (q,J=7 Hz,2H), 3.78 (m,1H), 2.79 (m,2H), 1.38 (d,J=7 Hz, 3H), 1.29 (t,J=Hz,3H).

Preparation of
[3(R)-[N-BOC-2-(Piperidin-4-yl)ethyl]-2-piperidone-1]acetyl-3(R)-methyl -β-alanine ethyl ester (55)

To a stirred solution 50 (1.0 g, 2.7 mmol), 54 (0.48 g, 2.8 mmol), HOBT (0.39 g, 2.8 mmol), N(i-pr)$_2$Et (1.5 mL, 8.5 mmol), and dry DMF (100 mL) at −15° C. was added·EDC (0.95 g, 2.8 mmol) followed by removal of the cooling bath. After 20 h the reaction mixture was diluted with ethyl acetate and then washed with H$_2$O, sat. NaHCO$_3$, 5% aqueous KHSO$_4$ and brine, dried (MgSO$_4$), and concentrated. Flash chromatography (silica, ethyl acetate) gave 55 as a colorless oil.

TLC Rf=0.35 (ethyl acetate); $^1$H NMR (300 MHz, CDCl$_3$) δ 6.82 (bd, 1H), 4.32 (m, 1H), 4.13 (q, J=7 Hz, 2H), 4.10 (d,J=15 Hz, 1H), 4.08 (m, 2H), 4.82 (d,J=15 Hz, 1H), 3.36 (m,2H), 2.67 (m,2H), 2.48 (dd, J=5 and 1 Hz,2H), 2.33 (m,1H), 2.00–1.20 (m,11H), 1.45 (s,9H), 1.27 (t,J=7 Hz, 3H), 1.21 (d,J=7 Hz,3H), 1.10 (m,2H).

Preparation of
[3(R)-[N-BOC-2-(Piperidin-4-yl)ethyl]-2-piperidone-1]acetyl-3(R)-methyl -β-alanine (56)

A solution of 55 (1.2 g, 2.5 mmol), 1N NAOH (10 mL, 10 mmol), and CH$_3$OH (18 mL) was stirred at ambient temperature for 1.0 h. The reaction mixture was acidified with 5% aqueous KHSO$_4$ and then extracted with ethyl acetate. The organic portion was then washed with brine, dried (MgSO$_4$), and concentrated. Flash chromatography (silica, 10:0.5:0.5 CHCl$_2$/CH$_3$OH/HOAc) gave the carboxylic acid 56 as a colorless oil after azeotropic removal of residual HOAc with toluene.

TLC Rf=0.40 (10:0.5:0.5 CH$_2$CH$_2$/CH$_3$OH/HOAc); $^1$H NMR (300 MHz, CDCl$_3$) δ 7.02 (bd, 1H), 4.35 (m, 1H), 4.12 (d, J=16 Hz, 1H), 4.08 (m, 2H), 3.87 (d, J=16 Hz, 1H), 3.32 (m, 2H), 2.69 (m, 2H), 2.56 (m,

2H), 2.36 (m, 1H), 2.00–1.25 (m, 11H), 1.45 (s, 9H), 1.03 (m, 2H).

Preparation of [3(R)-[2-Piperidin-4-yl)ethyl]-2-piperidone-1]acetyl-3(R)-methyl-β-alanine (57)

A solution of 56 (0.74 g, 1.6 mmol), trifluoroacetic acid (10 mL), and CH$_2$Cl$_2$ (10 mL) was stirred at ambient temperature for 1.0 h. The reaction mixture was then concentrated and the residual trifluoroacetic acid removed azeotropically with toluene. Flash chromatography (silica, 10:1:1 CH$_3$OH/NH$_4$OH/H$_2$O) afforded 57 as a white amorphous solid. Crystallization of 57 (100 mg) from hot ethanol (4.0 mL) gave 57 (45 mg) as crystals after filtration at ambient temperature.

mp=240°(D); TLC Rf=0.48 (10:1:1 CH$_3$OH/NH$_4$OH/H$_2$O); $^1$H NMR (400 MHz, D$_2$O) δ 4.18 (m,1H), 4.06 (d,J=16 Hz,1H), 3.95 (d,J=16 Hz, 1H), 3.41 (m,4H), 2.99 (m, 2H), 2.45 (m,1H), 3.41 (m,4H), 2.99 (m,2H), 2.45 (m,1H), 2.42 (dd,J=18 and 6 Hz, 1H), 2.33 (dd, J=18 and 7 Hz, 1H), 1.97 (m, 4H), 1.90–1.55 (m,5H), 1.38 (m,4H), 1.19 (d,J=7 Hz, 3H).

Preparation of 1-[2-(N-Boc-Piperidin-4-yl)ethyl]-3-propen-2-yl-(1H-tetrahydropyrimidin-2-one) (59)

To a stirred suspension of 1H-tetrahydropyrimidin-2-one (1.0 g, 10 mM) in DMF (50 ml) was added a 1.0 molar solution of lithium bis (trimethylsilyl)amide (10 ml, 10 mM). After ½ hour, allyl bromide (1.0 ml, 1.17 mM) was added and stirring was continued for 1 hour. A second charge of lithium bis(trimethylsilyl)amide (10 ml, 10 mM) was added followed after ½ hour by the addition of (N-Boc-piperidin-4-yl) ethyl iodide (10). The reaction was stirred at 25° C. overnight. The reaction mixture was poured into ice and 15% KHSO$_4$ (50 ml), extracted with ether (2×100 ml) washed with H$_2$O (2×100 ml), brine, dried over Na$_2$SO$_4$ and evaporated in vacuo. Flash chromatography on SiO$_2$ (ethyl acetate-hexane 1:1) afforded pure 59.

$^1$H NMR (300 MHz, CDCl$_3$) δ 1.14 (2H, m), 1.46 (9H, s), 1.74 (3H, m), 1.95 (2H, m) 2.68 (2H, t), 3.22 (4H, m), 3.38 (2H, m), 3.95 (2H, m), 4.06 (2H, m), 5.13 (2H, dd).

Preparation of 1-[2-(N-Boc-Piperidin-4-yl)ethyl]-3-acetaldehyde-(1H-tetrahydropyrimidin-2-one) (60)

To a stirred solution of 59 (430 mg, 1.27 mm) in THF (7 ml), H$_2$O (5 ml) and sodium periodate (0.68 g, 3.19 mM) was added a 2.5% solution of osmium tetroxide in 2-methyl-2-propanol (413 μl, 1.28 mM). After stirring for 4 hours, ethyl acetate (70 ml) was added and the mixture washed with 50% brine/10% sodium sulfate (1:1) then with brine. The solution was dried over Na$_2$SO$_4$ and evaporated in vacuo to give 60.

Preparation of 1-[2-(N-Boc-Piperidin-4-yl)ethyl]-3-acetic acid-(1H-tetrahydropyrimidin-2-one) (61)

A solution of 60 (374 mg) in acetone (7 ml) was cooled to −15° C. then treated dropwise with Jones reagent until an orange color persisted for 5 minutes. Ethyl acetate (60 ml) was added and the solution washed with H$_2$O, brine, dried over Na$_2$SO$_4$, then evaporated in vacuo to give 61. $^1$H NMR (300 MHz, CDCl$_3$) δ 1.12 (2H, m), 1.45 (9H, s), 1.70 (2H, bd), 2.03 (2H, m), 2.70 (2H, bt), 3.37 (4H, m), 3.95 (2H, m), 4.05 (2H, m).

Preparation of [1-[2-(N-Boc-Piperidin-4-yl)ethyl]-(1H-tetrahydropyrimidin-2-one)-3]-acetyl-3 (R)-(2-phenylethyl)β-alaninemethylester (63)

A mixture of 61 (125 mg, 0.34 mM), (R)-3-(2-phenylethyl)β-alanine methyl ester hydrochloride (83 mg, 0.34 mM) (62), 1-hydroxybenzotriazole hydrate (48.3 mg, 0.35 mM), 1-ethyl-3-(3-dimethylaminopropyl)carbodiimide hydrochloride (70 mg, 0.37 mM) and triethyl amine (107 μl, 0.77 mM) in dry DMF (1.6 ml) was stirred at 25° C. for 18 hours. The reaction mixture was poured into ice H$_2$O, extracted with ethyl acetate (2×50 ml), washed with 10% citric acid, brine, dried over Na$_2$SO$_4$ and evaporated in vacuo to give 63. $^1$H NMR (300 MHz, CDCl$_3$) δ 1.14 (2H, m), 1.45 (9H, s), 1.70 (2H, m), 1.86 (2H, m), 2.02 (2H, m), 2.58 (2H, d), 2.66 (3H, m), 3.36 (5H, m), 3.68 (2H, m), 3.93 (1H, d), 4.07 (2H, m), 7.02 (1H, m), 7.20 (2H, m), 7.29 (2H, m).

Preparation of 1-[2-(N-Boc-Piperidin-4-yl)ethyl]-(1H-tetrahydropyrimidin-2-one)-3]-acetyl-3 (R)-(2-phenylethyl)δ-alanine (64)

A solution of 63 (168 mg, 0.31 mM) in THF (15 ml) and H$_2$O (15 ml) was cooled to 0° C., treated with 1N LiOH (1.2 ml) then stirred at 25° C. overnight. The THF was evaporated at reduced pressure, the residue acidified with 10% citric acid, extracted with ethyl acetate (2×50 ml) washed with brine, dried over Na$_2$SO$_4$ and evaporated in vacuo to give 64.

Preparation of [1-(2-piperidin-4-yl)ethyl]-[(1H-tetrahydropyrimidin-2-one)-3]-acetyl-3(R) -(2-phenylethyl)β-alanine (65)

A solution of 64 (128 mg) in methylene chloride (8 ml) and anisole (1.5 ml) was cooled to −20° C. then treated with triflxioroacetic acid (8 ml) over a 5 minute period. The reaction mixture was stirred at −5° C. for 1 hour then evaporated in vacuo. The residue was chromatographed on SiO$_2$ (ethanol-H$_2$O-NH$_4$OH, 10:1:1) to give 65.

Analysis Calc for C$_{24}$H$_{36}$N$_4$O$_4$·2.5H$_2$O C, 57.84; H, 8.65; N, 11.73. Found: C, 57.94; H, 8.39; N, 11.47.

Preparation of [1-(2-piperidin-4-yl)ethyl]-[(1H-tetrahydropyrimidin-2-one)-3]-acetyl-3(R) -(2-indol-3-yl)-ethyl]β-alanine (66)

By following substantially the procedure described for preparing 63 but substituting for the 3(R)-(2-phenylethyl)β-alanine methyl ester hydrochloride described therein an equivalent amount of 3R-[2-(indol-3-ethyl]β-alanine ethyl ester and following the procedures described for preparing 64 and 65, there is obtained 66.

Analysis Calc for C$_{26}$H$_{37}$N$_5$O$_4$: C, 56.3; H, 8.0; N, 12.6. Found: C, 56.3; H, 7.9; N, 12.2.

Preparation of [1-(2-piperidin-4-yl)ethyl-(1H-tetrahydropyrimidin-2-one)-3]-acetyl-3(R)-methyl β-alanine (67)

By following substantially the procedure described for preparing 63 but substituting for the (R)-3-(2-phenylethyl)β-alanine methyl ester hydrochloride described therein an equivalent amount of ethyl 3(R)-methylβ-alanine hydrochloride and following the procedures described for preparing 64 and 65, there is obtained 67.

Preparation of [1-(2-piperidin-4-yl)ethyl]-[(1H-tetrahydropyrimidin-2-one)-3]-acetyl-2(R)-[butylsulfonylaminol] β-alanine (68)

By following substantially the procedure described for preparing 63 but substituting for the (R)-3-(2-phenylethyl)β-alanine methyl ester hydrochloride described therein an equivalent amount of ethyl 2(S)-butylsulfonylamino β-alanine hydrochloride and following the procedures described for preparing 64 and 65, there is obtained 68.

Preparation of Methyl 4(R)-Benzyl-2-oxazolidinonesuccinate (70)

To a stirred solution of mono-methyl succinate 69 (3.7 g, 28.2 mmol), NEt$_3$ (4.0 mL, 28.2 mmol) and dry THF (160 mL) at −78° C. was added trimethylacetyl chloride (3.6 mL, 28.2 mmol) dropwise. After 10 min, the cooling bath was removed and replaced with an icebath. After 1.0 hour, the heterogeneous mixture was recooled to −78° C., and treated, via cannula addition, with lithium (R)-(+)-4-benzyl-2-oxazolidinone (28.2 mmol) in dry THF (43 mL), prepared by treating (R)-(+)-4-benzyl-2-oxazolidinone oxazolidinone (5.0 g, 28.2 mmol) in dry THF (43 mL) at −78° C. with n-BuLi (17.8 mL, 28.2 mmol, 1.6 M/hexanes). After addition was complete, the reaction mixture was warmed to room temperature overnight. The reaction mixture was diluted with ethyl acetate and washed with H$_2$O, sat. NaHCO$_3$, 5% aqueous KHSO$_4$ and brine, dried MgSO$_4$ and concentrated. Flash chromatography (silica, 20% ethyl acetate/hexanes) gave 70 as a white crystalline solid. TLC Rf=0.48 (30% ethyl acetate/hexanes); $^1$H NMR (300 MHz, CDCl$_3$) δ 7.30 (m, 5H), 4.68 (.m, 1H), 4.21 (m, 2H), 3.72 (s, 3H), 3.28 (m, 3H), 2.80 (dd, J=13 and 4 Hz, 1H), 2.73 (m, 2H).

Preparation of Methyl 4(R)-Benzyl-2-oxazolidinone-2(R)-(2-cyanoethyl)succinate (71)

To a stirred solution of TiCl$_4$ (12.3 mL, 12.3 mmol, 1M/CH$_2$Cl$_2$) and dry CH$_2$Cl$_2$ (83 mL) at 0° C. was added titanium (IV) isopropoxide (1.2 mL, 4.1 mmol). After 15 min, diisopropylethylamine (3.0 mL, 17.3 mmol) was added dropwise to form a dark brown solution. After 10 minutes, 70 (4.8 mg, 16.5 mmol) was added followed by continued stirring at 0° C. for 1 hour. Acrylonitrile (4.3 mL, 66 mmol) was added dropwise to the dark solution followed by stirring at 0° C. for 72 hours. The reaction mixture was quenched with sat. NH$_4$Cl at 0° C., then extracted with CH$_2$Cl$_2$. The combined organic extracts were washed with saturated NaHCO$_3$ and brine, dried MgSO$_4$ and concentrated. Flash chromatography (silica, 25% ethyl acetate/hexanes) gave 71 as a crystalline solid. TLC Rf=0.22 (30% ethyl acetate/hexanes); $^1$H NMR (300 MHz, CDCl$_3$) δ 7.40-7.20 (m, 5H), 4.70 (m, 1H), 4.25 (m, 2H), 4.13 (m, 1H), 3.67 (s, 3H), 3.30 (dd, J=13 and 4 Hz, 1H), 2.93 (dd, J=17 and 10 Hz, 1H), 2.80 (dd, J=17 and 10 Hz, 1H), 2.55 (dd, J=13 and 4Hz, 1H), 2.43 (t, J=7 Hz, 2H), 2.10 (m, 1H), 1.90 (m, 1H).

Preparation of Methyl 4(R)-Benzyl-2-oxazolidinone-2(R)-(3-aminopropyl)succinate (72)

A mixture of 71 (2.0 g, 5.8 mmol), PtO$_2$ (0.8 g), CH$_3$OH (50 mL), and CHCl$_3$ (5 mL) were shaken on the Parr apparatus under a hydrogen atmosphere (60 PSI) at ambient temperature for 3 hours. The reaction mixture was filtered through a celite pad and then concentrated to furnish the crude amine HCl 72 as a yellow oil.

TLC Rf=0.50 (CH$_2$Cl$_2$/CH$_3$OH/AcOH 9:1:1)

Preparation of Methyl [2-Piperidone-3(R)]acetate (73)

The crude amine HCl 72 (2.0 g, ~5.8 mmol), acetonitrile (250 mL) and NaHCO$_3$ (5 g) were stirred overnight at ambient temperature. The reaction mixture was then filtered and the filtrate concentrated. Flash chromatography (silica, ethyl acetate) gave lactam 73 as a colorless crystalline solid. TLC Rf=0.22 (ethyl acetate); $^1$H NMR (300 MHz, CDCl$_3$) δ 5.82 (bs, 1H), 3.70 (s, 3H), 3.33 (m. 2H), 2.88 (dd, J=16 and 4 Hz, 1H), 2.75 (m, 1H), 2.58 (dd, J=16 and 7 Hz, 1H), 2.10-1.60 (m, 4H).

Preparation of Methyl [1-[N-Boc-2-(Piperidin-4-yl)-ethyl]-2-piperidone-3(R)]acetate (74)

To a stirred solution of 73 (1.1 g, 6.4 mmol) in anhydrous DMF (60 mL) at −15° C. was added NaN(TMS)$_2$ (6.4 mL, 6.4 mmol, 1M/hexanes) dropwise followed by removal of the cooling bath. After 10 minutes the iodide 10 (2.3 g, 7.0 mmol) was added and stirring continued at ambient temperature for 4 hours. The reaction mixture was then diluted with ethyl acetate and washed with H$_2$O (2×) and brine, dried (MgSO$_4$), and concentrated. Flash chromatography (silica, 40% ethyl acetate/hexanes) gave 74 as an oil. TLC Rf=0.29 (40% ethyl acetate/hexanes).

Preparation of [1-[N-Boc-2-(piperidin-4-yl)ethyl]-2-piperidone-3(R)]acetic acid (75)

Utilizing the procedure for converting 49 to 50, 74 (0.44 g, 1.1 mmol) furnished 75 as an oil. TLC Rf=0.52 (CH$_2$Cl$_2$/CH$_3$OH/AcOH 9:0.5:0.5).

Preparation of [1-[N-Boc-2-(piperidin-4-yl)ethyl]-2-piperidone-3(R)]acetyl-3(R)-methyl -β-alanine ethyl ester (76)

Utilizing the procedure for converting 50 to 55, 75 (0.40 g, 1.1 mmol) was coupled to 54 (0.27 g, 1.6 mmol) to afford 76 as an oil after flash chromatography (silica, ethyl acetate). TLC Rf=0.20 (ethyl acetate).

Preparation of [1-[N-(Boc-2-(piperidin-4-yl)ethyl]-2-piperidone-3(R)]acetyl-3(R)-methyl -β-alanine (77)

Utilizing the procedure for converting 55 to 56, 76 (0.30 g, 0.64 mmol) gave 77 as an oil. TLC Rf=0.24 (CH$_2$Cl$_2$/CH$_3$OH/AcOH 9:0.5:0.5); $^1$H NMR (400 MHz, CDCl$_3$) δ 6.93 (m, 1H), 4.32 (m, 1H), 4.06 (m, 2H), 3.35 (m, 2H), 3.29 (m, 2H), 2.70-2.50 (m, 6H), 2.38 (m, 1H), 2.00-1.20 (m, 9H), 1.45 (s, 9H), 1.27 (d, J=6 Hz, 3H), 1.06 (m, 2H).

Preparation of [1-[2-(Piperidin-4-yl)ethyl]-2-piperidone-3(R)-methyl-β-alanine (78)

Utilizing the procedure used to convert 56 to 57, 77 (0.24 g, 0.53 mmol) gave 78 as an amorphous solid after flash chromatography (silica, 10:1:1 ethanol/H$_2$O/N-H$_4$OH). $^1$H NMR (400 MHz, D$_2$O) δ 4.19 (m, 1H), 3.40 (m, 6H), 3.00 (m, 2H), 2.70 (m, 1H), 2.64 (m, 1H), 2.47 (m, 2H), 2.30 (dd, J=14 and 8 Hz, 1H), 2.00 (m, 2H), 1.92 (m, 2H), 1.79 (m, 1H), 1.61 (m, 4H), 1.45 (m, 2H), 1.18 (d, J=7 Hz, 3H).

Preparation of N-Cbz-Gly-3(R)-methyl-J3-alanine ethyl ester (79)

A stirred solution of Cbz-Gly (0.94 g, 4.5 mmol), 4-methylmorpholine (1.1 mL, 4.9 mmol), and ethyl acetate (50 mL) at −15° C. was treated with isobutyl chloroformate (0.61 mL, 4.7 mmol) in one portion. After 15 min, 54 (0.75 g, 4.5 mmol) in ethyl acetate (1 mL) was added followed by warming to ambient temperature overnight. The reaction mixture was then washed with 1M NaHSO$_4$, brine, sat. NaHCO$_3$ and brine, dried (MgSO$_4$), and concentrated to afford 79 as a yellow oil. $^1$H NMR (300 MHZ, CDCl$_3$) δ 7.48 (m, 5H), 6.73 (m, 1H), 5.58 (m, 1H), 5.13 (s, 2H), 4.48 (m, 1H), 4.30 (q, J=7 Hz, 2H), 3.95 (m, 2H), 2.62 (m, 2H), 1.37 (t, J=7 Hz, 3H).

Preparation of Gly-3(R)-methyl-β-alanine ethyl ester acetic acid salt (80)

A mixture of 79 (1.4 g, 4.5 mmol), 10% ACOH/CH$_3$OH (50 mL), and 20% Pd(OH)$_2$ (0.14 g) was shaken on the Parr apparatus under a hydrogen atmosphere (60 PSI) overnight. After 24 hours the reaction mixture was filtered through a celite pad and the filtrate concentrated. Flash chromatography (silica, 5:3:1 CH$_2$Cl$_2$/ethanol/AcOH) to give 80 as an amorphous solid. TLC Rf=0.41 (5:3:1 CH$_2$Cl$_2$/ethanol/AcOH).

Preparation of 4(S)-Benzyl-2-oxazolidinone-4-(N-Boc-piperidin-4-yl)-2(R)-(-prop-2-ene)butyrate (81)

To a stirred solution of 45 (2.5 g, 5.8 mmol) in THF (50 ml) at −78° C. was added lithium bis(trimethylsilyl)amide (7.0 mL, 7.0 mmol, 1M/hexanes) followed by allyl bromide (2.5 mL, 29 mmol). The cooling bath was then removed and the reaction stirred at 0° C. for 1.5 hours. The reaction was quenched with sat. NH$_4$Cl, then diluted with EtOAc followed by washing with sat. NaHCO$_3$, 5% KHSO$_4$, and brine, drying (MgSO$_4$) and concentration. Flash chromatography (silica, 15% EtOAc/hexanes) afforded 81 as a colorless oil. TLC Rf=0.53 (30% EtOAc/hexanes); $^1$H NMR (300 MHz, CDCl$_3$) δ 7.40–7.20 (m, 5H), 5.82 (m, 1H), 5.10 (m, 2H), 4.80 (m, 1H), 4.20 (m, 2H), 4.07 (m, 2H), 3.90 (m, 1H), 3.31 (dd, J=13 and 3Hz, 1H), 2.68 (m, 2H), 2.48 (m, 1H), 2.35 (m, 1H), 1.90–1.20 (m, 7H), 1.47 (s, 9H), 1.10 (m, 2H).

Preparation of 4-(N-Boc-Piperidin-4-yl)-2(R)-(prop-2-ene)butyric acid (82)

To a stirred solution of 81 (1.8 g, 3.8 mmol), 30% H$_2$O$_2$ (8.5 ML, 83 mmol), THF (41 mL) and H$_2$O (12 mL) at ambient temperature was added LIOH (14 mL, 14 mmol, 1N). After 2h the excess LIOH was quenched with 10% NaHSO$_4$ dropwise at 0° C. The reaction was then acidified with 5% KHSO$_4$ and extracted with EtOAc. The EtOAc portion was then washed with brine, dried (MgSO$_4$), and concentrated to give 82 as a colorless oil. TLC R$_f$=0.79 (10% CH$_3$OH/EtOAC).

Preparation of [4-(N-Boc-Piperidin-4-yl)-2(R)-(prop-2-ene)butyrate]-Gly-3(R)-methyl-β-alanine ethyl ester (83)

Utilizing the procedure for converting 50 to 55, 82 (1.3 g, 2.5 mmol) was coupled to 80 (0.62 g, 2.5 mmol) to give 83 after flash chromatography (silica, 10% isopropanol/hexanes). TLC Rf=0.50 (20% isopropanol/hexanes); $^1$H NMR (300 MHz, CDCl$_3$) δ 6.67 (bd, J=8 Hz, 1H), 6.37 (m, 1H), 5.72 (m, 1H), 5.02 (m, 1H), 4.35 (m, 1H), 4.13 (q, J=7 Hz, 2H), 4.03 (m, 1H), 3.88 (m, 2H), 2.63 (m, 2H), 2.51 (m, 2H), 2.35 (m, 1H), 2.20 (m, 2H), 1.70–1.20 (m, 7H), 1.44 (s, 9H), 1.26 (t, J=7 Hz, 3H), 1.07 (m, 2H).

Preparation of [3-[2-(N-Boc-Piperidin-4-yl)ethyl]-5-hydroxy-2-pyrrolidinone-1]acetyl-3(R)-methyl-62-alanine ethyl ester (84)

To a solution of 83 (0.74 g, 1.5 mmol), THF (12.2 mL), H$_2$O (9.2 mL), and NaIO$_4$ (0.82 g, 3.8 mmol) was added OsO$_4$ (0.96 mL, 80 μmol; 2.5% tert-butanol) at ambient temperature. After 2.0 hours, the reaction mixture was diluted with ether and then washed with H$_2$O, 10% aqueous Na$_2$S$_2$O$_3$, and brine, dried (MgSO$_4$), and concentrated to give 84 as a yellow oil. TLC Rf=0.26 (20% isopropanol/hexanes).

Preparation of [3-[2-(N-Boc-Piperidin-4-yl)ethyl]-5-hydroxy-2-pyrrolidinone-1]acetyl-3(R)-methyl-β-alanine (85)

Utilizing the procedure for converting 55 to 56, 84 (0.73 g, 1.5 mmol) gave 85 as a pale yellow foam. $^1$H NMR (300 MHz, CDCl$_3$) δ 5.23 (d, J=5 Hz, 1H), 4.58 (d, J=16 Hz, 1H), 4.32 (m, 1H), 4.05 (m, 2H), 3.70 (d, J=16 Hz, 1H), 2.80–2.40 (m, 6H), 2.22 (m, 1H), 2.00–1.00 (m, 9H), 1.45 (s, 9H), 1.27 (d, J=7 Hz, 3H).

Preparation of [3-[2-(Piperidin-4-yl)ethyl]-2-pyrrolidinone-1]acetyl-3(R)-methyl-β-alanine (85)

A stirred solution of 85 (0.61 g, 1.3 mmol) in CH$_2$Cl$_2$ (50 mL) at ambient temperature was treated with a solution of CF$_3$CO$_2$H (5.8 mL) and triethylsilane (0.8 mL, 5.2 mmol). After 2.0 h the reaction mixture was concentrated followed by azeotropic removal of residual CF$_3$CO$_2$H with toluene. Flash chromatography (silica, 10:1:1 ethanol/H$_2$O/NH$_4$OH) gave 86 as a colorless solid. TLC Rf=0.17 (9:1:1 ethanol/H$_2$O/NH$_4$OH); $^1$H NMR (300 MHz, CD$_3$OD) δ 4.20 (m, 1H), 3.97 (d, J=17 Hz, 1H), 3.85 (d, J=17 Hz, 1H), 3.40 (m, 4H), 2.95 (m, 2H), 2.52 (m, 1H), 2.30 (m, 2H), 2.00–1.30 (m, 11H), 1.20 (d, J=7 Hz, 3H).

Preparation of 2-(2,3,4,5,6-Tetrahydro-1,1-dioxo-2H-1,2-thiazin-2-yl)prop-2-ene (88)

To a solution of 87 (J.O.C. 52, p. 2162 (1987) E. H. White, H. M. Lim) (0.35 g, 2.6 mmol) in DMF at 0° C. was added NaN(TMS)$_2$ (3.9 mL, 3.9 mmol); 1M/hexanes) dropwise. After 30 min, allyl bromide (0.45 mL, 5.2 mmol) was added in one portion followed by continued stirring for 30 min. The reaction mixture was diluted with ethyl acetate and washed with sat. NH$_4$Cl and brine, dried (MgSO$_4$), and concentrated. Flash chromatography (silica, 30% ethyl acetate/hexanes) gave 88 as a colorless oil. TLC Rf=0.29 (30% ethyl acetate/hexanes); $^1$H NMR (300 MHz, CDCl$_3$) δ 5.80 (m, 1H), 5.25 (m, 2H), 3.78 (m, 2H), 3.30 (m, 2H), 3.02 (m, 2H), 2.21 (m, 2H), 1.68 (m, 2H).

Preparation of 2-[6-[2-(N-Boc-Piperidin-4-yl)ethyl]-(3,4,5,6-tetrahydro-1,1-dioxo-2H-1,2-thiazin-2-yl)]-prop-2-ene (89)

A stirred solution of 88 (0.34 g, 1.93 mmol) in THF (10 mL) at −78° C. was treated dropwise with n-BuLi (1.45 mL, 2.3 mmol; 1.6 M/hexanes). After 30 min the reaction mixture was treated sequentially with 1-methyl-2-pyrrolidinone (1 mL) and 10 (0.86 g, 2.7 mmol) in THF (10 mL), followed by warming to −23° C. After 2 hours at −23° C. the reaction was quenched with saturated NH$_4$Cl then diluted with ethyl acetate and washed with H$_2$O and brine, dried (MgSO$_4$), and concentrated. Flash chromatography (silica, 30% ethyl acetate/hexanes) gave 89 as a crystalline solid. TLC Rf=0.27 (30% ethyl acetate/hexanes); $^1$H NMR (400 MHz, CDCl$_3$) δ 5.80 (m, 1H), 5.25 (m, 2H), 4.07 (m, 2H), 3.78 (m, 2H), 3.34 (m, 2H), 3.17 (m, 1H), 3.02 (m, 1H), 2.82 (m, 2H), 2.66 (m, 2H), 2.24–2.04 (m, 3H), 1.89 (m, 1H), 1.70–1.35 (m, 7H), 1.08 (m, 2H).

Preparation of 2-[6-[2-(N-Boc-Piperidin-4-yl)ethyl]-(3,4,5,6-tetrahydro-1,1-dioxo-2H-1, 2-thiazin-2-yl)]-acetaldehyde (90)

To a stirred solution of 89 (0.50 g, 1.29 mmol), THF (16 mL), H$_2$O (12 mL), and NaIO$_4$ (0.69 g, 3.2 mmol) was added OsO$_4$ (1 mL, 0.1 mmol; 2.5 %/tertbutanol) to effect a white precipitate. After 3.0 h, the reaction mixture was diluted with ethyl acetate and washed with H$_2$O, 5% KHSO$_4$, sat. NaHCO$_3$ and brine, dried (MgSO$_4$), and concentrated to give aldehyde 90 as an oil. $^1$H NMR (400 MHz, CDCl$_3$) δ 9.64 (s, 1H), 4.08 (m, 2H), 4.00 (d, J=17 Hz, 1H), 3.89 (d, J=17 Hz, 1H), 3.62 (m, 1H), 3.14 (m, 1H), 2.96 (m, 1H), 2.66 (m, 2H), 2.20 (m, 1H), 2.08 (m, 1H), 2.00–1.35 (m, 9H), 1.10 (m, 2H).

Preparation of 2-[6-[2-(N-Boc-Piperidin-2-yl)ethyl]-(3,4,5,6-tetrahydro-1,1-dioxo-2H-1,2-thiazin-2-yl)]-acetic acid (91)

A stirred solution of 90 (0.44 g, 1.13 mmol) in acetone (10 mL) at 0° C. was treated with Jones Reagent (1.0 mL) in 3 portions. After 5 min, excess Jones Reagent was quenched with i-propanol and then diluted with H$_2$O. The reaction mixture was then extracted with ethyl acetate and the organic extract washed with brine, dried (MgSO$_4$), and concentrated. Flash chromatography (silica, 20:1:1 CH$_2$Cl$_2$/CH$_3$OH/ACOH) gave 91 as a light yellow oil. TLC Rf=0.45 (20:1:1 CH$_2$Cl$_2$/CH$_3$OH/AcOH).

Preparation of 2-[6-[2-(N-Boc-Piperidin-4-yl)ethyl]-(3,4,5,6-tetrahydro-1,1-dioxo-2H-1, 2-thiazin-2-yl)]-acetyl-3(R)-methyl-β-alanine ethyl ester (92)

Utilizing the procedure for converting 50 to 55, 91 (98 mg, 0.24 mmol) was coupled to 54 (120 mg, 0.71 mmol) to afford 92 as a yellow oil after flash chromatography (silica, ethyl acetate). TLC Rf=0.28 (ethyl acetate); $^1$H NMR (300 MHz, CDCl$_3$) δ 7.08 (m, 1H), 4.37 (m, 1H), 4.08 (m, 2H), 3.89 (d, J=17 Hz, 1H), 3.77 (d, J=17 Hz, 1H), 3.60 (m, 1H), 3.15 (m, 1H), 2.88 (m, 1H), 2.68 (m, 2H), 2.52 (m, 2H), 2.20–1.00 (m, 13H), 1.27 (t, J=7 Hz, 3H), 1.25 (t, J=7 Hz, 3H).

Preparation of 2-[6-[2-(N-BOC-Piperidin-4-yl)ethyl]-(3,4,5,6-tetrahydro-1,1-dioxo-2H-1,2 -thiazine-2-yl)]acetyl-3(R)-methyl-β-alanine (93).

Utilizing the procedure for converting 55 to 56, 92 (76 mg, 0.15 mmol) gave 93 as an oil. TLC Rf=0.42 (20:1:1 CH$_2$Cl$_2$/CH$_3$OH/AcOH); $^1$H NMR (300 MHz, CDCl$_3$) δ 7.20 (m, 1H), 4.39 (m, 1H), 4.10 (q, J=7 Hz, 2H), 4.08 (m, 2H), 3.92 (d, J=17 Hz, 1H), 3.74 (m, 1H), 3.53 (m, 1H), 3.15 (m, 1H), 2.90 (m, 1H), 2.77 (m, 2H), 2.59 (m, 2H), 2.10 (m, 1H), 2.10–1.10 (m, 12H), 1.27 (t, J=7 Hz, 3H), 1.25 (t, J=7 Hz, 3H).

Preparation of 2-[6-[2-(Piperidin-4-yl)ethyl]-(3,4,5,6-tetrahydro-1,1-dioxo-2H-1,2 -thiazin-2-yl)]acetyl-3-(R)-methyl-β-alanine (94).

Utilizing the procedure for converting 56 to 57, 93 (61 mg, 0.12 mmol) gave 94 as an off-white solid after flash chromatography (silica, 10:1:1 ethanol/NH$_4$OH/H$_2$O). TLC Rf=0.26 (10:1:1 ethanol/NH$_4$OH/H$_2$O); $^1$H NMR (300 MHz, D$_2$O) δ 4.08 (m, 1H), 3.71 (m, 2H), 3.40 (m, 1H), 3.29 (m, 2H), 3.14 (m, 2H), 2.83 (m, 2H), 2.25 (m, 2H), 2.12 (m, 1H), 1.90–1.20 (m, 12H), 1.05 (d, J=7 Hz, 3H).

1-[2-(N-BOC-piperidin-4-yl)ethyl]-3-propanol-2-pyrrolidinone (95)

A solution of 20 (1.20 g, 3.6 mmol) in THF (3 ml) was added to a solution of borane-dimethyl sulfide (3.6 mmol) in 3 ml THF at 0° C. and this was stirred for 2.5 hr at 0°. Then, H$_2$O (0.15 ml), 10N aqueous NaOH solution (0.65 ml), THF (1 ml), and C$_2$H$_5$OH (0.36 ml) were added at 0° and with stirring the reaction mixture was warmed to 23° and treated with 30% H$_2$O$_2$ (0.36 ml). This solution was heated to 55° C. and stirred for 2 hours. The reaction mixture was cooled, saturated with K$_2$CO$_3$ an the organic phase was separated, dried (MgSO$_4$) and the solvent removed. The resulting residue was purified by flash chromatography on silica gel eluting with 10% MeOH/EtOAc to give 95. R$_f$ 0.3 (silica gel, 10% MeOH/EtOAc. 1-[2-(N-BOC-piperidin-4-yl)ethyl]-3-propanoic-acid-2-pyrrolidinone (96)

A solution of 95 (1.14 mmol) in acetone (5 ml) was cooled to −15° and treated with Jones reagent until the color remained amber/brown. The reaction mixture was diluted with saturated NaHCO$_3$ solution to pH 9 and this was extracted with EtOAc. The aqueous phase was acidified to pH 3 with KHSO$_4$ solution and extracted with several portions of EtOAc. The combined organic extracts were dried (MgSO$_4$) and the, solvent removed to give 96. R$_f$ 0.3 (silica gel, 9/1/1 CH$_2$Cl$_2$/MeOH/HOAc).

[1-[2-(N-BOC-piperidin-4-yl)ethyl]-2-pyrrolidinone-3]proyanoyl-β-alanine ethyl ester (97)

A solution of 96 (0.55 mmol), β-alanine ethyl ester HCl (0.825 mmol), N-methylmorpholine (1.65 mmol) in CH$_3$CN (5 ml) at 23° was treated with BOP (0.825 mmol) and the resulting solution was stirred for 48 hrs. The reaction mixture was diluted with EtOAc, washed with 10% KHSO$_4$ brine, H$_2$O brine, dried (MgSO$_4$) and the solvent removed. The residue was purified by flash chromatography on silica gel eluting with 30% acetone/hexane to give 97 as a clear oil. R$_f$ 0.25 (silica gel, 30% acetone/hexane).

[1-[2-(N-BOC-piperidin-4-yl)ethyl]-2-pyrrolidinone-3]propanoyl-β-alanine (98)

A solution of 97 (0.29 mmol), LiOH-H₂O (1.45 mmol), THF/MeOH/H₂O (1:1:1, 3 ml) was stirred for 2 hours. This was diluted with EtOAc and washed with 10% KHSO₄, H₂O, brine and dried (MgSO₄). Solvent removal gave 98 as an oil. Rf 0.5 (silica gel, 9/1/1 CH₂Cl₂/MeOH/HOAc).

[1-[2-(Piperidin-4-yl)ethyl]-2-pyrrolidinone-3]propanoyl-β-alanine HCl (99)

A solution of 98 (0.18 mmol) in EtOAc (2 ml) was cooled to −78° and treated with HCl gas. After 0.5 hr the solvent was removed to give 99 as a white solid. Rf 0.22 (silica gel, 10/1/1 EtOH, NH₄OH, H₂O).

Preparation of N-BOC-4-piperidine methyl iodide (101)

Utilizing the procedure for converting 9 to 10, 100 (12.3 g, 57 mmol) (Carr et al., EP 317997, May 31, 1989), gave 101 after flash chromatography (silica gel, 15% EtOAc/hexane). Rf 0.38 (silica gel, 10% EtOAc/hexanes). ¹H NMR (300 MHz, CDCl₃) δ 1.15 (2H, m), 1.48 (9H, s), 1.62 (1H, m), 1.84 (2H, m), 2.70 (2H, m), 3.11 (2H, m), 4.12 (2H, m).

Preparation of N-BOC-piperidinemethyltriphenylphosphonium iodide (102)

A solution of 101 (5.1 g, 15.7 mmol), CH₃CN (75 mL), and triphenylphosphine (4.5 g, 17.3 mmol) was heated at 80° C. for 60 h. The cooled reaction mixture was concentrated and the residual oil triturated with ether, then placed under vacuum to give 102 as a yellow foam. ¹H NMR (CDCl₃, 300 MHz) δ 7.31 (m, 15H), 4.10 (m, 2H), 3.97 (m, 2H), 2.69 (m, 2H), 2.00–1.10 (m, 5H), 1.48 (s, 9H).

Preparation of 3-[2-(N-BOC-piperidin-4-yl)ethylene]-2-(methoxy)pyridine (104)

To a suspension of 102 (5.0 g, 8.5 mmol) in dry THF at 0° C. was added NaN(TMS)₂ (9.4 mL, 9.4 mmol, 1M/hexanes) dropwise. After 15 min. a solution of 103 (0.97 g, 7.0 mmol) (Tetrahedron Letters (1988) 29, 773) in THF (3 mL) was added dropwise to the yellow/orange homogeneous reaction mixture. After 1h the cooling bath was removed followed by continued stirring for 30 min. The reaction was quenched with H₂O and ether. The aqueous phase was reextracted with ether, the organic layers combined and then washed with brine, dried (Na₂SO₄) and concentrated. Flash chromatography (silica, 15% ethyl acetate/hexanes) gave 104 as a colorless oil. TLC Rf=0.15 (10% ethyl acetate/hexanes) ¹H NMR (300 MHz, CDCl₃) δ 8.09 (dd, J=5 and 2 Hz, 1H), 7.42 (dd, J=7 and 2 Hz, 1H), 6.87 (dd, J=7 and 5 Hz, 1H), 6.37 (d, J=12 Hz, 1H), 5.58 (dd, J=12 and 10 Hz, 1H), 4.10 (m, 2H), 3.95 (s, 3H), 2.70 (m, 2H), 2.50 (m, 1H), 1.80–1.20 (m, 4H), 1.47 (s, 9H).

Preparation of 3-[2-(N-BOC-piperidin-4-yl)ethyl]-2-methoxypyridine (105)

A mixture of 104 (1.4 g, 4.3 mmol), ethyl acetate (22 mL) and 10% Pd/C (0.27 g, 20%/wt) was stirred under a hydrogen atmosphere (1 atm) at ambient temperature for 4 h. The reaction mixture was filtered through a celite pad and the filtrate concentrated to give 105 as a cloudy colorless oil. TLC Rf=0.17 (10% ethyl acetate/hexanes); ¹H NMR (CDCl₃, 300 MHz) δ 8.02 (dd, J=5 and 2 Hz, 1H), 7.36 (dd, J=7 and 2 Hz, 1H), 6.80 (dd, J=7 and 5 Hz, 1H), 4.10 (m, 2H), 3.94 (s, 3H), 2.69 (m, 2H), 2.58 (m, 2H), 1.72 (m, 2H), 1.55–1.35 (m, 3H), 1.48 (s, 9H), 1.13 (m, 2H).

Preparation of 3-[2-(N-BOC-piperidin-4-yl)ethyl]-2-pyridon-1-yl (106)

To a solution of 105 (0.81 g, 2.5 mmol) in dry CH₃CN (13 mL) was added NaI (0.94 g, 6.3 mmol) followed by chlorotrimethylsilane (0.80 mL, 6.3 mmol). The resulting opaque yellow solution was heated at 60° C. for 2.0 h. The cooled reaction mixture was quenched with methanol (50 mL), stirred for 10 min. and then concentrated. The residue was dissolved in dioxane/H₂O (6.7 mL/3.3 mL) then treated with 1N NaOH (5.0 mL, 5.0 mmol). The solution was cooled to 0° C. and then treated with BOC₂O (1.1 g, 5.0 mmol) followed by removal of the cooling bath. After stirring overnight the dioxane was evaporated and the residue diluted with H₂O (10 mL) and ethyl acetate (50 mL), followed by acidification to pH~1.0 with 20% KHSO₄. The organic phase was separated and then washed with H₂O and brine, dried (MgSO₄) and concentrated. Flash chromatography (silica, 2:1 CH₂Cl₂/acetone) gave 106 as a pale yellow solid. TLC Rf=0.19 (2:1 CH₂Cl₂/acetone); ¹H NMR (CDCl₃, 400 MHz) δ 7.30 (m, 3H), 6.23 (t, J=7 Hz, 1H), 4.04 (m, 2H), 2.69 (m, 2H), 2.57 (m, 2H), 1.74 (m, 2H), 1.56 (m, 2H), 1.48 (m, 1H), 1.47 (s, 9H), 1.16 (m, 2H).

Preparation of Ethyl {3-[2-(N-BOC-piperidin-4-yl)ethyl]-2-pyridon-1-yl}acetate (107)

To a stirred solution of 106 (0.44 g, 1.4 mmol) in dry DMF (7.2 mL) at 0° C. was added NaN(TMS)₂ (2.1 mL, 2.1 mmol, 1M/hexanes) dropwise. After 30 min. ethyl bromoacetate (0.79 mL, 7.2 mmol) was added dropwise to the reaction mixture. After an additional hour the reaction was diluted with ethyl acetate and then washed with H₂O, 5% KHSO₄, sat. NaHCO₃ and brine, dried (MgSO₄) and concentrated. Flash chromatography (silica, 45% ethyl acetate/hexanes) gave 107 as a colorless oil. TLC Rf=0.33 (60% ethyl acetate/hexanes); 7.20 (dd, J=6 and 1 Hz, 1H), 7.11 (dd, J=7 and 2 Hz, 1H), 6.15 (t, J=7 Hz, 1H), 4.62 (s, 2H), 4.24 (q, J=7 Hz, 2H), 4.04 (m, 2H), 2.69 (m, 2H), 2.55 (m, 2H), 1.72 (m, 2H), 1.52 (m, 2H), 1.78 (m, 1H), 1.48 (s, 9H), 1.13 (m, 2H).

Preparation of {3-[2-(N-BOC-piperidin-4-yl)ethyl]-2-pyridon-1-yl} acetic acid (108)

Utilizing the procedure for converting 55 to 56, 107 (0.51 g, 1.3 mmol) gave 108 as a colorless foam. TLC RF=0.58 (9:1:1 CH₂Cl₂/CH₃OH/HOAc).

Preparation of {3-[2-(N-BOC-piperidin-4-yl)ethyl]-2-pyridon-1-yl}acetyl-3(R)-methyl -β-alanine ethyl ester (109)

Utilizing the procedue for converting 15 to 16, 108 (0.15 g, 0.41 mmol) gave 109 as a waxy solid after flash chromatography (silica, ethyl acetate). TLC Rf=0.38 (ethyl acetate) ¹H NMR (CDCl₃, 400 MHz) δ 7.24 (dd, J=7 and 2 Hz, 1H), 7.21 (dd, J=7 and 2 Hz, 1H), 7.07 (bd, J=8 Hz, 1H), 6.19 (t, J=7 Hz, 1H), 4.51 (s, 2H), 4.30 (m, 1H), 4.08 (q, J=7 Hz, 2H), 4.08 (m, 2H), 2.69 (m, 2H), 2.55 (m, 2H), 1.72 (m, 2H), 1.51 (m, 2H), 1.45 (s, 9H), 1.43 (m, 1H), 1.23 (t, J=7 Hz, 3H), 1.22 (d, J=7 Hz, 3H), 1.13 (m, 2H).

Preparation of {3-[2-(N-BOC-piperidin-4-yl)ethyl]-2-pyridon-1-yl}acetyl-3(R)-methyl -β-alanine (110)

Utilizing the procedure for converting 55 to 56, 109 (0.19 g, 0.41 mmol) gave 110 as a colorless oil. TLC=0.59 (9.5/0.5/0.5 $CH_2Cl_2/CH_3/OH/HOAc$).

Preparation of {3-[2-(Piperidin-4-yl)ethyl]-2-pyridon-1-yl}acetyl-3(R)-methyl -β-alanine (111)

A solution of 103 (0,18 g, 0.40 mmol), $CH_2Cl_2$ (2.0 mL), anisole (86 ξL, 0.80 mmol), and trifluoroacetic acid (2.0 mL) was stirred at −15° for 15 min. The yellow reaction mixture was concentrated and the residual trifluoroacetic acid removed azeotropically with toluene. Flash chromatography (silica, 10/1.3/1.3 ethanol/$NH_4OH/H_2O$) give 111 as a white amorphous solid. TLC Rf=0.17 (10:1:1 ethanol/$NH_4OH/H_2O$); $^1H$ NMR ($D_2O$, 400 MHz) δ 7.57 (dd, J=7 and 1 Hz, 1H), 7.49 (dd, J=7 and 1Hz, 1H), 6.51 (t, J=7 Hz, 1H), 4.66 (m, 2H), 4.20 (m, 1H), 3.42 (m, 2H), 2.97 (m, 2H), 2.59 (m, 2H), 2.46 (dd, j=14 and 6 Hz, 1H), 2.32 (dd, J=14 and 7 Hz, 1H), 2.00 (m, 2H), 1.60 (m, 3H), 1.42 (m, 2H).

Preparation of N-Cbz-4-piperidineethanol (112)

To a stirred solution of 4-piperidineethanol 8 (15 g, 0.12 mol), THF (500 mL), and diisopropylethylamine (40.5 mL, 0.23 mol) at 0° C. was added benzyl chloroformate (16.5 mL, 0.12 mmol). After 1 h at 0° C. the reaction mixture was diluted with ethyl acetate and then washed with $H_2O$ (2×), 10% $KHSO_4$, and brine, dried ($MgSO_4$), and concentrated to give 112 as a colorless oil. TLC Rf=0.60 (ethyl acetate); $^1H$ NMR (300 MHz, $CDCl_3$) δ 7.35 (m, 5H), 5.13 (s, 2H), 4.18 (m, 2H), 3.70 (q, J=7 Hz, 2H), 2.80 (m, 2H), 1.80–1.50 (m, 5H), 1.19 (m, 2H).

Preparation of N-Cbz-4-piperidine ethyl iodide (113)

Utilizing the procedure for converting 9 to 10, 112 (30.6 g, 0.12 mol) gave 113 as a colorless oil after flash chromatography (silica, 10% ethyl acetate/hexanes).

Preparation of 1-[2-(N-Cbz-piperidin-4-yl)ethyl]-(2-pyrrolidinone) (114)

To a stirred solution of 2-pyrolidinone (11.0 g, 0.13 mol) in dry DMF (500 mL) at ambient temperature was added $NaN(TMS)_2$ (129 mL, 129 mmol, 1M/THF) dropwise. After 10 min, the iodide 113 (24.1 g, 64.6 mmol) in DMF (50 mL) was added to the reaction vessel. After 1 hour, the reaction mixture was diluted with ethyl acetate and then washed with $H_2O$, sat. $NaHCO_3$ and brine, dried ($MgSO_4$) and concentrated. Flash chromatography (silica, ethyl acetate) gave 114 as a colorless oil.

TLC Rf=0.16 (ethyl acetate); $^1H$ NMR (300 MHz, $CDCl_3$) δ 7.40–7.20 (m, 5H), 5.12 (s, 2H), 4.19 (m, 2H), 3.34 (m, 2H), 2.77 (m, 2H), 2.40 (m, 2H), 2.04 (m, 2H), 1.74 (m, 2H), 1.47 (m, 3H), 1.15 (m, 2H).

Preparation of 1-[2-(N-Cbz-piperidin-4-yl)ethyl]-3-propen-2-yl-(2-pyrrolidinone) (115)

To a stirred solution of 114 (8.0 g, 24.2 mmol), and THF (180 mL) at −78° C. was added LDA (50 mL, 25 mmol, 0.5M/THF) dropwise. After 15 min. allyl bromide (2.3 mL, 26.6 mmol) was added. After 1.0 hour, the reaction mixture was allowed to warm to 0° C. over a 10 min. period. The reaction mixture was diluted with ethyl acetate and then washed with 5% $KHSO_4$ and brine, dried ($MgSO_4$) and concentrated. Flash chromatography (silica, 50% ethyl acetate/hexanes) gave 115.

TLC Rf=0.65 (ethyl acetate); $^1H$ NMR (300 MHz, $CDCl_3$) δ 7.35 (m, 5H), 5.80 (m, 1H), 5.12 (m, 2H), 4.18 (m, 2H), 3.33 (m, 4H), 2.80 (m, 2H), 2.56 (m, 2H), 2.20 (m, 2H), 1.78 (m, 2H), 1.48 (m, 3H), 1.20 (m, 2H).

Preparation of 1-[2-(N-Cbz-piperidin-4-yl)-ethyl]-3-acetic acid-2-pyrrolidinone (116)

Utilizing the procedure for converting 14 to 15, 115 (4.7 g, 12.7 mmol) gave 116 as a light brown oil after flash chromatography (silica, $CH_2Cl_2/CH_3OH/HOAc$ 9.5:0.5:0.5).

TLC Rf=0.63 ($CH_2Cl_2/CH_3OH/HOAc$ 9.0:0.5:0.5); $^1H$ NMR (300 MHz, $CDCl_3$) δ 7.37 (m, 5H), 5.15 (s, 2H), 4.18 (m, 2H), 3.37 (m, 4H), 3.00–2.30 (m, 5H), 1.77 (m, 2H), 1.46 (m, 3H), 1.18 (m, 2H).

Preparation of [1-[2-(N-Cbz-piperidin-4-yl)ethyl]-2-pyrrolidinone-3]acetyl-2 -aminoethylphosphonic acid (117)

A solution of 116 (388 mg, 1.0 mmol), $Et_3N$ (0.14 mL, 1.0 mmol), and dry dioxane (5 mL) at 0° C. was treated with isobutyl chloroformate (0.13 mL, 1.0 mmol). The reaction mixture was warmed until the dioxane melted. A solution of 2-aminoethylphosphonic acid (125 mg, 1.0 mmol), $Na_2CO_3$ (106 mg) and $H_2O$ (2 mL) was added to the reaction vessel at ambient temperature. After 4 hours the dioxane was evaporated and the residue acidified with 1N HCl. The mixture was washed with ethyl acetate (3×). The aqueous portion was concentrated to dryness to afford crude 117.

TLC Rf=0.15 (9:1.0:1.0 $CH_2Cl_2/CH_3OH/HOAc$).

Preparation of [1-[2-(piperidin-4-yl)ethyl]-2-pyrrolidinone-3]acetyl-2-aminoethylphosphonic acid (118)

The crude phosphonic acid 117 (464 mg) was dissolved in 10% $HOAc/CH_3OH$ (20 mL), then $Pd(OH)_2$ (50 mg) was added and the mixture hydrogenated on the Parr apparatus (50 PSI) overnight. After 20 hours the reaction mixture was filtered through a celite pad and the filtrate concentrated. Flash chromatography (silica, 8:1:1 $CH_3OH/H_2O/NH_4OH$) gave 118 as an amorphous solid.

TLC Rf=0.14 (8:1:1 $CH_3OH/H_2O/NH_4OH$); $^1H$ NMR (300 MHz, $H_2O$) δ 3.40 (m, 8H), 3.18 (m, 1H), 2.92 (m, 3H), 2.60 (m, 1H), 2.38 (m, 1H), 2.26 (m, 1H), 1.97 (m, 2H), 1.79 (m, 3H), 1.56 (m, 2H), 1.40 (m, 2H).

Preparation of (4-N-Cbz-amino)cyclohexane carboxylic acid methyl ester (121)

To a suspension of 120 (17.5 g, 0.12 mol) in $CH_3OH$ (150 mL) at −10° C. was added thionyl chloride (13.4 mL, 0.18 mol) portionwise over a 5 min. period, followed by removal of the cooling bath. After 16 hours the resulting solution was concentrated and the residue dissolved in DMF (150 mL), cooled to 0° C. then treated sequentially with N(i-Pr)$_2$Et (52 mL, 0.3 mol) and benzyl chloroformate (18.6 mL, 0.13 mol). The cooling bath was removed and after 24 hours the reaction mixture was concentrated. The residue was diluted with ethyl acetate and then washed with saturated NaHCO$_3$, 5% KHSO$_4$ and brine, dried (MgSO$_4$) and concentrated. Flash chromotography (silica, 20% ethyl acetate/hexanes) gave 121 as a waxy crystalline solid.

TLC Rf=0.34, 0.39 (30% ethyl acetate/hexanes); $^1$H NMR (400 MHz, CDCl$_3$) δ 7.38 (m, 5H), 5.09 (bs, 2H), 4.68 (m, 0.5H), 4.59 (m, 0.5H), 3.72 (m, 0.5H), 3.68 (s, 1.5H), 3.67 (s, 1.5H), 3.50 (m, 0.5H) 2.45 (m, 1H), 2.13–1.50 (m, 8H).

Preparation of (4-N-Cbz-amino)[1-(propen-3-yl)]cyclohexane carboxylic acid methyl ester (122)

To a stirred solution of 121 (1.0 g, 3.4 mmol) in dry THF (17.2 mL) at −78° C. was added LDA (4.3 mL, 8.6 mmol, 2.0M) dropwise. The cooling bath was warmed to −40° C. After stirring at −40° C. for 15 min. the reaction mixture was recooled to −78° C. and then treated sequentially with 1,3-dimethyl-3,4,5,6-tetrahydro-2-(1H-pyrimidinone) (2.0 mL, 17 mmol) and allyl bromide (0.44 mL, 5.1 mmol). After 2 hours the reaction was diluted with ethyl acetate and then washed with H$_2$O), sat. NH$_4$Cl, sat. NaHCO$_3$ and brine. Drying (MgSO$_4$) and concentration gave a yellow oil which was subjected to flash chromatography (silica, 20% ethyl acetate/hexanes) to give 122 as a waxy crystalline solid.

TLC Rf=0.31 (20% ethyl acetate/hexanes); $^1$H NMR (400 MHz, CDCl$_3$) δ 7.34 (m, 5H), 5.67 (m, 1H), 5.10 (s, 2H), 5.05 (m, 2H), 4.54 (m, 1H), 3.67 (s, 3H), 3.48 (m, 1H), 2.21 (m, 2H), 2.00–1.00 (m, 8H).

Preparation of 4-Amino,1-(propen-3-yl)cyclohexane carboxylic acid methyl ester (123)

Trifluoroacetic acid (19 mL) was added to a mixture of 122 (0.63 g, 1.9 mmol) and anisole (0.41 ml, 3.8 mmol) at 0° C. After 5 min. the reaction mixture became homogeneous and removal of the cooling bath was followed by stirring overnight. Concentration, followed by flash chromatography (silica, 17:1:1 ethanol/NH$_4$OH/H$_2$O) gave 123 as a yellow oil.

TLC Rf=0.53 (30% ethyl acetate/hexanes).

Preparation of [2-Aza-3-oxo-[2.2.2]bicyclooct-4-yl]prop-3-ene (124)

A solution of 123 (0.39 g, 1.97 mmol) in toluene (10 mL) was heated at 170° C. in a sealed tube overnight. The cooled dark reaction mixture was purified by flash chromatography (silica, 85% ethyl acetate/hexanes) to give 124 as a tan oil.

TLC Rf=0.30 (85% ethyl acetate/hexanes); $^1$HMNR (400 MHz, CDCl$_3$) δ 6.08 (m, 1H), 5.88 (m, 1H), 5.04 (m, 2H), 3.61 (m, 1H), 2.35 (d, J=7 Hz, 2H), 1.80–1.50 (m, 8H).

Preparation of ([2-(N-Boc-piperidin-4-yl)ethyl]-2-aza-3-oxo-[2.2.2]bicyclooct-4-yl) prop-3-ene (125)

Utilizing the procedure for converting 36a to 37a, 124 (0.18 g, 1.1 mmol) gave 125 (0.45 g, 100%) after flash chromatography (silica, 40% ethyl acetate/hexanes).

TLC Rf=0.36 (40% ethyl acetate/hexanes); $^1$H NMR (400 MHz, CDCl$_3$) δ 5.87 (m, 1H), 5.05 (m, 2H), 4.08 (m, 2H), 3.51 (m, 1H), 3.40 (t, J=8 Hz, 2H), 2.67 (m, 2H), 2.34 (d, J=7 Hz, 2H), 1.75–1.35 (m, 13H), 1.47 (s, 9H), 1.12 (m, 2H).

Preparation of 3-(1-[2-(N-Boc-piperidin-4-yl)ethyl]-2-aza-3-oxo-[2.2.2]bicyclooct-4-yl)acetyl-β-alanine (128)

Utilizing the procedure for converting 14 to 5, 125 (0.42 g, 1.1 mmol) gave 126 (0.34 g, 76%) as a white sticky foam.

TLC Rf=0.58 (9.5:0.5:0.5 CH$_2$Cl$_2$/CH$_3$OH/AcOH).

Preparation of ([2-(N-Boc-piperidin-4-yl)ethyl]-2-aza-3-oxo-[2.2.2]bicyclooct-4-yl) acetyl-β-alanine tert-butyl ester (127).

Utilizing the procedure for converting 15 to 16, 126 (0.14 g, 0.35 mmol) gave 127 (0.10 g, 55%) as a colorless oil after flash chromatography (silica, 6:1 CH$_2$Cl$_2$/acetone).

TLC Rf=0.52 (2:1 CH$_2$Cl$_2$/acetone); $^1$H NMR (400 MHz, CDCl$_3$) δ 7.90 (m, 1H), 4.04 (m, 2H), 3.56 (m, 1H), 3.42 (m, 4H), 2.67 (m, 2H), 2.42 (t, J=7 Hz, 2H), 1.76–1.34 (m, 13H), 1.46 (s, 18H), 1.12 (m, 2H).

Preparation of ([2-(Piperidin-4-yl)ethyl]-2-aza-3-oxo-[2.2.2]bicyclooct-4-yl) acetyl-β-alanine (128)

Utilizing the procedure for converting 40a to 41a, 127 (0.10 g, 0.19 mmol) gave 128 (29 mg, 39%) as a fluffy solid after flash chromotography (silica, 10:1.2:1.2 ethanol/H$_2$O/NH$_4$OH).

TLC Rf=0.17 (10:1:1 ethanol/NH$_4$OH/H$_2$O); $^1$H NMR (400 MHz, D$_2$O) δ 3.78 (m, 1H), 3.50–3.35 (m, 6H), 2.97 (m, 2H), 2.48 (s, 2H), 2.38 (t, J=7 Hz, 2H), 2.02 (m, 2H), 1.78 (m, 6H), 1.58 (m, 5H), 1.42 (m, 2H).

SCHEME 16

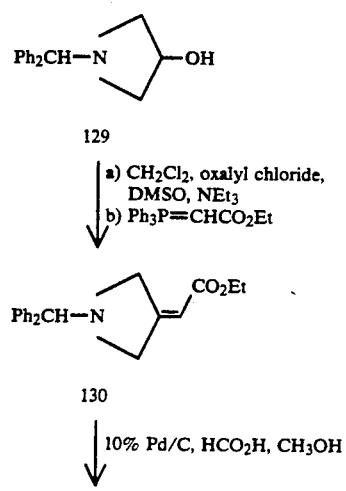

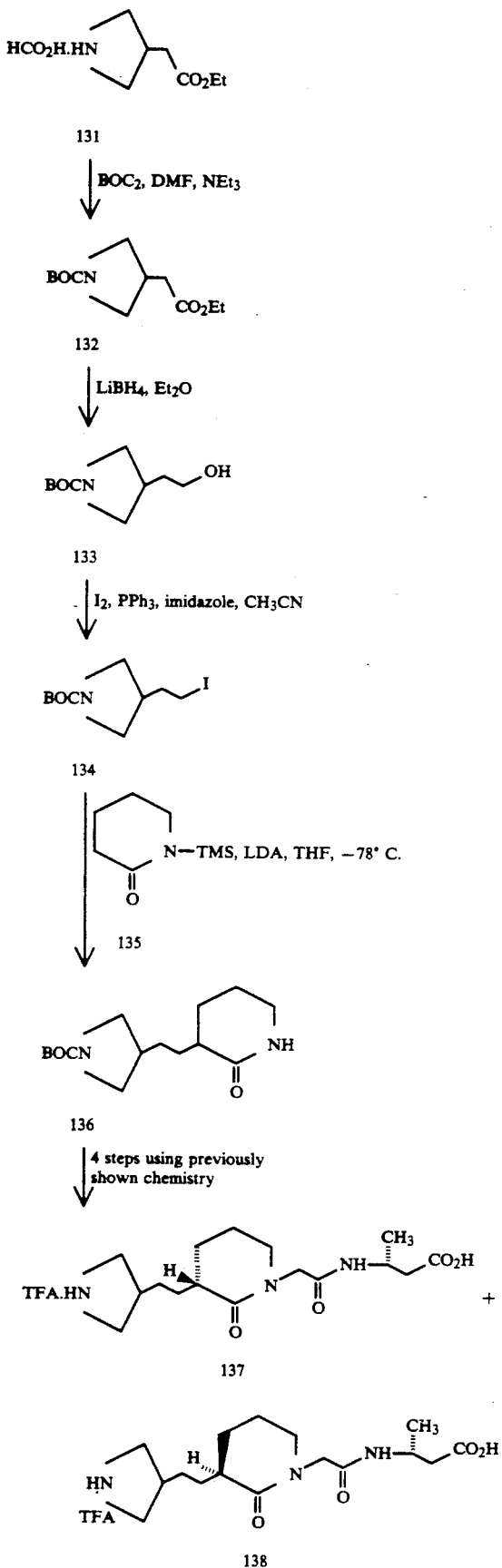

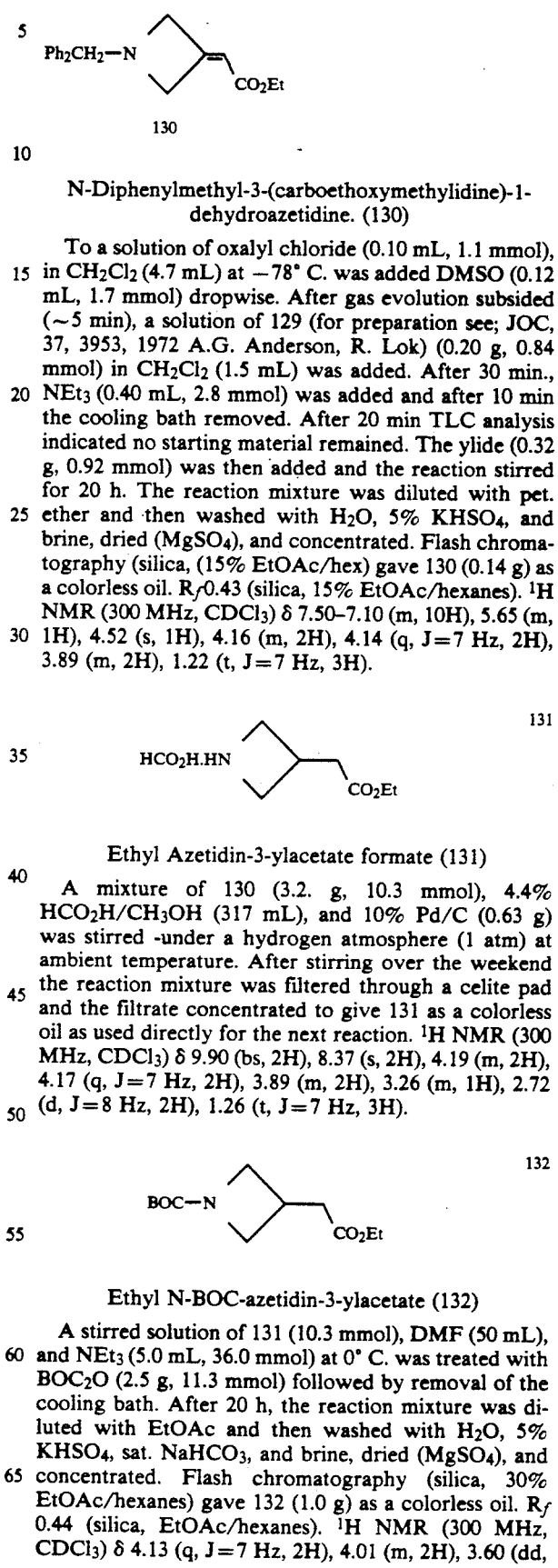

N-Diphenylmethyl-3-(carboethoxymethylidine)-1-dehydroazetidine. (130)

To a solution of oxalyl chloride (0.10 mL, 1.1 mmol), in $CH_2Cl_2$ (4.7 mL) at $-78°$ C. was added DMSO (0.12 mL, 1.7 mmol) dropwise. After gas evolution subsided (~5 min), a solution of 129 (for preparation see; JOC, 37, 3953, 1972 A.G. Anderson, R. Lok) (0.20 g, 0.84 mmol) in $CH_2Cl_2$ (1.5 mL) was added. After 30 min., $NEt_3$ (0.40 mL, 2.8 mmol) was added and after 10 min the cooling bath removed. After 20 min TLC analysis indicated no starting material remained. The ylide (0.32 g, 0.92 mmol) was then added and the reaction stirred for 20 h. The reaction mixture was diluted with pet. ether and then washed with $H_2O$, 5% $KHSO_4$, and brine, dried ($MgSO_4$), and concentrated. Flash chromatography (silica, (15% EtOAc/hex) gave 130 (0.14 g) as a colorless oil. $R_f$ 0.43 (silica, 15% EtOAc/hexanes). $^1H$ NMR (300 MHz, $CDCl_3$) δ 7.50–7.10 (m, 10H), 5.65 (m, 1H), 4.52 (s, 1H), 4.16 (m, 2H), 4.14 (q, J=7 Hz, 2H), 3.89 (m, 2H), 1.22 (t, J=7 Hz, 3H).

Ethyl Azetidin-3-ylacetate formate (131)

A mixture of 130 (3.2. g, 10.3 mmol), 4.4% $HCO_2H/CH_3OH$ (317 mL), and 10% Pd/C (0.63 g) was stirred under a hydrogen atmosphere (1 atm) at ambient temperature. After stirring over the weekend the reaction mixture was filtered through a celite pad and the filtrate concentrated to give 131 as a colorless oil as used directly for the next reaction. $^1H$ NMR (300 MHz, $CDCl_3$) δ 9.90 (bs, 2H), 8.37 (s, 2H), 4.19 (m, 2H), 4.17 (q, J=7 Hz, 2H), 3.89 (m, 2H), 3.26 (m, 1H), 2.72 (d, J=8 Hz, 2H), 1.26 (t, J=7 Hz, 3H).

Ethyl N-BOC-azetidin-3-ylacetate (132)

A stirred solution of 131 (10.3 mmol), DMF (50 mL), and $NEt_3$ (5.0 mL, 36.0 mmol) at 0° C. was treated with $BOC_2O$ (2.5 g, 11.3 mmol) followed by removal of the cooling bath. After 20 h, the reaction mixture was diluted with EtOAc and then washed with $H_2O$, 5% $KHSO_4$, sat. $NaHCO_3$, and brine, dried ($MgSO_4$), and concentrated. Flash chromatography (silica, 30% EtOAc/hexanes) gave 132 (1.0 g) as a colorless oil. $R_f$ 0.44 (silica, EtOAc/hexanes). $^1H$ NMR (300 MHz, $CDCl_3$) δ 4.13 (q, J=7 Hz, 2H), 4.01 (m, 2H), 3.60 (dd, J=9 and 6 Hz, 1H), 2.88 (m, 1H), 2.61 (d, J=8 Hz, 2H), 1.44 (s, 9H) 1.25 (t, J=7H, 3H).

133

N-BOC-Azetidin-3-ylethanol (133)

A stirred solution of 132 (0.96 g, 3.9 mmol) in ether (20 mL) at ambient temperature was treated with LiBH$_4$ (0.34 g, 15.8 mmol) then heated to 55° C. After 45 min at 55° C., the cooled reaction was quenched with 5% KHSO$_4$ (10 mL) and then diluted with EtOAc. The organic phase was washed with 5% KHSO$_4$ and brine, dried (MgSO$_4$), and concentrated to give 133 (0.79 g) as a colorless oil. R$_f$ 0.46 (silica, EtOAc). $^1$H NMR (300 MHz, CDCl$_3$) δ 4.04 (m, 2H), 3.70–3.50 (m, 4H), 2.63 (m, 1H), 1.83 (m, 2H), 1.44 (s, 9H).

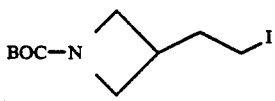
134

N-BOC-Azetidin-3-ylethyl iodide (134)

A stirred solution of 133 (0.78 g, 3.8 mmol), PPh$_3$ (1.1 g, 4.3 mmol), imidazole (0.40 g, 5.8 mmol), and CH$_3$CN (20 mL) at 0° C. was treated with iodine (1.0 g, 4.3 mmol). After 15 min the cooling bath was removed and stirring continued for 5 h. The reaction mixture was then diluted with H$_2$O and extracted with hexanes (5×25 mL then 4×50 mL). The combined extracts were dried (MgSO$_4$) and concentrated. Flash chromatography (silica, 20% EtOAc/hexanes) gave 134 (0.99 g) as a colorless oil. R$_f$ 0.44 (silica, 20% EtOAc/hexanes). $^1$H NMR (400 MHz, CDCl$_3$) δ 4.04 (t, J=7 Hz, 2H), 3.57 (dd, 2H), 3.10 (t, 2H), 2.64 (m, 1H), 2.16 (q, 2H), 1.43 (s, 9H).

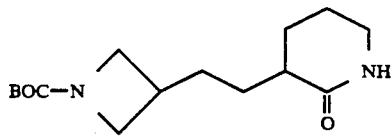
136

3-[N-BOC-2-(Azetidin-3-yl)ethyl]-2-piperidone (136)

A solution of 135 (for preparation see; D. H. Hua, et. al., JOC, 55, 3682, 1990) (0.19 g, 1.2 mmol) in THF (3.9 mL) at −78° C. was added LDA (0.58 mL, 1.2 mmol, 2.0M/heptane/THF/ethylbenzene) dropwise. After 15 min 134 (0.30 g, 0.96 mmol) in THF (3.5 mL) was added dropwise. After stirring 1.0 h, the reaction was quenched with CH$_3$OH (7.5 mL) and the resulting solution warmed to ambient temperature. The solution was then diluted with EtOAc and then washed with H$_2$O, 5% KHSO$_4$, sat. NaHCO$_3$, and brine, dried (MgSO$_4$), and concentrated to give 136 (0.27 g) as a white solid. R$_f$ 0.25 (silica, 2:1 CH$_2$Cl$_2$/acetone). $^1$H ITMR (400 MHz, CDCl$_3$) δ 5.81 (bs, 1H), 3.95 (m, 2H), 3.54 (m, 2H), 3.10 (m, 2H), 2.47 (m, 1H), 2.26 (m, 1H), 2.00–1.40 (m, 8H), 1.43 (s, 9H).

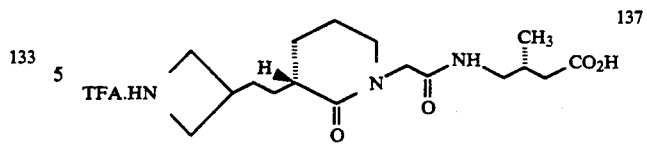
137

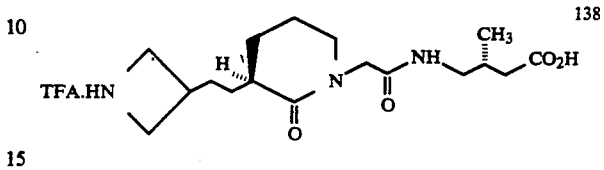
138

[3(R)-(2-Azetidin-3-yl)ethyl]-2-piperidone-1]acetyl-3(R)-methyl-β-alanine (137) and [3(S)-(2-Azetidin-3-yl)ethyl]-2-piperidone-1]acetyl-3(R)-methyl-β-alanine (138).

Diastereomers were separated by Prep HPLC: column, delta pak C-18, 100 Å, 15 μ; 0→50% over 60 min. A to B A=0.1% TFA/H$_2$O, B=CH$_3$CN; F=50 mL/min, A=215.

Faster moving diastereomer; $^1$H NMR (00 MHz, D$_2$) δ 4.22 (q, J=7 Hz, 1H), 4.14 (t, J=8 Hz, 2H), 4.04 (d, J=16 Hz, 1H), 3.93 (d, J=16 Hz, 1H), 3.81 (m, 2H), 3.37 (m, 2H), 2.93 (m, 1H), 2.47 (dd, J=7 and 2 Hz, 2H), 2.42 (m, 1H), 2.00–1.45 (m, 8H), 1.18 (d, J=7 Hz, 3H).

Slower moving diastereomer; $^1$H NMR (400 MHz, D$_2$O) δ 4.21 (q, J=7 Hz, 1H), 4.14 (t, J=8 Hz, 2H), 4.03 (d, J=16 Hz, 1H), 3.94 (d, J=16 Hz, 1H), 3.81 (m, 2H), 3.38 (m, 2H), 2.92 (m, 1H), 2.43 (m, 3H), 2.00–1.45 (m, 8H), 1.18 (d, J=7 Hz, 3H).

SCHEME 17

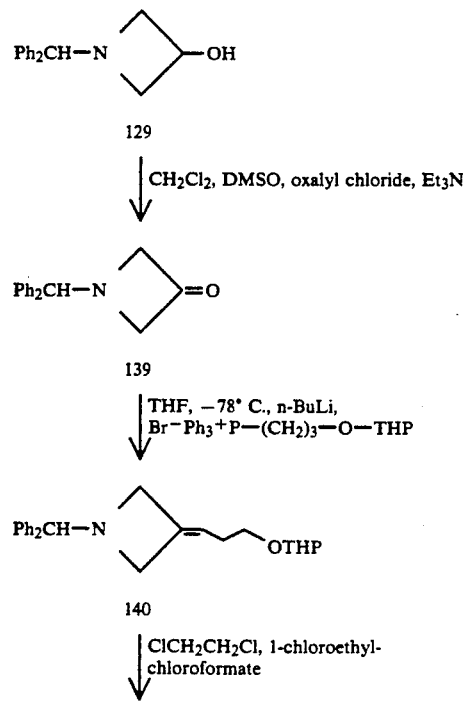

-continued
SCHEME 17

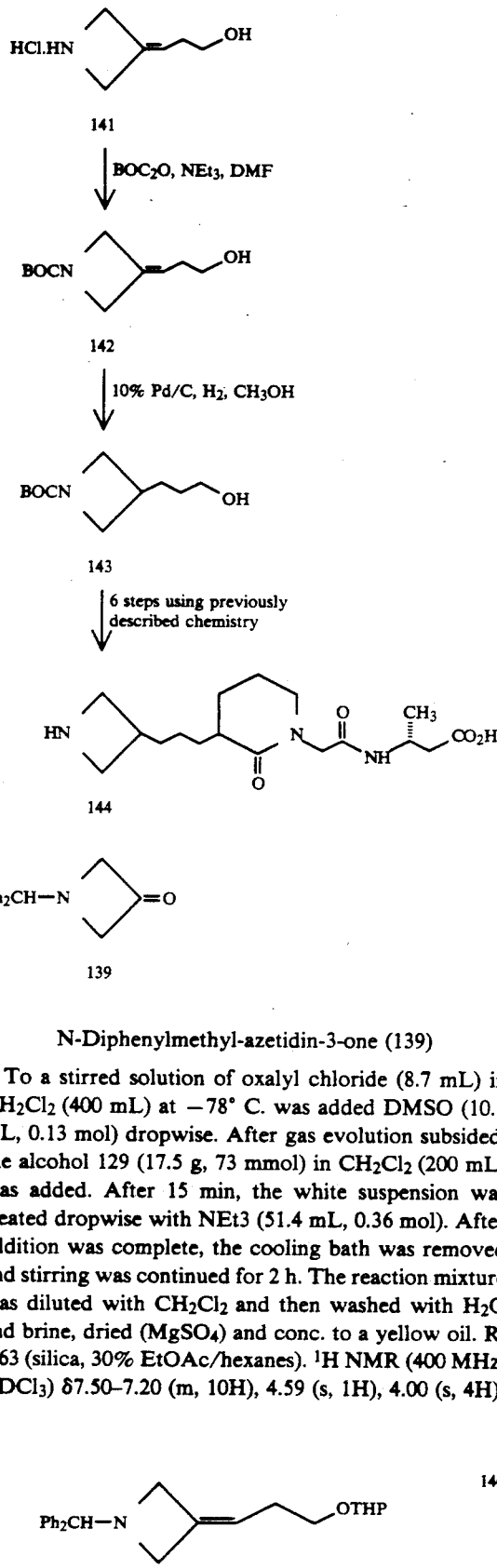

N-Diphenylmethyl-azetidin-3-one (139)

To a stirred solution of oxalyl chloride (8.7 mL) in CH₂Cl₂ (400 mL) at −78° C. was added DMSO (10.3 mL, 0.13 mol) dropwise. After gas evolution subsided, the alcohol 129 (17.5 g, 73 mmol) in CH₂Cl₂ (200 mL) was added. After 15 min, the white suspension was treated dropwise with NEt3 (51.4 mL, 0.36 mol). After addition was complete, the cooling bath was removed and stirring was continued for 2 h. The reaction mixture was diluted with CH₂Cl₂ and then washed with H₂O and brine, dried (MgSO₄) and conc. to a yellow oil. R$_f$ 0.63 (silica, 30% EtOAc/hexanes). ¹H NMR (400 MHz, CDCl₃) δ7.50–7.20 (m, 10H), 4.59 (s, 1H), 4.00 (s, 4H).

2-[(N-Diphenylmethyl-3-dehydroazetidin-3-yl)methylene]-ethylolcytetrahydropyran ether (140)

A mixture of the phosphonium salt (for preparation see; Schow, S. R., McMorris, T. C., JOC, 44, 3760, 1979) (32.5 g, 66 mmol) in THF (300 mL) at −78° C. was treated with n-BuLi (44.6 mL, 71 mmol, 1.6 M/hexanes) dropwise then stirred for 1.0 h. The ketone 139 (15.4 g, 65 mmol) was then added followed by removal of the cooling bath. After 20 h, the reaction mixture was diluted with EtOAc and then washed with H₂O and brine, dried (MgSO₄), and concentrated. Flash chromatography (silica, 10% EtOAc/hexanes) gave 140 (5.8 g) as an oil. R$_f$ 0.50 (silica, 20% EtOAc/hexanes). ¹H NMR (400 MHz, CDCl₃) δ7.50–7.20 (m, 10H), 5.24 (bs, 1H), 4.56 (m, 1H), 4.48 (bs, 1H), 3.90–3.65 (m, 6H), 3.48 (m, 1H), 3.37 (m, 1H), 2.15 (m, 2H), 1.85–1.45 (m, 6H).

2-[(3-Dehydroazetidin-3-yl)methylenelethanol (141)

To a stirred solution of 140 (2.4 g, 6.63 mmol) in CH₂Cl₂ (66 mL) at 0° C. was added 1-chloroethyl chloroformate (0.73 mL, 6.65 mmol) followed by refluxing for 4.0 h. The reaction mixture was then concentrated and the residue dissolved in CH₃OH (66 mL) and refluxed for 1 h. Concentration gave crude 141 as an orange oil. R$_f$ 0.18 (silica, 4:1:1 CH₂Cl₂/CH₃OH/AcOH).

2-[(N-BOC-3-Dehydroazetidin-3-yl)methylene]ethanol (142)

A solution of 141 (2.4 g, 6.63 mmol), DMF (66 mL), and NEt3 (1.1 mL, 8.0 mmol) at ambient temperature was treated with BOC₂O (1.7 g, 8.0 eq). After 1.0 h, the reaction mixture was diluted with EtOAc and then washed with 10% KHSO₄, H₂O and brine, dried (MgSO₄), and concentrated. Flash chromatography (silica, 60% EtOAc/hexanes) gave 142 (560 mg). R$_f$ 0.51 (silica, EtOAc). ¹H NMR (300 MHz, CDCl₃) δ5.33 (m, 1H), 4.47 (m, 4H), 3.65 (m, 2H), 2.19 (m, 2H), 1.44 (s, 9H).

3-(N-BOC-Azetidin-3-yl)propanol (143)

A mixture of 142 (560 mg, 2.62 mmol), CH₃OH (26 mL), and 10% Pd/C (112 mg) was stirred under a hydrogen atmosphere (1 atm) at ambient temperature. After 20 h, the reaction mixture was filtered through a celite pad and the filtrate concentrated to give 143 (529 mg) as a yellow oil. R$_f$ 0.38 (silica, EtOAc). ¹H NMR (400 MHz, CDCl₃) δ3.99 (t, 2H), 3.64 (t, 2H), 3.53 (dd, 2H), 2.50 (m, 1H), 1.70–1.50 (m, 2H), 1.45 (s, 9H). [3-(3-Azetidin-3-yl)propyl)-2-piperidone-1]acetyl-3(R)-methyl-B-alanine (144)

144: R_f 0.29 (silica, 10:1:1 CH₃OH/NH₄OH/H₂O). ¹H NMR (400 MHz, D₂O) δ4.03 (m, 3H), 3.89 (dd, 1H), 3.80 (dd, 1H), 3.68 (m, 2H), 3.24 (m, 2H), 2.82 (m, 1H), 2.27 (m, 2H), 2.18 (dd, 1H), 1.85–1.10 (m, 10H), 1.03 (d, 3H).

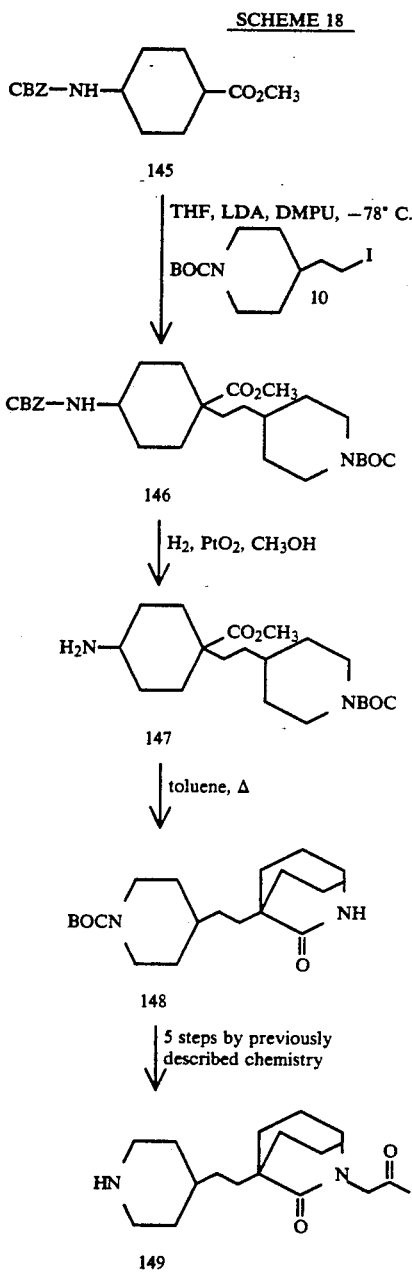

Preparation of [1-[2-(N-BOC-Piperidin-4-yl)ethyl]-1-methoxycarbonyl-4-Benzyloxycarbonylamino]cyclohexane (146)

To a solution of 145 (prepared from p-aminobenzoic acid; Org. Syn. Coll. Vol 5. 670; then standard deprotection, Protective Groups in Organic Synthesis, Greene, T. W., Wuts, P. G.) (1.0 g, 3.4 mmol) in THF (34 mL) at −78° C. was added LDA (5.1 mL, 10.3 mmol, 2.0 M) dropwise. The resulting yellow solution was stirred for 20 min, then treated sequentially with DMPU (1,3-dimethyl-3,4,5,6-tetrahydro-2(1H)-pyrimidone) (1.2 mL, 3.4 mmol) and 10 (1.2 g, 3.4 mmol) in THF (10 mL). After 3.0 h, the reaction was quenched with 5% KHSO₄ then extracted with EtOAc. The EtOAc extract was washed with 5% KHSO₄, sat. NaHCO₃, and brine, dried (MgSO₄), and concentrated. Flash chromatography (silica, 20% EtOAc/hexanes) gave 146 (0.3 g) as an oil. R_f 0.40 (silica, 30% EtOAc/hexanes). ¹H NMR (300 MHz, CDCl₃) δ7.33 (m, 5H), 5.07 (s, 2H), 4.08 (m, 2H), 3.67 (s, 3H), 3.45 (m, 1H), 2.63 (m, 2H), 2.22 (m, 2H), 1.92 (m, 2H), 1.65–1.00 (m, 13H), 1.47 (s, 9H).

[1-[2-(N-BOC-Piperidin-4-yl)ethyl]-1-methoxycarbonyl]-4-aminocyclohexane (147)

A mixture of 146 (0.49 g, 0.97 mmol), PtO₂ (24 mg), and CH₃OH (5 mL) was stirred under a hydrogen atmosphere at ambient temperature. After 2 days, the reaction mixture was filtered through a celite pad and the filtrate concentrated. The residue was dissolved in EtOAc and then washed with 1% aq. NAOH and brine, dried (MgSO₄), and concentrated to give 147 (0.32 g) as a yellow oil. R_f 0.7 (silica, 10:1:1 ethanol/H₂O/NH₄OH). ¹H NMR (300 MHz, CDCl₃) δ4.06 (m, 2H), 3.68 (s, 3H), 2.62 (m, 2H), 2.25–1.00 (m, 17H), 1.48 (s, 9H).

Preparation of [2-(N-BOC-Piperidin-4-yl)ethyl]−2-aza-3-oxo[2.2.2-]bicyclooct-4-yl (148)

A solution of 147 (0.32 g, 0.86 mmol) and toluene (7.5 mL) was heated at 180° C. in a sealed tube for 20 h. The cooled reaction mixture was concentrated then purified by flash chromatography (silica, EtOAc) to give 148 (0.13 g) as a yellow solid. R_f 0.22 (silica, EtOAc). ¹H NMR (400 MHz, CDCl₃) δ6.15 (m, 1H), 4.06 (m, 2H), 3.58 (m, 1H), 2.65 (m, 2H), 1.80–1.00 (m, 17H), 1.45 (s, 9H).

Preparation of 1-[(2-Piperidin-4-yl)ethyl-2-aza-3-oxo)[2.2.2]bicyclooct-4-yl)acetyl-3(R)-methyl-β-alanine (149)

149: R_f 0.22 (silica, 10:1:1 ethanol/H₂O/NH₄OH). ¹H NMR (400 MHz, D₂O) δ4.17 (m, 1H), 4.07 (s, 2H), 3.67 (m, 1H), 3.40 (m, 2H), 2.97 (m, 2H), 2.42 (dd, 1H), 2.33 (dd, 1H), 2.00–1.30 (m, 17H), 1.17 (d, 3H).

SCHEME 19

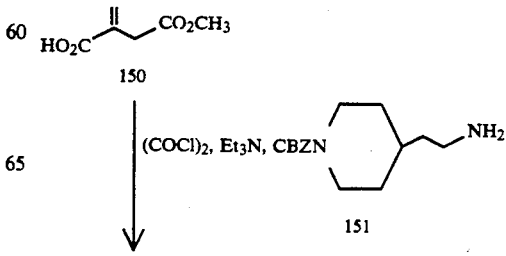

SCHEME 19 -continued

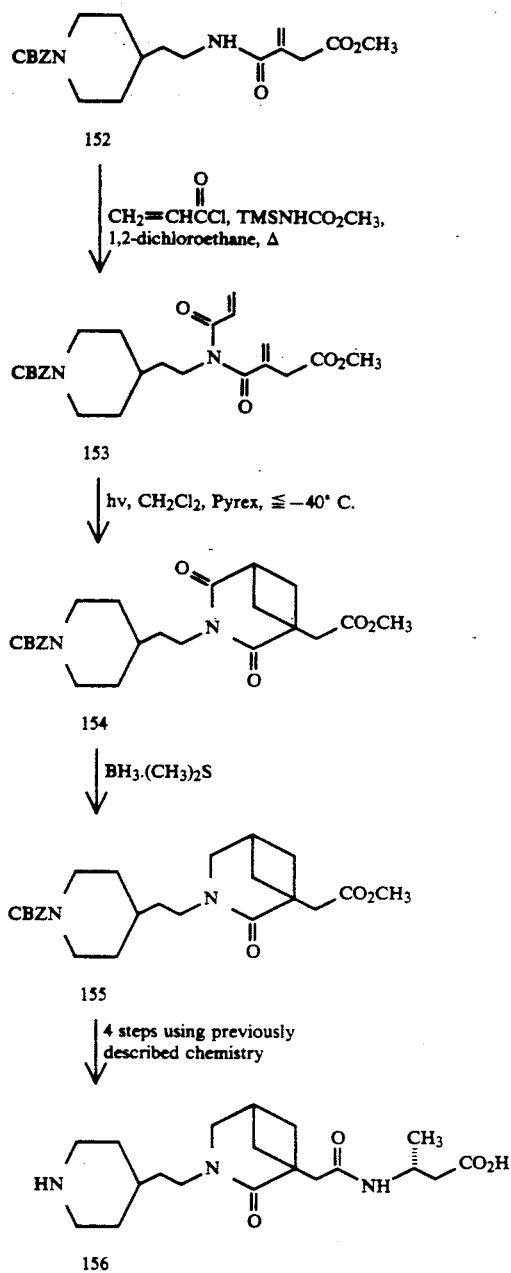

Preparation of [N-[2-(N'-CBZ-Piperidin-4-yl)ethyl]-2-carbomethoxymethyl]acrylamide (152)

A solution of 150 (available from TCI) (1.7 g, 11.9 mmol), DMF (75 μL), and CH$_2$Cl$_2$ (50 mL) at ambient temperature was treated with oxalyl chloride (1.0 mL, 11.9 mmol) followed by stirring for 1.0 h. This solution was added to a solution of 151 (2.8 g, 10.6 mmol) in CH$_2$Cl$_2$ (50 mL) at 0° C. After 2.0 h, the reaction mixture was diluted with EtOAc and then washed with H$_2$O, 5% KHSO$_4$, and brine, dried (MgSO$_4$), and concentrated. Flash chromatography (silica, 75% EtOAc/hexanes) gave 152 (2.1 g) as an oil. R$_f$ 0.34 (silica, 75% EtOAc/hexanes). $^1$H NMR (400 MHz, CDCl$_3$) δ7.32 (m, 5H), 6.15 (m, 1H), 5.75 (s, 1H), 5.45 (s, 1H), 5.12 (s, 2H), 4.16 (m, 2H), 3.69 (s, 3H), 3.37 (s, 2H), 3.36 (m, 2H), 2.76 (m, 2H), 1.71 (m, 2H), 1.50 (m, 3H), 1.14 (m, 2H).

Preparation of [[N-(N'-CBZ-Piperidin-4-yl)ethyl-N''-acryl]-2-carbomethoxymethyl]acrylamide (153)

A mixture of 152 (2.0 g, 5.3 mmol), acryloyl chloride (0.64 mL, 7.9 mmol), 1,2-dichloroethane (10 mL), and N-(trimethylsilyl)acetamide (1.7 g, 11.6 mmol) was refluxed for 24 h. The cooled reaction mixture was diluted with CH$_2$Cl$_2$ and then washed with sat. NaHCO$_3$, 5% KHSO$_4$, and brine, dried (MgSO$_4$), and concentrated. Flash chromatography (silica, 30% EtOAc/hexanes) gave 153 (2.1 g) as an oil. R$_f$ 0.28 (silica, 40% EtOAc/hexanes). $^1$H NMR (400 MHz, CDCl$_3$) δ7.35 (m, 5H), 6.72 (dd, 1H), 6.32 (dd, 1H), 5.70 (s, 1H), 5.67 (m, 1H), 5.63 (s, 1H), 5.12 (s, 2H), 4.14 (m, 2H), 3.84 (m, 2H), 3.72 (s, 3H), 3.50 (s, 2H), 2.75 (m, 2H), 1.72 (m, 2H), 1.56 (m, 2H), 1.47 (m, 1H), 1.16 (m, 2H).

Preparation of [3-(2-(N-CBZ-Piperidin-4-yl)ethyl)-3-aza-2,4-oxo[3.1.1-]bicyclooct-1-yl]acetic acid methyl ester (154)

Imide −153 (1.0 g, 2.26 mmol) was dissolved in 50 mL benzene, along with 50 mg, 2,6-di-tert-butyl-4-methyl-phenol (BHT). The degassed solution was heated to 180° C. in a heavy-walled pressure tube for 22 hours. After removing the solvent, the residue was purified by silica gel chromatography (50% EtOAc/hexane), providing 154 as an (oil). R$_f$ 0.27 (silica, 50% EtOAc/hexanes). $^1$H NMR (400 MHz, CDCl$_3$) δ7.32 (m, 5H), 5.12 (s, 2H), 4.14 (m, 2H), 3.72 (m, 2H), 3.68 (s, 3H), 3.17 (m, 1H), 2.75 (m, 2H), 2.69 (s, 2H), 1.73 (m, 2H), 1.48 (m, 2H), 1.43 (m, 1H), 1.15 (m, 2H).

Preparation of [3-(2-(N-CBZ-Piperidin-4-yl)ethyl)-3-aza-2-oxo[3.1.1-1bicyclooct-1-yl]acetic acid methyl ester (155)

To a solution of 154 (61 mg, 0.14 mmol) in THF (1 mL) at 0° C. was added BH$_3$.SMe2 (69 μL, 0.69 mmol, 10 M solution). After 1.0 h, the cooling bath was removed and stirring continued for 16 h. The reaction was carefully quenched with CH$_3$OH and concentrated (repeated 2X). Flash chromatography (silica, 60% EtOAc/hexanes) gave 155 (23 mg) as an oil. R$_f$ 0.37 (silica, 75% EtOAc/hexanes). $^1$H NMR (400 MHz, CDCl$_3$) δ7.35 (m, 5H), 5.12 (s, 2H), 4.15 (m, 2H), 3.66 (s, 2H), 3.40 (m, 2H), 3.36 (m, 2H), 2.76 (m, 3H), 2.59 (s, 2H), 2.18 (m, 2H), 1.90 (m, 2H), 1.72 (m, 2H), 1.50 (m, 2H), 1.43 (m, 1H), 1.15 (m, 2H).

Preparation of [3-(2-Piperidin-4-yl)ethyl)-3-aza-2-oxo[3.1.1]bicyclooct-1-yl]acetyl-3(R)-methyl-β-alanine (156)

156: R$_f$ 0.19 (silica, 10:1:1 ethanol/NH$_4$OH/H$_2$O). $^1$H NMR (400 MHz, D$_2$O) δ4.14 (m, 1H), 3.49 (m, 2H), 3.42 (m, 4H), 2.98 (m, 2H), 2.77 (m, 1H), 2.47 (d, 2H), 2.42 (dd, 1H), 2.29 (dd, 1H), 2.24 (m, 2H), 2.02 (m, 2H), 1.78 (m, 2H), 1.61 (m, 3H), 1.43 (m, 2H), 1.17 (d, 3H).

Applicants hereby incorporate by reference procedures for preparing compounds of the present invention whereby guanidines are prepared from amines and whereby amidines are prepared from corresponding itriles. Guanidines may be prepared from amines by those having ordinary skill in the art upon reaction with 3,5-dimethylpyrazole-1-carboxamidine nitrate (*Methods mol.*, 25b, 558, 1972). Amidines may be prepared from the corresponding nitrile by those having ordinary skill in the art using procedures demonstrated by Boere, R. T., et. al. *J. Organomet. Chem.*, 331(2), 161-7, 1987; and Fuks, R., *Tetrahedron*, 29 (14), 2147-51, 1973. Diketopiperazines may be prepared from amino acids by those having ordinary skill in the art using procedure demonstrated by Suzuki, K., et. al. *Pept. Chem.*, 18th, 11-14, 1980 or references included therein.

Utilizing the methodology demonstrated in this invention, the following compounds, included in Table I below, are exemplary of the compounds which may be prepared according to this invention. The compounds shown in Table II were prepared by methodology demonstrated in this invention.

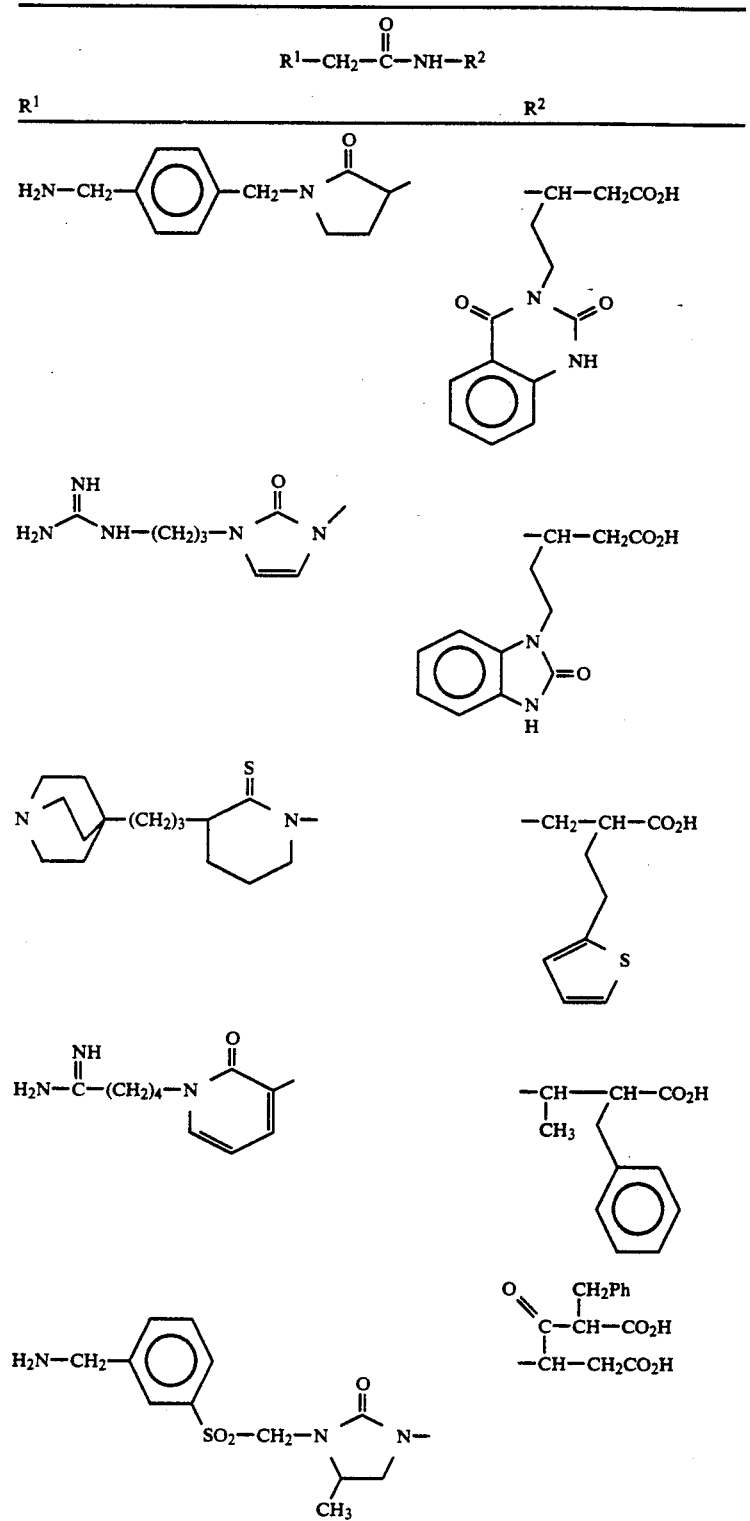

TABLE I-continued
$$R^1-CH_2-\overset{\overset{\displaystyle O}{\|}}{C}-NH-R^2$$
| R¹ | R² |
|---|---|
| 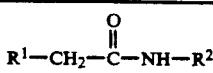 | 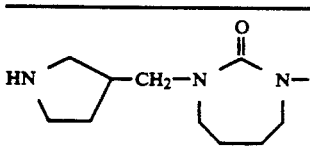 |
| 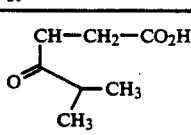 | $-CH_2-CH_2-CO_2H$ |
| 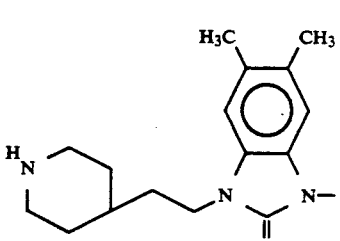 | 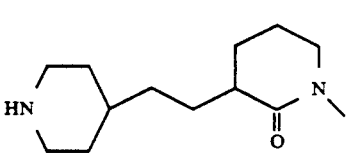 |
| 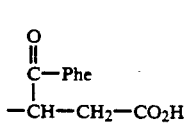 | 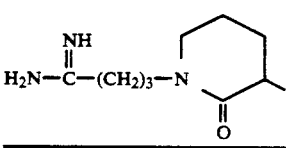 |
TABLE II
| | |
|---|---|
| 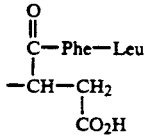 | 2.9 μM |
| 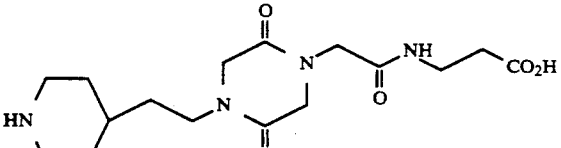 | 5.6 μM |
| 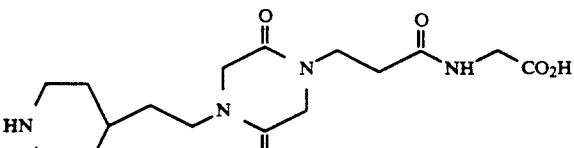 | 19 μM |
| 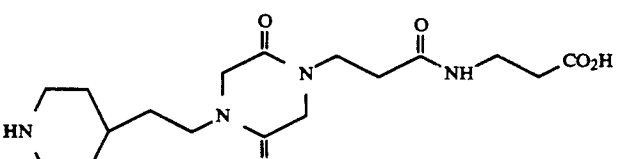 | 20 μM |

TABLE II-continued

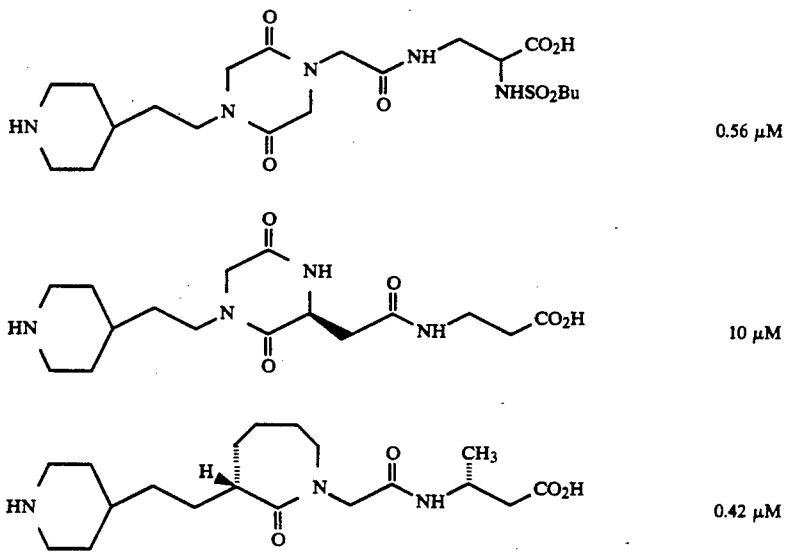

| | |
|---|---|
| (structure 1) | 0.56 μM |
| (structure 2) | 10 μM |
| (structure 3) | 0.42 μM |

In vivo Activity

The following protocols were used to determine in vivo activity in dogs of fibrinogen receptor antagonists of the present invention.

A mongrel dog of either sex (weighing 7.5 to 11.5 kg) is comfortably positioned in a nylon sling which exposes the legs and keeps the dog stationary. Five ml of blood is withdrawn from either saphenous or cephalic veins with a plastic syringe containing 0.5 ml of 3.8% citrate via a 19-gauge butterfly. An additional 1 ml of citrated blood is taken to measure whole blood platelet counts. Ex vivo platelet aggregations are done with the agonists ADP (10 μM) and collagen (10 μg/ml) both primed with 1μM epinephrine. Platelet-rich plasma (PRP) is obtained by centrifuging the blood at 150 x g for 5 minutes. Platelet counts are adjusted to 200,000/mm³ with platelet-poor plasma.

Oral administration of a drug is done either as a gelatin capsule or a gastric lavage. For the gastric lavage method, 5 ml of the drug solution is administered to the dog through a feeding tube. Blood samples for ex vivo platelet aggregation are taken at the following time points: 0,20, 40, 70, 90, 150, 200, 250, 300, 350, 480 min. 24 hr. 30 hr, and 48 hr. At each time point, the remaining platelet-poor plasma is saved and frozen for drug levels. Three additional blood samples are taken at 30, 55, and 110 minutes after dosing for drug plasma levels.

For the intravenous infusion, blood samples for ex vivo platelet aggregation are taken at the following time points: 0,30, 45, 60, 90 and 120 min into the infusion and 2,5, 15, 30, 60, 90, 120, 180, 240, 300, 360, and 420 minutes after the infusion stops. At each time point, the remaining platelet-poor plasma is saved and frozen for drug levels. The drug is infused for 120 minutes at a constant rate of 0.1 ml/min.

For the intravenous bolus, 5 ml of the drug solution is administered quickly. Blood samples for x vivo platelet aggregation are taken at 0, 1, 5, 10, 15, 30, 45, 60, 90, 120, 180, and 240 minutes after the bolus. At all time points, the remaining platelet-poor plasma was saved and frozen for drug levels.

In the oral and intravenous groups, blood collection times are recorded at each time point in order to determine drug plasma levels.

The following compound

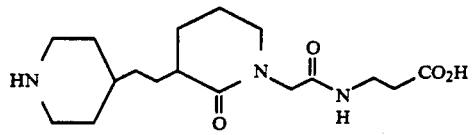

was evaluated according to the procedures described above.

Inhibition of platelet aggregation (% of control) induced by intravenous infusion at rates of 10 μg/kg/min and 25 μg/kg/min was measured. Inhibition was nearly complete during infusion and partial inhibition existed for several hours after infusion cessation.

Inhibition of platelet aggregation (% of control) induced by single oral administration of 2 mg/kg was also measured. % Inhibition of platelet aggregation was greater than 50% for a period of eight hours.

What is claimed is:

1. A fibrinogen receptor antagonist of the formula

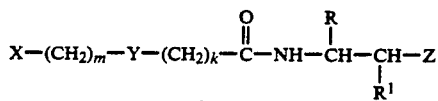

wherein:

X is

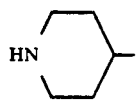

Y is

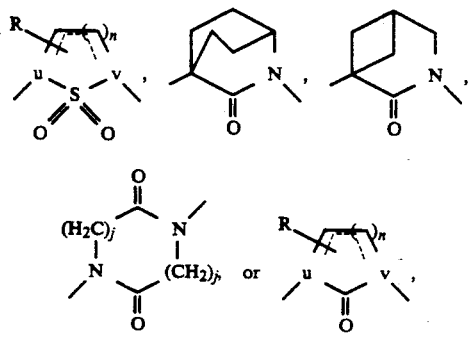

wherein n=0-5 and j=0-3;
Z is —CO$_2$R$_2$,

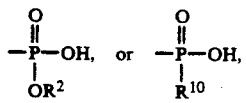

wherein
R$^{10}$ is C$_{1-8}$alkyl, aryl, arylC$_{1-8}$alkyl,
u is C or N,
v is C or N,
R is
  hydrogen,
  C$_{0-6}$alkyl, either unsubstituted or substituted, with one or more groups selected from fluoro, chloro, bromo, iodo, hydroxyl, C$_{1-5}$alkylcarbonyl(C$_{0-8}$alkyl)amino, arylC$_{1-5}$ alkylcarbonyl(C$_{0-8}$alkyl)amino, aryloxy, C$_{1-10}$alkoxy, C$_{1-5}$alkoxycarbonyl, C$_{0-5}$alkylaminocarbonyl, C$_{1-5}$alkylcarbonyloxy, C$_{3-8}$cycloalkyl, aryl, oxo, amino, C$_{1-6}$alkylaminocarbonyl, phenylC$_{1-3}$alkylamino, aminocarbonylC$_{0-4}$alkyl, C$_{1-8}$alkylsulfonyl(C$_{0-8}$alkyl)amino, aryl C$_{0-10}$alkylsulfonyl(C$_{0-8}$alkyl)amino, arylC$_{0-8}$alkylsulfonyl, C$_{0-8}$alkylsulfonyl, hydroxycarbonylC$_{0-5}$alkyl, C$_{8}$alkyloxycarbonyl(C$_{0-8}$alkyl)amino, arylC$_{0-10}$alkyloxycarbonyl(C$_{0-8}$alkyl)amino, C$_{0-8}$alkylaminocarbonyl(C$_{0-8}$alkyl)amino, arylC$_{0-8}$alkylaminocarbonyl(C$_{0-8}$alkyl)amino, C$_{0-8}$alkylaminocarbonyloxy, arylC$_{0-10}$alkylaminocarbonyloxy, C$_{0-8}$alkylaminosulfonyl(C$_{0-8}$alkyl)amino, arylC$_{0-8}$alkylaminosulfonyl(C$_{0-8}$alkyl)amino, C$_{0-8}$alkylaminosulfonyl, and arylC$_{0-8}$alkylaminosulfonyl; provided that the carbon atom to which R or R$^1$ is attached bear only one heteroatom;
R$^1$ is
  hydrogen,
  C$_{0-6}$alkyl, either unsubstituted or substituted, with one or more groups selected from fluoro, chloro, bromo, iodo, hydroxyl, C$_{1-5}$alkylcarbonyl(C$_{0-8}$alkyl)amino, arylC$_{5}$alkylcarbonyl(C$_{0-8}$alkyl)amino, aryloxy, C$_{1-10}$alkoxy, C$_{1-5}$alkoxycarbonyl, C$_{0-5}$alkylaminocarbonyl, C$_{1-5}$alkylcarbonyloxy, C$_{3-8}$ cycloalkyl, aryl, oxo, amino, C$_{1-6}$alkyl, C$_{1-3}$alkylamino, aminoC$_{1-3}$ alkyl, arylC$_{0-5}$alkylaminocarbonyl, phenylC$_{1-3}$alkylamino, aminocarbonylC$_{0-4}$alkyl, C$_{1-8}$alkylsulfonyl(C$_{0-8}$alkyl)amino, aryl C$_{0-10}$alkylsulfonyl(C$_{0-8}$alkyl)amino, arylC$_{0-8}$alkylsulfonyl, C$_{0-8}$alkylsulfonyl, hydroxycarbonylC$_{0-5}$alkyl, C$_{1-8}$alkyloxycarbonyl(C$_{0-8}$alkyl)amino, arylC$_{0-10}$alkoxycarbonyl(C$_{0-8}$alkyl)amino, C$_{0-8}$alkylaminocarbonyl(C$_{0-8}$alkyl)amino, arylC$_{0-8}$alkylaminocarbonyl(C$_{0-8}$alkyl)amino, C$_{0-8}$alkylaminocarbonyloxy, arylC$_{0-10}$alkylaminocarbonyloxy, C$_{0-8}$alkylaminosulfonyl(C$_{0-8}$alkyl)amino, arylC$_{0-8}$alkylaminosulfonyl(C$_{0-8}$alkyl)amino, C$_{0-8}$alkylaminosulfonyl, and arylC$_{0-8}$alkylaminosulfonyl; provided that the carbon atom to which R or R$^1$ is attached bear only one heteroatom;
R$^2$ is
  hydrogen,
  C$_{1-12}$alkyl, unsubstituted or substituted, with one or more C$_{1-6}$alkyl groups,

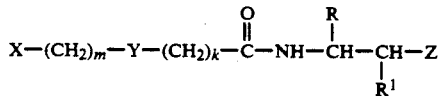

where R$^9$ is C$_{1-6}$alkyl, branched or unbranched, or phenyl, and wherein R$^9$, when appearing more than once, can be the same or different;
m is 1-4,
or the pharmaceutically acceptable salts thereof, or optical isomer thereof.

2. A fibrinogen receptor antagonist of claim 1 having the formula $$X-(CH_2)_m-Y-(CH_2)_k-\overset{O}{\overset{\|}{C}}-NH-\underset{R^1}{\overset{R}{\underset{|}{\overset{|}{C}H}}}-CH-Z$$

wherein:
X is

Y is

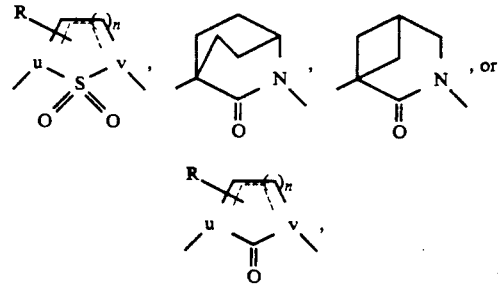

wherein n=0-5;
Z is —CO$_2$R$_2$,

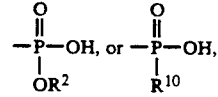

wherein
R$^{10}$ is C$_{1-8}$alkyl, aryl, arylC$_{1-8}$alkyl,
u is C or N,
v is C or N, R is
  hydrogen,
  $C_{0-6}$alkyl, either unsubstituted or substituted, with one or more groups selected from fluoro, chloro, bromo, iodi, hydroxyl, $C_{1-5}$alkylcarbonyl($C_{0-8}$alkyl)amino, aryl$C_{1-5}$ alkylcarbonyl($C_{0-8}$alkyl)amino, aryloxy, $C_{1-10}$alkoxy, $C_{1-5}$alkoxycarbonyl, $C_{0-5}$alkylaminocarbonyl, $C_{1-5}$alkylcarbonyloxy, $C_{3-8}$ cycloalkyl, aryl, oxo, amino, $C_{1-6}$ alkyl, $C_{1-3}$alkylamino, amino$C_{1-3}$ alkyl, aryl$C_{0-5}$alkylaminocarbonyl, phenyl$C_{1-3}$alkylamino, aminocarbonyl$C_{0-4}$alkyl, $C_{1-8}$alkylsulfonyl($C_{0-8}$alkyl)amino, aryl $C_{0-10}$alkylsulfonyl($C_{0-8}$alkyl)amino, aryl$C_{0-8}$alkylsulfonyl, $C_{0-8}$alkylsulfonyl, hydroxycarbonyl$C_{0-5}$alkyl, $C_{1-8}$alkyloxycarbonyl($C_{0-8}$alkyl)amino, aryl$C_{0-10}$alkyloxycarbonyl($C_{0-8}$alkyl)amino, $C_{0-8}$alkylaminocarbonyl($C_{0-8}$alkyl)amino, aryl$C_{0-8}$alkylaminocarbonyl($C_{0-8}$alkyl)amino, $C_{0-8}$alkylaminocarbonyloxy, aryl$C_{0-10}$alkylaminocarbonyloxy, $C_{0-8}$alkylaminosulfonyl($C_{0-8}$alkyl)amino, aryl$C_{0-8}$alkylaminosulfonyl($C_{0-8}$alkyl)amino, $C_{0-8}$alkylaminosulfonyl, and aryl$C_{0-8}$alkylaminosulfonyl; provided that the carbon atom to which R or $R^1$ is attached bear only one heteroatom;
$R^1$ is
  hydrogen,
  $C_{0-6}$alkyl, either unsubstituted or substituted, with one or more groups selected from fluoro, chloro, bromo, iodo, hydroxyl, $C_{1-5}$alkylcarbonyl($C_{0-8}$alkyl)amino, aryl$C_{1-5}$alkylcarbonyl($C_{0-8}$alkyl)amino, aryloxy, $C_{1-10}$alkoxy, $C_{1-5}$alkoxycarbonyl, $C_{0-5}$alkylaminocarbonyl, $C_{1-5}$alkylcarbonyloxy, $C_{3-8}$ cycloalkyl, aryl, oxo, amino, $C_{1-6}$ alkyl, $C_{1-3}$alkylamino, amino$C_{1-3}$ alkyl, aryl$C_{0-5}$alkylaminocarbonyl, phenyl$C_{1-3}$alkylamino, aminocarbonyl$C_{0-4}$alkyl, $C_{1-8}$alkylsulfonyl($C_{0-8}$alkyl)amino, aryl $C_{0-10}$alkylsulfonyl($C_{0-8}$alkyl)amino, aryl$C_{0-8}$alkylsulfonyl, $C_{0-8}$alkylsulfonyl, hydroxycarbonyl$C_{0-5}$alkyl, $C_{1-8}$alkyloxycarbonyl($C_{0-8}$alkyl)amino, aryl$C_{0-10}$alkyloxycarbonyl($C_{0-8}$alkyl)amino, $C_{0-8}$alkylaminocarbonyl($C_{0-8}$alkyl) amino, aryl$C_{0-8}$alkylaminocarbonyl($C_{0-8}$alkyl)amino, $C_{0-8}$alkylaminocarbonyloxy, aryl$C_{0-10}$alkylaminocarbonyloxy, $C_{0-8}$alkylaminosulfonyl($C_{0-8}$alkyl)amino, aryl$C_{0-8}$alkylaminosulfonyl($C_{0-8}$alkyl)amino, $C_{0-8}$alkylaminosulfonyl, and aryl$C_{0-8}$alkylaminosulfonyl; provided that the carbon atom to which R or $R^1$ is attached bear only one heteroatom;
$R^2$ is
  hydrogen,
  $C_{1-12}$alkyl, unsubstituted or substituted, with one or more $C_{1-6}$alkyl groups,

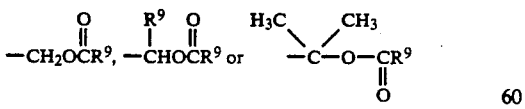

where $R^9$ is $C_{1-6}$alkyl, branched or unbranched, or phenyl, and where $R^9$, when appearing more than once, can be the same or different;
k is 1–4; and
m is 1–4,
or the pharmaceutically acceptable salts thereof, or optical isomer thereof.

3. A fibrinogen receptor antagonist of claim 2 having the formula

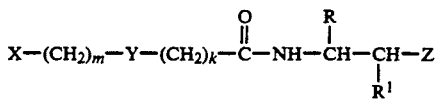

wherein:
X is

Y is

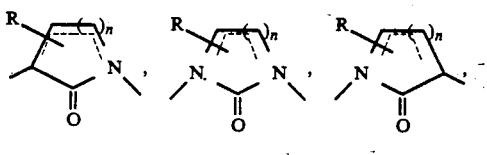

wherein n = 1–3;
Z is —$CO_2H$,
R is
  hydrogen,
  $C_{0-6}$alkyl, either unsubstituted or substituted, with one or more groups selected from fluoro, chloro, bromo, iodo, hydroxyl, $C_{1-5}$alkylcarbonyl($C_{0-8}$alkyl)amino, aryl$C_{1-5}$alkylcarbonyl($C_{0-8}$alkyl)amino, aryloxy, $C_{1-10}$alkoxy, $C_{1-5}$alkoxycarbonyl, $C_{0-5}$alkylaminocarbonyl, $C_{1-5}$alkylcarbonyloxy, $C_{3-8}$ cycloalkyl, aryl, oxo, amino, $C_{1-6}$ alkyl, $C_{1-3}$alkylamino, amino$C_{1-3}$ alkyl, aryl$C_{0-5}$alkylaminocarbonyl, phenyl$C_{1-3}$alkylamino, aminocarbonylChd 0-4alkyl, $C_{1-8}$alkylsulfonyl($C_{0-8}$alkyl)amino, aryl $C_{0-10}$alkylsulfonyl($C_{0-8}$alkyl)amino, aryl$C_{0-8}$alkylsulfonyl, $C_{0-8}$alkylsulfonyl, hydroxycarbonyl$C_{0-5}$alkyl, $C_{1-8}$alkyloxycarbonyl($C_{0-8}$alkyl)amino, aryl$C_{0-10}$alkyloxycarbonyl($C_{0-8}$alkyl)amino, $C_{0-8}$alkylaminocarbonyl($C_{0-8}$alkyl)amino, aryl$C_{0-8}$alkylaminocarbonyl($C_{0-8}$alkyl)amino, $C_{0-8}$alkylaminocarbonyloxy, aryl$C_{0-10}$alkylaminocarbonyloxy, $C_{0-8}$alkylaminosulfonyl($C_{0-8}$alkyl)amino, aryl$C_{0-8}$alkylaminosulfonyl($C_{0-8}$alkyl)amino, $C_{0-8}$alkylaminosulfonyl, and aryl$C_{0-8}$alkylaminosulfonyl; provided that the carbon atom to which R or $R^1$ is attached bear only one heteroatom;
$R^1$ is
  hydrogen,
  $C_{0-6}$alkyl, either unsubstituted or substituted, with one or more groups selected from fluoro, chloro, bromo, iodo, hydroxyl, $C_{1-5}$alkylcarbonyl($C_{0-8}$alkyl)amino, aryl$C_{1-5}$alkylcarbonyl($C_{0-8}$alkyl)amino, aryloxy, $C_{1-10}$alkoxy, $C_{1-5}$alkoxycarbonyl, $C_{0-5}$alkylaminocarbonyl, $C_{1-5}$alkylcarbonyloxy, $C_{3-8}$ cycloalkyl, aryl, oxo, amino, $C_{1-6}$ alkyl, $C_{1-3}$alkylamino, amino$C_{1-3}$ alkyl, aryl$C_{0-5}$alkylaminocarbonyl, phenyl$C_{1-3}$alkylamino, aminocarbonyl$C_{0-4}$alkyl, $C_{1-8}$alkylsulfonyl($C_{0-8}$alkyl)amino, aryl $C_{0-10}$alkylsulfonyl($C_{0-8}$alkyl)amino, aryl$C_{0-8}$alkylsulfonyl, $C_{0-8}$alkylsulfonyl, hydroxycarbonyl$C_{0-5}$alkyl, $C_{1-8}$alkyloxycarbonyl(C₀₋₈alkyl)amino, arylC₀₋₁₀alkyloxycarbonyl(C₀₋₈alkyl)amino, C₀₋₈alkylaminocarbonyl(C₀₋₈alkyl)amino, arylC₀₋₈alkylaminocarbonyl(C₀₋₈alkyl)amino, C₀₋₈alkylaminocarbonyloxy, arylC₀₋₁₀alkylaminocarbonyloxy, C₀₋₈alkylaminosulfonyl(C₀₋₈alkyl)amino, arylC₀₋₈alkylaminosulfonyl(C₀₋₈alkyl)amino, C₀₋₈alkylaminosulfonyl, and arylC₀₋₈alkylaminosulfonyl; provided that the carbon atom to which R or R¹¹ is attached bear only one heteroatom;

k is 1; and m is 1-4, or the pharmaceutically acceptable salts thereof, or optical isomer thereof.

4. A compound of claim 1 selected from the group consisting of:

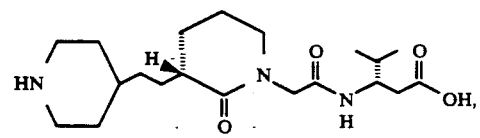

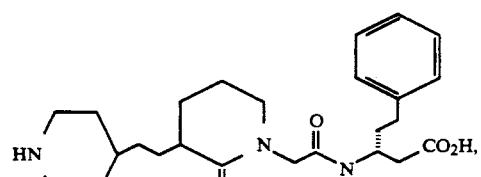

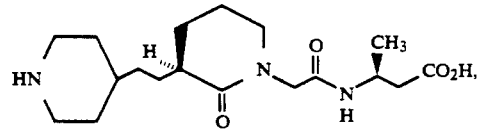

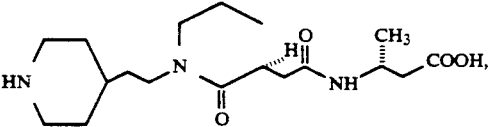

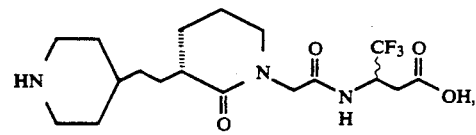

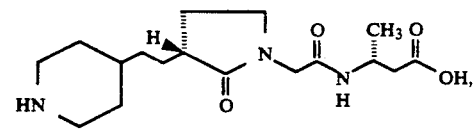

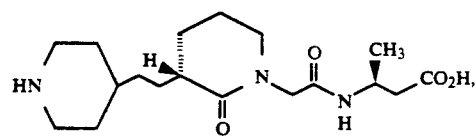

-continued

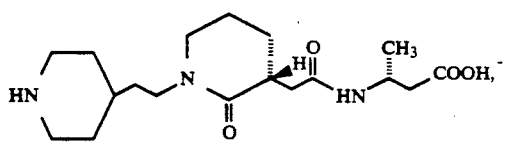

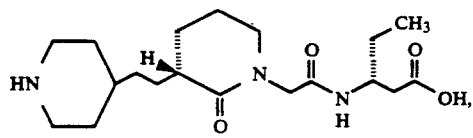

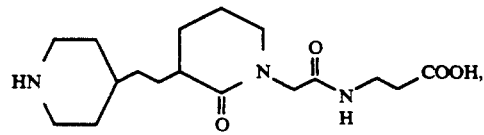

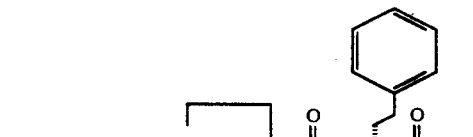

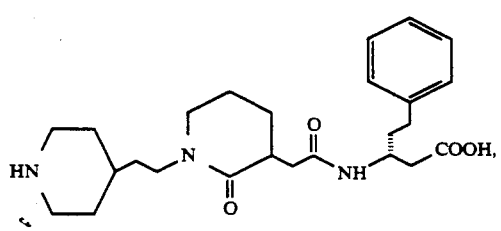

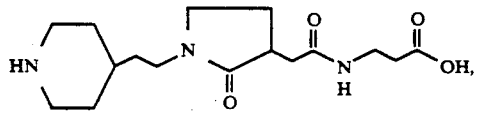

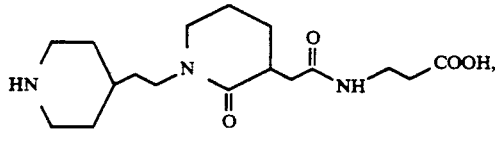

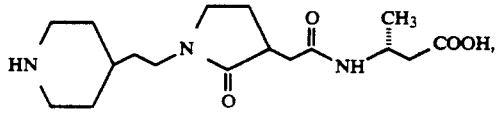

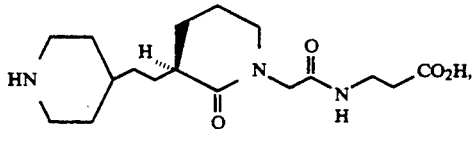

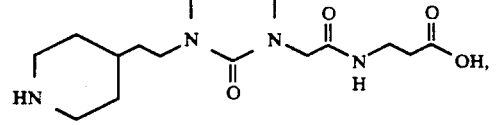

-continued
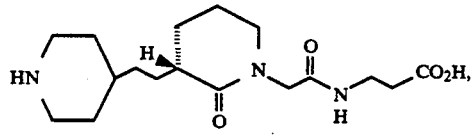
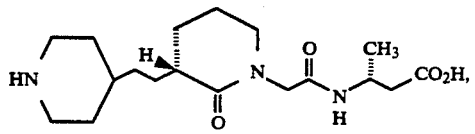
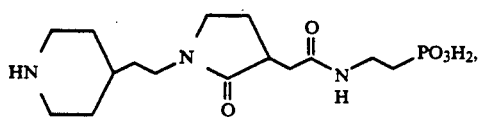
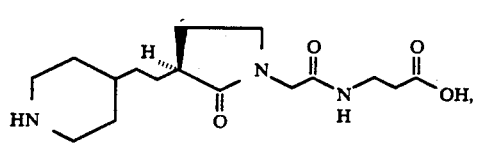
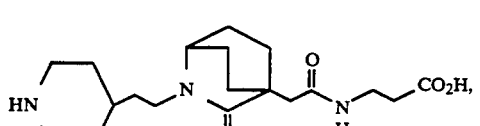
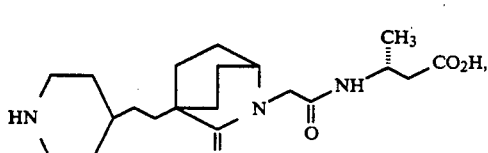
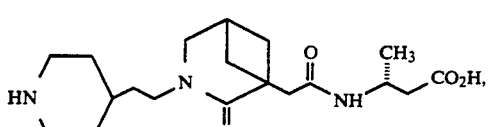
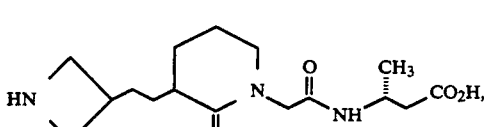
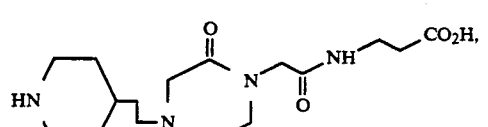
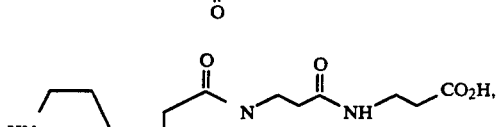
-continued
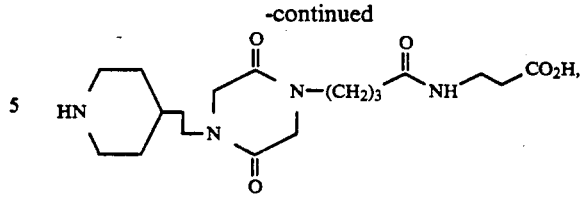
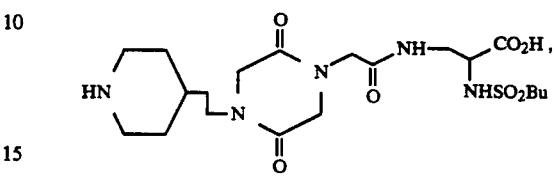
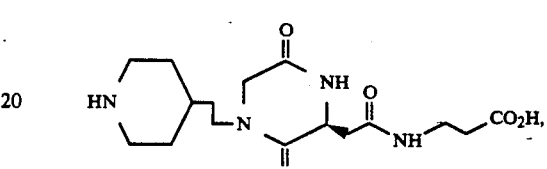
and
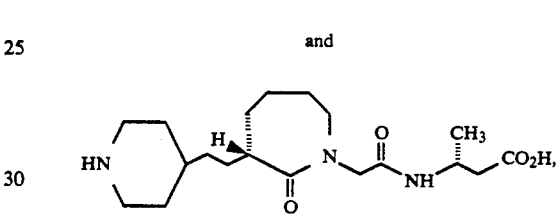
or pharmaceutically acceptable salts thereof.
5. A compound which is:
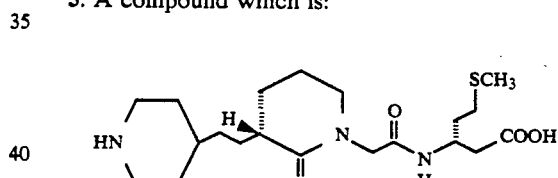
or pharmaceutically acceptable salts thereof.
6. A compound of claim 4 which is:
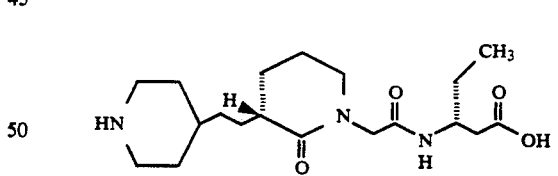
or pharmaceutically acceptable salts thereof.
7. A compound of claim 4 which is:
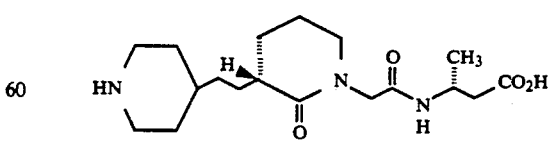
or pharmaceutically acceptable salts thereof.
8. A compound of claim 4 which is:

105

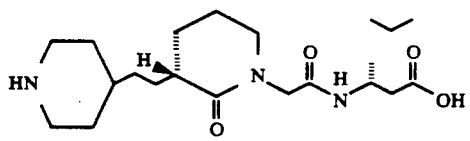

or pharmaceutically acceptable salts thereof.

9. A compound of claim 4 which is

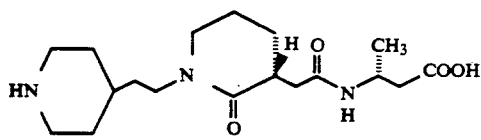

or pharmaceutically acceptable salts thereof.

10. A compound of claim 1 which is:

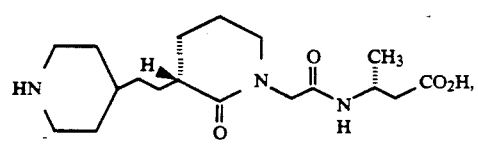

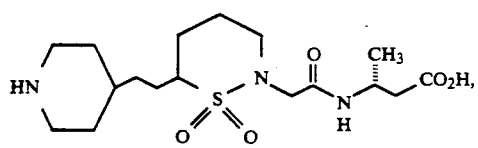

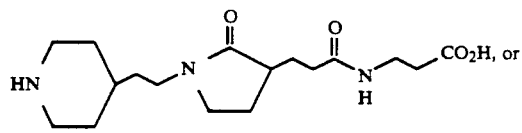

106

-continued

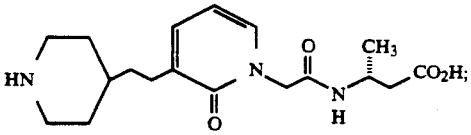

or pharmaceutically acceptable salts thereof.

11. A composition for inhibiting the binding of fibrinogen to blood platelets in a mammal, comprising a compound of claim 1 and a pharmaceutically acceptable carrier.

12. A composition for inhibiting the binding of fibrinogen to blood platelets in a mammal comprising a compound of claim 4 and a pharmaceutically acceptable carrier.

13. A composition for inhibiting the binding of fibrinogen to blood platelets in a mammal comprising the compound of claim 5 and a pharmaceutically acceptable carrier.

14. A composition for inhibiting the binding of fibrinogen to blood platelets in a mammal comprising the compound of claim 6 and a pharmaceutically acceptable carrier.

15. A composition for inhibiting the binding of fibrinogen to blood platelets in a mammal comprising the compound of claim 7 and a pharmaceutically acceptable carrier.

16. A composition for inhibiting the binding of fibrinogen to blood platelets in a mammal comprising the compound of claim 8 and a pharmaceutically acceptable carrier.

17. A composition for inhibiting the binding of fibrinogen to blood platelets in a mammal comprising the compound of claim 9 and a pharmaceutically acceptable carrier.

18. A composition for inhibiting the binding of fibrinogen to blood platelets in a mammal comprising the compounds of claim 10 and a pharmaceutically acceptable carrier.

* * * * *